(12) United States Patent
Ashley et al.

(10) Patent No.: US 8,754,190 B2
(45) Date of Patent: Jun. 17, 2014

(54) CONTROLLED RELEASE FROM MACROMOLECULAR CONJUGATES

(75) Inventors: Gary Ashley, Alameda, CA (US);
Daniel V. Santi, San Francisco, CA (US)

(73) Assignee: Prolynx LLC, San Francisco, CA (US)

( * ) Notice: Subject to any disclaimer, the term of this patent is extended or adjusted under 35 U.S.C. 154(b) by 0 days.

(21) Appl. No.: 13/696,299

(22) PCT Filed: May 5, 2011

(86) PCT No.: PCT/US2011/035423
§ 371 (c)(1),
(2), (4) Date: Jan. 22, 2013

(87) PCT Pub. No.: WO2011/140393
PCT Pub. Date: Nov. 10, 2011

(65) Prior Publication Data
US 2013/0116407 A1      May 9, 2013

Related U.S. Application Data

(60) Provisional application No. 61/331,738, filed on May 5, 2010.

(51) Int. Cl.
| | |
|---|---|
| A61K 38/06 | (2006.01) |
| C07K 5/00 | (2006.01) |
| C07K 7/00 | (2006.01) |
| C07K 16/00 | (2006.01) |
| C07K 17/00 | (2006.01) |
| C07D 487/00 | (2006.01) |
| C07D 491/00 | (2006.01) |
| C07D 513/00 | (2006.01) |
| C07D 239/02 | (2006.01) |
| C07C 247/00 | (2006.01) |
| C07J 41/00 | (2006.01) |

(52) U.S. Cl.
USPC ............. 530/331; 540/476; 544/311; 546/48; 552/12

(58) Field of Classification Search
None
See application file for complete search history.

(56) References Cited

U.S. PATENT DOCUMENTS

| | | | |
|---|---|---|---|
| 3,758,554 | A | 9/1973 | Gaj et al. |
| 4,200,564 | A | 4/1980 | Komminoth et al. |
| 4,539,008 | A | 9/1985 | Andrews et al. |
| 7,585,837 | B2 | 9/2009 | Shechter et al. |
| 2004/0013637 | A1 | 1/2004 | Bentley et al. |
| 2006/0171920 | A1 | 8/2006 | Shechter et al. |
| 2009/0158668 | A1 | 6/2009 | Nonaka et al. |

FOREIGN PATENT DOCUMENTS

| | | |
|---|---|---|
| DE | 41 19 544 | 10/1992 |
| FR | 2 034 379 | 12/1970 |
| GB | 1 231 946 | 5/1971 |
| WO | WO-2004/089280 | 10/2004 |
| WO | WO-2008/082613 | 7/2008 |
| WO | WO 2009158668 A1 * | 12/2009 |

OTHER PUBLICATIONS

Beaumont et al "Design of Ester Prodrugs to Enhance Oral Absorption of Poorly Permeable Compounds: Challenges to the Discovery Scientist" Curr Drug Metab 4:461-485. Published 2003.*
Ettmayer et al "Lessons Learned from Marketed and Investigational Prodrugs" J Med Chem 47:2393-2404. Published online Apr. 13, 2004.*
Muller C "Prodrug Approaches for Enhancing the Bioavailability of Drugs with Low Solubility" Chemisry and Biodiversity 6:2071-2083. Published Nov. 2009.*
Sing et al "Recent Trends in Targeted Anticancer Prodrug and Conjugate Design" Curr Med Chem 15:1802-1826. Published 2008.*
Testa B "Prodrug research: futile or fertile?" Biochem Pharmacol 68:2097-2106. Published 2004.*
Routzahn K and Waugh D "Differential effects of supplementary affinity tags on the solubility of MBP fusion proteins" J Struc Functional Genomics 2:83-92. Published 2002.*
Burke et al., "Design, Synthesis, and Biological Evaluation of Antibogy—Drug Conjugates Comprised of Potent Camptothecin Analogues", Bioconjugate Chem. (2009) 20:1242-1250.
CAS 32861-14-6 (1984) Chemical Abstract Service, STN.
Madec-Lougerstay et al., "Synthesis of self-immolative glucuronide spacers based on aminomethylcarbamate. Application to 5-fluorouracil prodrugs for antibody-directed enzyme prodrug therapy", J. Chem. Soc., Perkin Trans. 1 (1999) pp. 1369-1375.
Majumdar et al., "Synthesis, hydrolyses and dermal delivery of N-alkyl-N-alkyloxycarbonylaminomethyl (NANAOCAM) derivatives of phenol, imide and thiol containing drugs", Bioorganic & Medicinal Chemistry Letters (2006) 16:3590-3594.
Supplementary European Search Report for EP 11778384.5, mailed Sep. 27, 2013, 11 pages.
International Search Report for PCT/US2011/035423, mailed Aug. 2, 2011, 1 page.
Majundar and Sloan, "N-Alkyl-N-alkyloxycarbonylaminomethyl (NANAOCAM) prodrugs of carboxylic acid containing drugs," Bioorg. Med. Chem. Lett. ((2007) 17:1447-1450.
Notice of the First Office Action (including translation) for CN 201180022347.0, mailed Oct. 15, 2013, 20 pages.

* cited by examiner

*Primary Examiner* — Cecilia J Tsang
*Assistant Examiner* — Zachary J Miknis
(74) *Attorney, Agent, or Firm* — Morrison & Foerster LLP

(57) ABSTRACT

The invention relates to conjugates of macromolecular carriers and drugs comprising linkers that release the drug or a prodrug through rate-controlled beta-elimination, and methods of making and using the conjugates.

22 Claims, 8 Drawing Sheets

Panel A

Panel B

US 8,754,190 B2

CONTROLLED RELEASE FROM MACROMOLECULAR CONJUGATES

CROSS-REFERENCE TO RELATED APPLICATIONS

This application is the national phase of PCT application PCT/US2011/035423 having an international filing date of 5 May 2011, which claims benefit under 35 U.S.C. §119(e) to provisional application 61/331,738 filed 5 May 2010. The contents of the above patent applications are incorporated by reference herein in their entirety.

TECHNICAL FIELD

The invention relates to macromolecular conjugates between macromolecular carriers and drugs comprising linkers that release drug through controlled beta-elimination reactions.

BACKGROUND

Drug molecules are covalently bound to macromolecular carriers in order to enhance pharmaceutical properties, such as half-life, stability, solubility, tolerability, and safety. In one method, drug moieties are coupled to macromolecules through a permanent linker, but this approach is limited by at least two factor: 1) the linker must be attached to the drug moiety at a site that does not hinder biological activity, and 2) permanent conjugates generally cannot cross the cell membrane, so the approach may only be feasible for extracellular drug targets.

In a second approach, covalently bound drug-macromolecule conjugates employ controlled release of drugs or growth factors useful in medicine. For example, compositions and methods have been described for controlled release of drugs covalently coupled to polyethylene glycol (PEG). This approach does not require an extracellular drug target, and the linkage site is preferably one that does hinder the drug's activity so that it is somewhat masked until it is released from the carrier. Typically, for alcohol- or phenol-containing drugs, the drug is attached to the carrier by an ester or carbonate linkage that can be hydrolyzed, usually by a serum esterase. Examples are PEG-camptothecin, PEG-SN38, PEG-irinotecan and PEG-docetaxel. Adaptations have been made to accommodate amine-containing drugs whereby a PEG moiety is connected by a cleavable ester to a self-immolating carbamate. This technology has been applied to peptides and proteins as well as to daunorubicin, amphotericin, Ara-C and other small molecules. However, drug release rates in these cases is unpredictable and difficult to adjust, because esterase activity varies between species and individuals, and certain compartments are esterase-deficient (e.g., topical, intra-ocular, interstitial areas).

Herein, a drug conjugate system is described which allows for drug release through a rate-controlled, beta-elimination mechanism.

The Weizmann Institute developed a system in which a protein or polymer carrier is attached to linkers such as fluorenylmethoxycarbonyl (Fmoc) or its 2-sulfo derivative (Fms). These are described in U.S. Pat. No. 7,585,837. These linkers release drugs via a non-enzymatic beta-elimination mechanism; however, tunable control over the release rate remains a problem with this system.

PCT publication WO2009/158668 describes releasable drug conjugates to macromolecules wherein the rate of beta-elimination is controlled by a trigger independent of the macromolecule itself. This solves a problem left unsolved in the prior art. The '668 PCT publication provides for linkers that are most directly applicable to basic amine-containing drugs, as the linkers attach to the drugs via carbamate or thiocarbamate linkages. There is thus an unmet need for new cleavable linkers that allow for conjugation of alcohol-, phenol-, thiol-, thiophenol-, and certain nitrogen-containing drugs to macromolecular carriers, and that allow for subsequent release of these drugs at controlled rates under physiological conditions. Notably, over 50% of FDA-approved drugs under a molecular weight of 1200 have an primary or secondary aliphatic hydroxyl, phenol, or thiol group, and approximately 8% contain a sulfonamide, pyrrole, or indole nitrogen (see DrugBank). The present invention meets this need by providing drug-macromolecule conjugates linked via N-oxymethyl, N-(heterocyclic amino)methyl, and N-thiomethyl carbamates that are cleavable by beta-elimination under controlled rates to provide the free drugs. Furthermore, the linkers described herein release the free drug molecules without relying on the activity or presence of physiological enzymes.

While simple N-alkoxymethyl, N-acyloxymethyl, and N-thiomethyl carbamates have been previously reported as prodrugs [see, for example, N-acyloxymethyl carbamates described by Majumdar & Sloan, *Bioorg. Med. Chem. Lett.* (2007) 17: 1447-1450] or as modifiers for textiles [see, for example, U.S. Pat. Nos. 4,539,008; 4,200,564; and 3,758,554], such compounds do not have the ability to release the free drug molecules by rate-controlled beta-elimination.

SUMMARY OF THE INVENTION

The present invention provides conjugates of drugs with macromolecular carriers comprising cleavable linkers that allow for subsequent release of the drugs at controlled rates under physiological conditions, as well as the cleavable linkers, linker-drug molecules comprising the cleavable linkers, macromolecular carriers comprising the cleavable linkers, and methods for the preparation and use of the above.

In general, the invention is directed to a compound of the formula $$R^1-\underset{\underset{H}{|}}{\overset{\overset{R^2}{|}}{C}}-(CH=CH)_m-\underset{\underset{R^5}{|}}{\overset{\overset{R^5}{|}}{C}}-O-\overset{\overset{O}{\|}}{C}-NB-CH_2-Z \qquad (V)$$

wherein m is 0 or 1;
wherein at least one, or both $R^1$ and $R^2$ is independently CN; $NO_2$;
   optionally substituted aryl;
   optionally substituted heteroaryl;
   optionally substituted alkenyl;
   optionally substituted alkynyl;
   $COR^3$ or $SOR^3$ or $SO_2R^3$ wherein
     $R^3$ is H or optionally substituted alkyl;
     aryl or arylalkyl, each optionally substituted;
     heteroaryl or heteroarylalkyl, each optionally substituted; or
     $OR^9$ or $N(R^9)_2$ wherein each $R^9$ is independently H or optionally substituted alkyl, or both $R^9$ groups taken together with the nitrogen to which they are attached form a heterocyclic ring;
   $SR^4$ wherein
     $R^4$ is optionally substituted alkyl;
     aryl or arylalkyl, each optionally substituted; or heteroaryl or heteroarylalkyl, each optionally substituted;

wherein $R^1$ and $R^2$ may be joined to form a 3-8 membered ring; and wherein one and only one of $R^1$ and $R^2$ may be H or alkyl, arylalkyl or heteroarylalkyl, each optionally substituted;

each $R^5$ is independently H or is alkyl, alkenylalkyl, alkynylalkyl, aryl, arylalkyl, heteroaryl or heteroarylalkyl, each optionally substituted;

Z is a residue of a drug or prodrug coupled through O, S, or non-basic N or is a nucleofuge which permits such coupling; and B is alkyl, aryl, arylalkyl, heteroaryl, or heteroarylalkyl, each optionally substituted; and wherein one of $R^1$, $R^2$, $R^5$ or B is coupled to a macromolecule or comprises a functional group allowing for connection to a macromolecule.

Thus, in one aspect, the invention is directed to conjugates of drugs with macromolecular carriers comprising cleavable linkers having the formula (I)

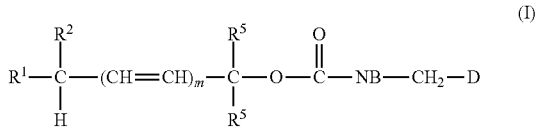
(I)

wherein $R^1$, $R^2$, $R^5$, m and B are defined as above and wherein D is a drug or prodrug coupled through O, S or non-basic N and wherein one of $R^1$, $R^2$, $R^5$ or B is coupled to a macromolecule.

In a second aspect, the present invention provides cleavable linker reagent compounds that are precursors to the compounds of formula (I) having formula (II),

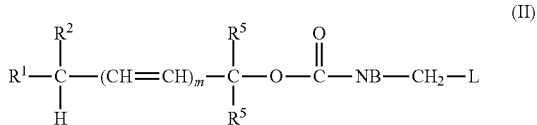
(II)

wherein $R^1$, $R^2$, $R^5$, m and B are as defined above; and L is a nucleofuge that allows for connection to a drug or prodrug through O, S, or non-basic N. In formula (II), rather than being coupled to a macromolecule, at least one of the $R^1$, $R^2$, $R^5$, and B groups comprises a functional group allowing for connection to a macromolecule.

In a third aspect, the present invention provides linker-drug compounds having formula (III)

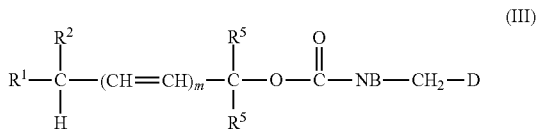
(III)

wherein the $R^1$, $R^2$, $R^5$, m and B groups are as defined above; D is the residue of a drug or prodrug connected via O, S, or non-basic N; and wherein at least one of the $R^1$, $R^2$, $R^5$ or B groups comprises a functional group allowing for connection to a macromolecule as described above.

In a fourth aspect, the present invention provides macromolecular carriers comprising cleavable linkers having formula (IV),

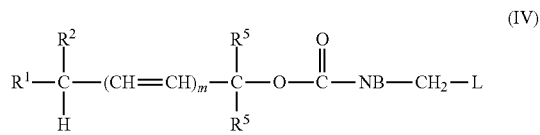
(IV)

wherein the $R^1$, $R^2$, $R^5$, m and B groups are as defined above; L is a nucleofuge that allows for connection to a drug or prodrug through O, S, or non-basic N; and wherein, as in formula (I), at least one of $R^1$, $R^2$, $R^5$ or B is further connected to a macromolecule.

In a fifth aspect, the present invention provides for a drug-macromolecule conjugate, wherein the drug is connected to the macromolecule via a linker, the drug molecule is attached to the linker through an O, S, or non-basic N, and wherein the drug is released from the conjugate under physiological conditions through a beta-elimination reaction.

In other aspects, the present invention provides methods for the preparation of the compounds of formulas (I), (II), (III), and (IV), and methods for their use.

DESCRIPTION OF THE INVENTION

The present invention represents an improvement over standard conjugate practices, and has additional advantages over the PEGylated releasable drug compositions such as those described in the above-referenced PCT publication WO2009/158668. Advantages include retaining a drug or prodrug in inactive form until released from the macromolecular carrier, a multiplicity of binding sites for the drug so that the drug dosage may be increased, thus permitting delivery of less potent drugs, and provision of protection against degrading enzymes or other inactivating conditions.

Another advantage of the compositions of the invention is that they afford effective delivery of drugs to the lymphatic system. Because the compounds of the invention have molecular weights that are significantly higher than the molecular weight of the drug, they are capable of maintaining the drug in the lymphatic system when the compounds are administered subcutaneously. Compounds with molecular weights of 40,000 or more are effectively maintained in the lymphatic system. Further, because the lymph lacks esterases present in plasma that might release drugs from esterified linkages, the favorable pH of the lymph (which is identical to that of plasma) permits release of the active drug from the conjugate. Thus, the compounds of the invention effectively release drug into the lymph when delivery to the lymph is desired, as would be the case, for example, with respect to lymphomas.

The present invention provides conjugates of drugs with macromolecular carriers comprising cleavable linkers that allow for subsequent release of the drugs at controlled rates under physiological conditions, as well as the cleavable linker reagents, linker-drug compounds comprising the cleavable linkers, macromolecular carriers comprising the cleavable linker reagents, and methods for the preparation and use of the above.

The compounds of the invention have the formula (V) which encompasses the drug conjugate and its precursors and further can be used to explain the invention.

In formula (V):

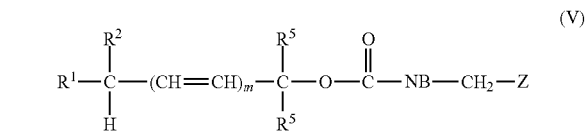

the $R^1$ and/or $R^2$ groups activate the adjacent C—H for beta-elimination under physiological conditions. As used herein, the term "beta-elimination under physiological conditions" refers to a chemical transformation wherein a molecule of the invention is transformed into an alkene moiety and a carbamic acid according to the illustrative scheme

Figure 1:
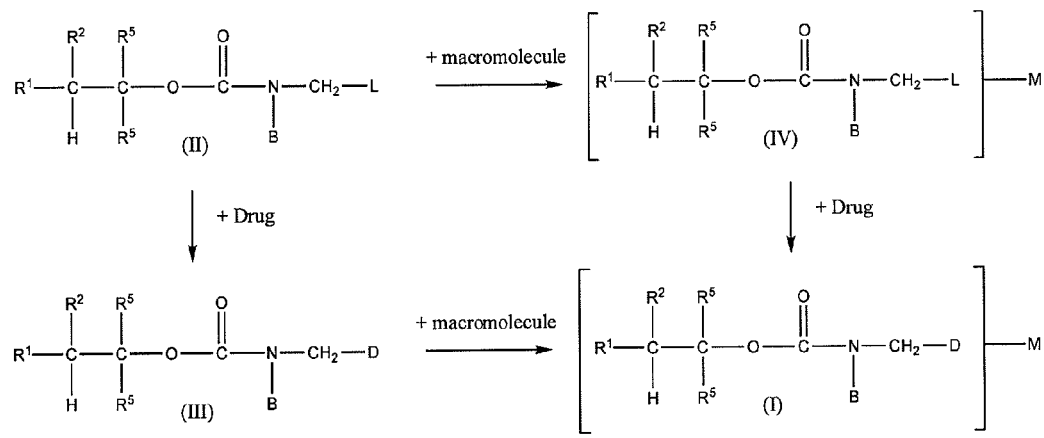
FIG. 1 illustrates the relationships between the molecules of the invention. Reaction of a cleavable linker reagent molecule of formula (II) with a drug via O, S, or non-basic N yields a linker-drug compound of formula (III). Similarly, reaction of a macromolecule-linker reagent conjugate of formula (IV) with a drug via O, S, or non-basic N yields a macromolecule-linker-drug conjugate of formula (I). Conjugation of a linker reagent molecule of formula (II) with a macromolecule provides a macromolecule-linker reagent conjugate of formula (IV). Similarly, conjugation of a linker-drug compound of formula (III) with a macromolecule provides a macromolecule-linker-drug conjugate of formula (I).
Figure 2:
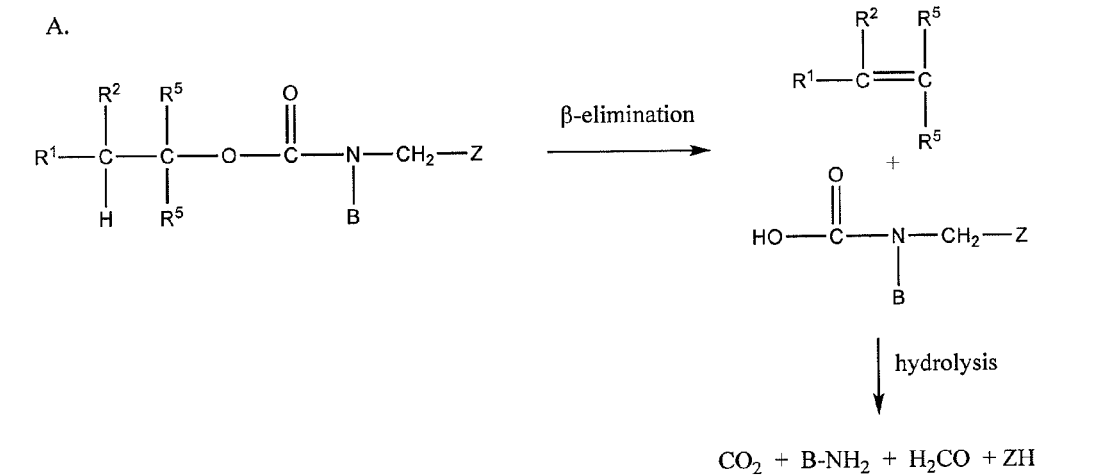
FIG. 2. Panel A illustrates the general scheme of β-elimination-triggered release of drugs from compounds of the invention. Cleavage by β-elimination provides an unstable carbamic acid, which decomposes by loss of $CO_2$ to provide an unstable hemiaminal, which further decomposes to yield B—$NH_2$, $H_2CO$, and free drug ZH. The rate of release of free ZH depends upon the rate of β-elimination, which in turn depends primarily upon the activating groups $R^1$ and $R^2$. Panel B illustrates decomposition of compounds of the invention via E1-elimination. Cleavage of the C—Z bond using the lone pair of the carbamate nitrogen provides free ZH and an unstable iminium ion, which hydrolyzes to provide the carbamate and formaldehyde. The rate of release of free ZH depends upon the activity of the carbamate N lone pair, which in turn is dependent upon the B group. In general, electron-withdrawing and conjugating B groups will favor β-elimination over E1-elimination.
Figure 2:
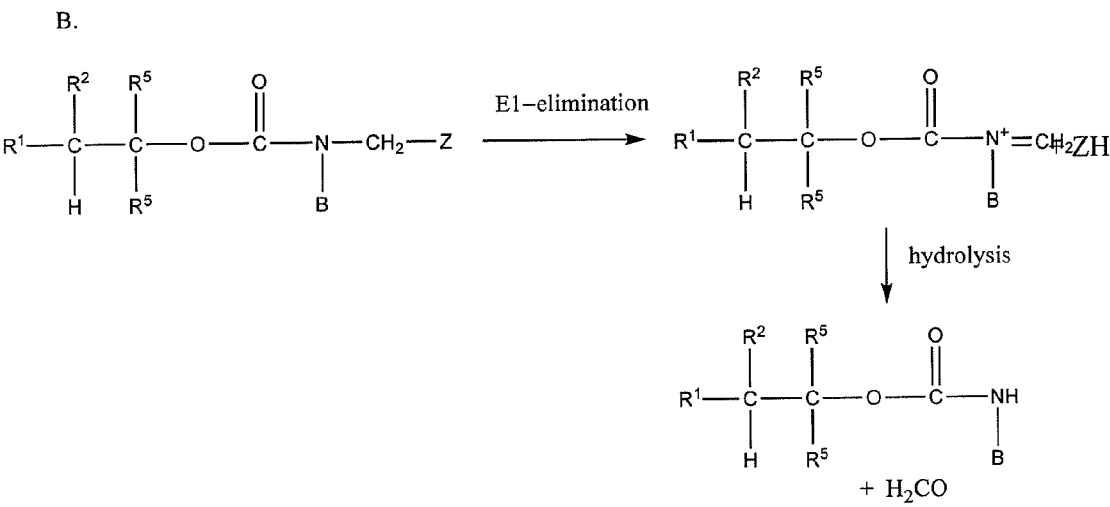

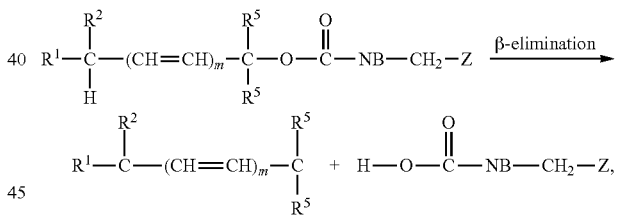

taking place under conditions typical of those of biological systems, for example a pH of between 6 and 8 and a temperature of between 25 and 40° C., at a rate such that the half-life of the reaction is between 1 and 10,000 hours, or between 1 and 5,000 hours, or between 1 and 1,000 hours or between 1 and 100 hours or between 1 and 10 hours. The product carbamic acids are typically highly unstable, and further decompose to release $CO_2$, B—$NH_2$, $H_2C=O$, and Z—H. One possible pathway for this decomposition is illustrated in FIG. 2A and shown in further detail as follows:

(1) HO—(C=O)—N(B)—$CH_2$—Z→$CO_2$+B—NH—$CH_2$—Z (an unstable formaldehyde animal)

(2) B—NH—$CH_2$—Z→B—N=CH+ZH (imine formation)

(3) B—N=CH+$H_2$O→B—NH—$CH_2$—OH (addition of water to the imine to form hemiaminal)

(4) B—$NH_2$+O'$CH_2$ (breakdown of hemiaminal to formaldehyde+amine.)

One of skill in the art will recognize that the various intermediates of the beta-elimination and subsequent decomposition reactions (1)-(4) shown above may be transient and therefore may not be detectable under physiological or other chemical reaction conditions.

The nature of the activating $R^1$ and/or $R^2$ groups is set forth above and substantially controls the rate of the elimination reaction. The $R^1$ and/or $R^2$ groups thus act as one or more trigger groups by determining the acidity of the adjacent C—H. Selection of suitable $R^1$ and/or $R^2$ trigger groups provides a means of controlling the rate of drug release from the compounds of the invention. The degree to which the $R^1$ and/or $R^2$ groups activate the adjacent C—H bond may be expressed by the resulting acidity of the C—H bond; this acidity may in turn be expressed as the $pK_a$ of the C—H bond, wherein a lower $pK_a$ denotes a more acidic, more readily ionized C—H bond. Listings of approximate $pK_a$ values for various groups are common in the art, for example in Bordwell, F. G., "Equilibrium acidities in dimethyl sulfoxide solution," *Accounts of Chemical Research* 21(12): 456-463 (2002) (incorporated herein by reference). Examples of suitably activating groups include, but are not limited to, optionally substituted aryls, optionally substituted heteroaryls, optionally substituted alkenes, optionally substituted alkynes, sulfones, sulfoxides, nitriles, ketones, esters, amides, and nitro groups. When the $R^1$ and/or $R^2$ groups are joined to form a 3-8 membered ring, the ring may form part of a larger cyclic structure, optionally substituted, for example

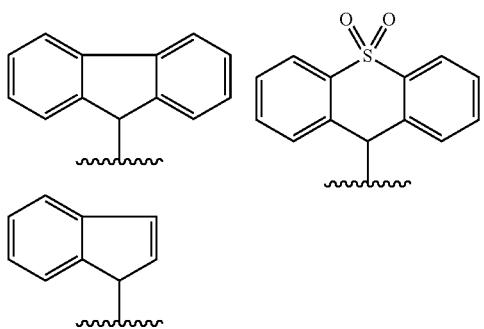

and substituted forms thereof.

Substituents on the $R^1$ and/or $R^2$ groups may optionally be added to provide further control over the acidity of the adjacent C—H, and thus the rate of the beta-elimination reaction. In general, electron-withdrawing substituents will increase the rate of the beta-elimination reaction, while electron-donating substituents will decrease the rate of the beta-elimination reaction. The electronic effect of various substituents is well-known in the art, and may be expressed for example as linear free-energy (Hammett) relationships. For aromatic systems, for example substituted aryl, heteroaryl, arylketone, heteroarylketone, arylsulfone, heteroarylsulfone, arylsulfoxide, and heteroarylsulfoxide groups, the electronic effects of substituents are described by Hammett sigma parameters, with a positive sigma value denoting electron-withdrawing (rate-accelerating relative to an adjacent C—H) and a negative sigma value denoting electron-donating (rate-retarding relative to the C—H) effects. Table 1 provides a listing of Hammett sigma constants for various substituents.

By way of example, where an aryl ring $R^1$ is substituted with an "electron-donating group," the substituent will result in a decrease in the acidity of the adjacent benzylic-type C—H bond. Examples of suitable electron-donating substituents include, but are not limited to, alkyl, alkoxy, alkylthio, silyl amino, alkylamino, and dialkylamino. Substitution of an aryl ring with one or more "electron-withdrawing groups" results in an increase in the acidity of the adjacent benzylic-type C—H bond. Examples of suitable electron-withdrawing substituents include, but are not limited to, halogen, difluoromethyl, trifluoromethyl, nitro, phenyl, alkenyl, cyano, C(=O)—R, wherein R is H, alkyl, alkoxy, or amino, or SOR or $SO_2R$, where R is alkyl, aryl, or heteroaryl. Non-hydrogen electron-donating or electron-withdrawing substituents may be present in multiple positions on rings to which they are bound. While, for convenience, in most examples, only a single occurrence of a non-hydrogen substituent on a single ring is shown, multiple substituents may also be present and are within the scope of the invention. The substituents may be the same or different.

The foregoing is something of an oversimplification, because in some cases, whether a substituent is electron-withdrawing or electron-donating depends on its position in an aromatic ring. This is reflected in the following table of linear free energy (Hammett) relationships, where a positive sigma value denotes electron-withdrawing effect and a negative sigma value indicates an electron-donating effect. As shown in the table, for example, OMe is electron-withdrawing when present in the meta position of a phenyl ring but electron-donating in the para (or ortho) position.

| Selected Hammett sigma constants for aromatic substituents | | |
|---|---|---|
| Substituent | σ(meta) | σ(para) |
| H | 0 | 0 |
| $CH_3$ | −0.07 | −0.17 |
| $CH_3CH_2$ | −0.07 | −0.15 |
| $Me_2CH$ | −0.05 | −0.15 |
| $Me_3C$ | −0.1 | −0.2 |
| $Me_3Si$ | −0.04 | −0.07 |
| $NH_2$ | −0.16 | −0.66 |
| $Me_2N$ | −0.15 | −0.83 |
| OH | +0.12 | −0.37 |
| OMe | +0.12 | −0.27 |
| $OCH_2CH_3$ | +0.10 | −0.24 |
| AcNH | +0.07 | −0.15 |
| Ph | +0.06 | −0.01 |
| $CH_2$=CH | +0.05 | −0.02 |
| HC(=O)NH | +0.19 | 0 |
| F | +0.34 | +0.06 |
| Cl | +0.37 | +0.23 |
| Br | +0.39 | +0.23 |
| I | +0.35 | +0.18 |
| SH | +0.25 | +0.15 |
| MeS | +0.15 | 0 |
| $ClCH_2$ | +0.11 | +0.12 |
| $CF_3$ | +0.43 | +0.54 |
| CN | +0.56 | +0.66 |
| CHO | +0.35 | +0.42 |
| $CH_3C$=O | +0.38 | +0.50 |
| $CO_2H$ | +0.37 | +0.45 |
| NO | +0.62 | +0.91 |
| $NO_2$ | +0.71 | +0.78 |
| $Me_3N^+$ | +0.88 | +0.82 |

The remaining substituents $R^5$ and B have a lesser effect on the rate of beta-elimination, but the nature of B in particular influences the rate of a competing E1 elimination reaction. The nature of the B group influences the stability of the N-methylene-carbamate toward decomposition via E1-type elimination reactions, illustrated in FIG. 2B. B groups that reduce the reactivity of the carbamate N lone pair, for example via extended conjugation and/or electron-withdrawing ability, reduce the rate of competing decomposition by the E1-elimination pathway.

The macromolecules may be coupled to Formula V through additional "connectors." The additional connectors are bifunctional organic compounds. Many such connectors are commercially available, for example from Pierce Chemical Co, Rockford, Ill. Various bifunctional connectors are well known in the art, including dicarboxylic acids or anhydrides, diamines, or heterobifunctional connectors. Examples of heterobifunctional connectors include, for example, those having a succinimidyl ester ("NHS") and an alkyne or cycloalkyne (for example, DBCO—NHS), a maleimide and an NHS, or similar molecules. The selection of the connector will, of course, depend on the nature of the functional groups on the substituents on the macromolecule, the drug, and on the intermediates corresponding to Formulas (I)-(V).

The term "alkyl" includes linear, branched, or cyclic saturated hydrocarbon groups of 1-8 carbons, or in some embodiments 1-6 or 1-4 carbon atoms.

The term "alkoxy" includes alkyl groups bonded to oxygen, including methoxy, ethoxy, isopropoxy, cyclopropoxy, cyclobutoxy, and similar.

The term "alkenyl" includes non-aromatic unsaturated hydrocarbons with carbon-carbon double bonds. By the term "alkenyl ($C_2$)" is meant a mono-, di-, tri-, or tetra-substituted carbon-carbon double bond of any geometric configuration.

The term "alkynyl" includes non-aromatic unsaturated hydrocarbons with carbon-carbon triple bonds. By the term "alkynyl ($C_2$)" is meant a mono- or di-substituted carbon-carbon triple bond.

The term "aryl" includes aromatic hydrocarbon groups of 6-18 carbons, preferably 6-10 carbons, including groups such as phenyl, naphthyl, and anthracenyl. The term "heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

In some instances, alkenyl, alkynyl, aryl or heteroaryl moieties may be coupled to the remainder of the molecule through an alkyl linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" includes bromo, fluoro, chloro and iodo.

The term "heterocyclic ring" refers to a 4-8 membered aromatic or non-aromatic ring comprising 3-7 carbon atoms and at least one N, O, or S atom. Examples include piperidinyl, piperazinyl, tetrahydropyranyl, pyrrolidine, and tetrahydrofuranyl, as well as the exemplary groups provided for the term "heteroaryl" above.

"Maleimido" refers to formula

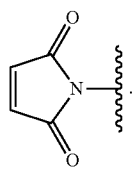

The term "non-basic N" refers to a nitrogen that is part of an NH group in a free drug molecule DH, wherein the NH is characterized by having a pKa less than or equal to approximately 20. In certain embodiments of the invention, the non-basic N is a member of a heteroaryl ring system such as pyrrole, indole, pyrimidine, or purine, a primary or secondary sulfonamide (R—$SO_2$NHR'), a primary or secondary amide (R—CONHR'), or an imide (R—CO—NH—CO—R').

A "nucleofuge" is a leaving group that takes with it the electron pair by which it is bonded. Exemplary nucleofuges are halogen, OH, alkoxy, arylsulfonate, alkylsulfonate, or $R_2S^+$, wherein each R is independently alkyl, aryl, or heteroaryl.

By the term "macromolecule" is meant a molecule or residue of a molecule having a molecular weight between 5,000 and 1,000,000 Daltons, preferably between 10,000 and 500,000 Daltons, and more preferably between 10,000 and 250,000 Daltons. Examples of macromolecules include but are not limited to proteins including antibodies, antibody fragments, and enzymes; polypeptides including poly(amino acid)s such as poly(lysine) and poly(valine) and mixed-sequence polypeptides; synthetic polymers including poly(ethylene glycol) (PEG), poly(ethylene oxide) (PEO), poly(ethylene imine) (PEI), and co-polymers thereof; and polysaccharides such as dextrans. The macromolecules will comprise at least one functional group suitable for conjugation, either natively or after chemical transformation, such as an amine, carboxylic acid, alcohol, thiol, alkyne, azide, or maleimide group as described above. In certain embodiments of the invention, the macromolecule is a polyethylene glycol. The polyethylene glycol may be linear or branched, with one end terminated with a functional group suitable for conjugation and the other end or ends terminated by a capping group (for example, methyl), or may comprise multiple arms each arm terminating in a functional group suitable for conjugation. In preferred embodiments of the invention, the polyethylene glycol is a linear, branched, or multiple-arm polymer having an average molecular weight between 20,000 and 200,000 Daltons, preferably between 20,000 and 100,000 Daltons, and most preferably approximately 40,000 Daltons. Examples of such polyethylene glycols are known in the art and are commercially available, for example from NOF Corporation (Tokyo, Japan).

The terms "protein" and "peptide" are used interchangeably regardless of chain length, and these terms further include pseudopeptides which comprise linkages other than amide linkages, such as $CH_2NH_2$ linkages as well as peptidomimetics.

The terms "nucleic acids" and "oligonucleotides" are also used interchangeably regardless of chain length. The nucleic acids or oligonucleotides may be single-chain or duplexed or may be DNA, RNA, or modified forms thereof with altered linkages, such as phosphodiesters, phosphoramidates, and the like. For both the proteins and nucleic acids useful as drugs in the invention, these terms also include those with side chains not found in nature in the case of proteins as well as pseudopeptide bonds and bases not found in nature in the case of nucleic acids as well as backbone variants such as peptide nucleic acids.

The term "small molecule" in the context of drugs is a term well understood in the art, and is meant to include compounds other than proteins and nucleic acids that either are synthesized or are isolated from nature and in general do not resemble proteins or nucleic acids. Typically, they have molecular weights <1,000, although there is no specific cutoff recognized. Nevertheless, the term is well understood in the fields of pharmacology and medicine.

A wide variety of drugs may be included as the embodiment of D. Each of these drugs will be coupled through a non-basic nitrogen, oxygen or sulfur to the methyl carbamate portion of the compounds of the invention. Thus, suitable drugs will be those that possess a hydroxy, thiol, or non-basic amine to allow for coupling to the linker. Examples of suitable drugs include those for human or veterinary use including, but not limited to, antidiabetic drugs; growth promoters; antibacterials including aminoglycosides, penicillins, cephalosporins, macrolides and peptides, trimethoprim, piromidic acid, and sulfamethazine; analgesic and anti-inflammatory drugs, antiallergic and antiasthmatic drugs, antihypercholesterolemic drugs, beta-adrenergic blockers and antihypertensive drugs, antineoplastic drugs, and antiviral drugs.

Further examples of such drugs include alcohols such as paclitaxel and analogues, epothilones and analogues, camptothecin and analogues such as irinotecan, and nucleosides such as 5-fluorouracil and capecitabine. In another embodiment, the drug is a peptide comprising a serine residue. In another embodiment, the drug is a small molecule comprising an arylol group; examples of such drugs include SN-38, etilefrine, prenalterol, and estradiol. In another embodiment, the drug is a peptide comprising a tyrosine residue. If coupling is through S, the drug may be a small molecule comprising a thiol group. Examples of such drugs include penicillamine, captopril, and enalapril. The drug may be a small molecule comprising a thioaryl or thioheteroaryl group; examples of such drugs include 6-mercaptopurine. If coupling is through a non-basic N, the drug may be a small molecule or peptide comprising a primary or secondary amide (such as a pyroglutamate residue or other amide) or sulfonamide, or a heteroaryl group such as an indole (e.g., tryptophan) or purine. Examples include thyrotropin-releasing hormone, bombesin, luteinizing hormone-releasing hormone, follicle-stimulating releasing hormone, octreotide, 5-fluorouracil and allopurinol.

Examples of nucleic acid-based drugs include the sense strand and antisense strand of any gene from an animal, and particularly from a mammal. Such genes can be those that are already the subjects of antisense DNAs or RNAs, or small interfering RNAs that have been provided with the purpose of treating various diseases, for example genes for protein kinase C-alpha, BCL-2, ICAM-1, tumor necrosis factor alpha and the like.

In particular embodiments, the drug is SN-38 (7-ethyl-10-hydroxycamptothecin).

The term "precursor" refers to a compound similar to formula (I), but wherein rather than the macromolecule, the relevant substituent $R^1$, $R^2$, $R^5$ or B is furnished with a functional group or a linker that can provide coupling, and/or wherein D is replaced by a nucleofuge. Thus, this category of compounds has formulas (II), (III) and (IV).

While typically, the active form of the drug is directly released from the conjugates of the invention, in some cases, it is possible to release the active drug in the form of a prodrug thereof.

To avoid misunderstanding, the "drug conjugates" described herein include conjugates both of drugs and prodrugs.

As noted above, in formula (V), Z is the residue of a drug or prodrug coupled through O, S, or N, or comprises a nucleofuge that allows for connection to a drug through O, S, or non-basic N. When Z is a nucleofuge that allows for connection to a drug through O, S, or non-basic N, Z may be halogen, OH, alkoxy, arylsulfonate, alkylsulfonate, or $R_2S^+$, wherein each R is independently alkyl, aryl, or heteroaryl. In one specific embodiment, Z is halogen or $R_2S^+$. In another embodiment, Z is chloro or methoxy. Likewise, L in formula (II) and formula (IV) may be halogen, OH, alkoxy, arylsulfonate, alkylsulfonate, or $R_2S^+$, wherein each R is independently alkyl, aryl, or heteroaryl, and in specific embodiments, L is chloro or methoxy.

Exemplary Substituents

Because the groups $R^1$, $R^2$, $R^5$, and B are shared by all of the compounds of the invention that define these groups, the various embodiments of these groups as presented in the alternative set forth below are common to all of them. When any group may itself be optionally substituted, the substitution on any ring system may be alkyl, alkenyl, alkynyl, or an additional ring, each optionally substituted. Optional substituents on any group, including the above, include halo, nitro, cyano, OR, SR, $NR_2$, OCOR, NRCOR, COOR, $CONR_2$, SOR, $SO_2R$, $SONR_2$, $SO_2NR_2$, wherein each R is independently alkyl, alkenyl, alkynyl, aryl or heteroaryl, or two R groups taken together with the atoms to which they are attached form a ring.

Compounds of the invention contain a linkage to a macromolecule via one of $R^1$, $R^2$, $R^5$, and B (formula (V), (I), and (IV)), or one of $R^1$, $R^2$, $R^5$, and B comprises a functional group that allows for connection to a macromolecule (formulas (V), (II), and (III)). Suitable functional groups that allow for connection to a macromolecule include amino, azido, hydroxy, carboxylic acid, alkynyl, thiol, maleimido, furan, cyclopentadiene, 1,3-diene, or 1,3-dicarbonyl groups, or protected variants thereof. Substituents that comprise a reactive functional group include alkyl, aryl, arylalkyl, heteroaryl, heteroalkyl, or heteroarylalkyl group, substituted with a reactive chemical moiety. Thus, at least one of the $R^1$, $R^2$, $R^5$, and B groups comprises a macromolecule or comprises one or more amino, azido, hydroxy, carboxylic acid, alkynyl, thiol, maleimido, furan, cyclopentadiene, 1,3-diene, or 1,3-dicarbonyl groups, or protected variants thereof. In some embodiments, $R^1$ is coupled to a macromolecule or comprises a functional group allowing for connection to a macromolecule. In some embodiments, $R^5$ is coupled to a macromolecule or comprises a functional group allowing for connection to a macromolecule.

As noted above, in the compounds of the invention, $R^1$ and $R^2$ together exert the most control over the release rate for the drug, though $R^5$ and m have some impact as well. In some instances, one of $R^1$ and $R^2$ is hydrogen or is alkyl, arylalkyl or heteroarylalkyl and the other comprises one of the remaining embodiments set forth hereinabove. In other instances, neither of $R^1$ and $R^2$ is hydrogen or is alkyl, arylalkyl or heteroarylalkyl.

For example, $R^1$ may be H and $R^2$ optionally substituted phenyl or both $R^1$ and $R^2$ may be optionally substituted phenyl. The substitutions on the phenyl rings may be at 1-5 positions but preferably 3 or less. If both $R^1$ and $R^2$ are optionally substituted phenyl, they need not be substituted identically, or may be identically substituted. Suitable substituents include alkoxy, halo, nitro, cyano and the like, for example as given in Table 1 above.

In other embodiments, one or both of $R^1$ and $R^2$ is $R^6S—$, $R^6S(O)—$, or $R^6S(O)_2—$, wherein $R^6$ is alkyl, substituted alkyl, dialkylamino, alkylarylamino, diarylamino, an N-linked heterocyclic ring, aryl, substituted aryl, heteroaryl, or substituted heteroaryl. The remaining member of $R^1$ and $R^2$ may then be H, for example, or any of the alternative embodiments set forth above. In particular embodiments, one of $R^1$ and $R^2$ is $R^6S(O)_2—$, wherein $R^6$ is methyl, morpholino, unsubstituted phenyl, or phenyl substituted with one or more halo, methyl, methoxy, or trifluoromethyl groups, and the other of $R^1$ and $R^2$ is H. In further embodiments, one of $R^1$ and $R^2$ is phenylsulfonyl, 4-(trifluoromethyl)phenylsulfonyl, 4-chlorophenylsulfonyl, 4-methylphenylsulfonyl, 4-methoxyphenylsulfonyl, 2,4,6-trimethylphenylsulfonyl, morpholinosulfonyl, or methanesulfonyl, and the other of $R^1$ and $R^2$ is H.

In other instances, one or both of $R^1$ and $R^2$ may be cyano and the other optionally selected from H and the permissible substituents set forth above, in particular phenyl optionally substituted at one or more positions, for example, with halo, CN, $NO_2$, methoxy and the like, and optionally further comprising a functional group allowing for connection to a macromolecule. In further embodiments, one of $R^1$ and $R^2$ is cyano and the other is H.

In another set of instances, one or both of $R^1$ and $R^2$ is optionally substituted benzoyl and the other is hydrogen or any of the other suitable choices, such as optionally substituted phenyl. In further embodiments, one of $R^1$ and $R^2$ is aminocarbonyl, such as N,N-dialkylaminocarbonyl, or morpholinocarbonyl, and the other is H.

In additional embodiments, one of $R^1$ and $R^2$ is any one of the particular embodiments described above, further comprising a macromolecule or a functional group allowing for connection to a macromolecule, and the other of $R^1$ and $R^2$ is H.

When $R^1$ and $R^2$ are joined to form cyclic structures, this includes groups wherein the $R^1$—CH—$R^2$ moiety forms a substructure such as, for example,

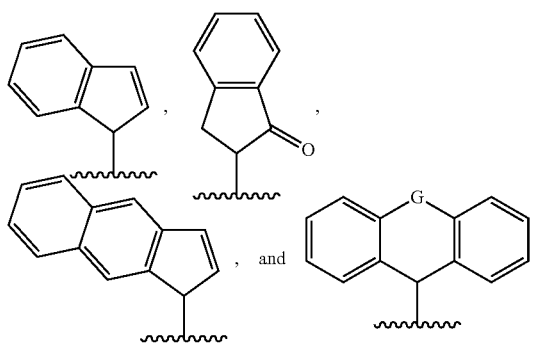

and forms thereof optionally substituted with electron-withdrawing and/or electron-donating groups as described above, wherein G is a bond (e.g., 9-fluorenyl), C=O, SO, $SO_2$, $CA_2$, or $CA_2CA_2$ wherein each A independently is H or Cl.

In further embodiments, $R^1$ and $R^2$ taken together with the CH to which they are attached form unsubstituted fluorenyl or fluorenyl further comprising a macromolecule or a functional group allowing for connection to a macromolecule. In certain embodiments, $R^1$ and $R^2$ taken together with the CH to which they are attached form fluorenyl or fluorenyl substituted with an alkyl azide, in particular (azido-N-methyl$(CH_2)_{3-6}$alkylamido)methyl.

Each $R^5$ is independently H, or is alkyl, alkenylalkyl, alkynylalkyl, aryl, arylalkyl, heteroaryl or heteroarylalkyl, each optionally substituted. In certain embodiments, each $R^5$ is H. In other embodiments, one of $R^5$ is H and the other is substituted alkyl or substituted phenyl. In still other embodiments, one of $R^5$ is H and the other comprises an azidoalkyl group. In still other embodiments, one of $R^5$ is H and the other is azido-$(CH_2)_{3-6}$alkyl, monoalkylamino-$(CH_2)_{3-6}$alkyl, $N_3(CH_2)_{3-6}N(Me)CO(CH_2)_{3-6}$—, or —$(CH_2)_{3-6}$—$CO_2H$, or a protected variant thereof. In additional embodiments, one of $R^5$ is any one of the particular embodiments described above, further comprising a macromolecule or a functional group allowing for connection to a macromolecule, and the other $R^5$ is H.

The B group may be alkyl, aryl, arylalkyl, heteroaryl, or heteroarylalkyl, each optionally substituted. In preferred embodiments of the invention, B is optionally substituted aryl, or optionally substituted heteroaryl. In certain embodiments of the invention, B is aryl or heteroaryl, each substituted with at least one group having a positive Hammett sigma constant (Table 1). In one particular embodiment of the invention, B is phenyl or phenyl substituted with alkoxycarbonyl, carboxamido, sulfonamido, CN, $NO_2$, or Br. In further embodiments, B is unsubstituted phenyl. In still further embodiments, B is unsubstituted phenyl or phenyl substituted with diethylaminocarbonyl, morpholinocarbonyl, or morpholinosulfonyl. In still further embodiments, B is phenyl, propargyl, 4-bromophenyl, 4-ethoxycarbonylphenyl, propyl, 4-(N,N-diethylcarboxamido)phenyl, 4-morpholinocarbonylphenyl, or 4-morpholinosulfonylphenyl. In still further embodiments, B is phenyl, 4-(N,N-diethylcarboxamido)phenyl, 4-morpholinocarbonylphenyl, or 4-morpholinosulfonylphenyl. In additional embodiments, B is any one of the particular embodiments described above, further comprising a macromolecule or a functional group allowing for connection to a macromolecule.

In certain embodiments, m is 0.

In other embodiments, the present invention contemplates compounds of Formula (X):

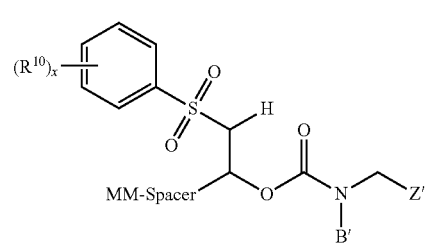

(X)

wherein
x is 0, 1, 2, or 3;
each $R^{10}$ is independently methyl, trifluoromethyl, methoxy, or halo;
B' is phenyl, optionally substituted with alkoxycarbonyl, carboxamido, sulfonamido, CN, $NO_2$, or halo;
Z' is a residue of a drug or prodrug coupled through O, S, or non-basic N or is a nucleofuge which permits such coupling;
Spacer is linker comprising an alkyl, heteroalkyl, aryl, or aralkyl group, each optionally substituted; and
MM is a macromolecule or is a functional group allowing for connection to a macromolecule.

In other embodiments, the present invention contemplates compounds of Formula (XX):

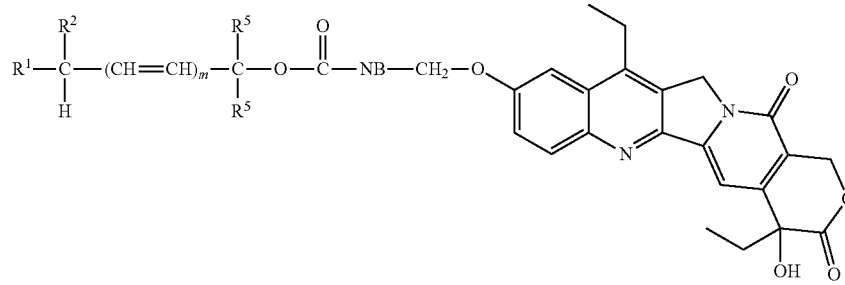

(XX)

wherein $R^1$, $R^2$, $R^5$, m and B are as defined above for formula (V). In further embodiments of formula (XX), m is 0. In still further embodiments of formula (XX), m is 0; $R^1$ is phenylsulfonyl, substituted phenylsulfonyl, methanesulfonyl, $(R^9)_2$N—$SO_2$, wherein $R^9$ is defined as for formula (V), or CN; $R^2$ is H; one $R^5$ is $N_3(CH_2)_5$ and the other $R^5$ is H; and B is phenyl or substituted phenyl. In other embodiments, m is 0; $R^1$ is phenylsulfonyl, substituted phenylsulfonyl, methanesulfonyl, $(R^9)_2$N—$SO_2$, or CN; $R^2$ is H; one $R^5$ is optionally substituted alkyl and the other $R^5$ is H; and B is phenyl or substituted phenyl, and wherein one of $R^1$, $R^5$, and B further comprises a connection to a macromolecule. In still further embodiments of formula (XX), the macromolecule is a linear, branched, or multi-arm polyethylene glycol. In still further embodiments of formula (XX), m is 0; $R^1$ is phenylsulfonyl, substituted phenylsulfonyl, methanesulfonyl, $(R^9)_2$N—$SO_2$, or CN; $R^2$ is H; one $R^5$ is substituted alkyl further connected to a polyethylene glycol, and the other $R^5$ is H; and B is substituted phenyl.

Preparation

In another aspect, the present invention provides methods for preparing compounds of formula (V). One of skill in the art will recognize that compounds of formulae (I), (II), (III), (IV), and (X) are subsets of the compounds of formula (V).

Preparation of Compounds of Formula (II)

Figure 5:
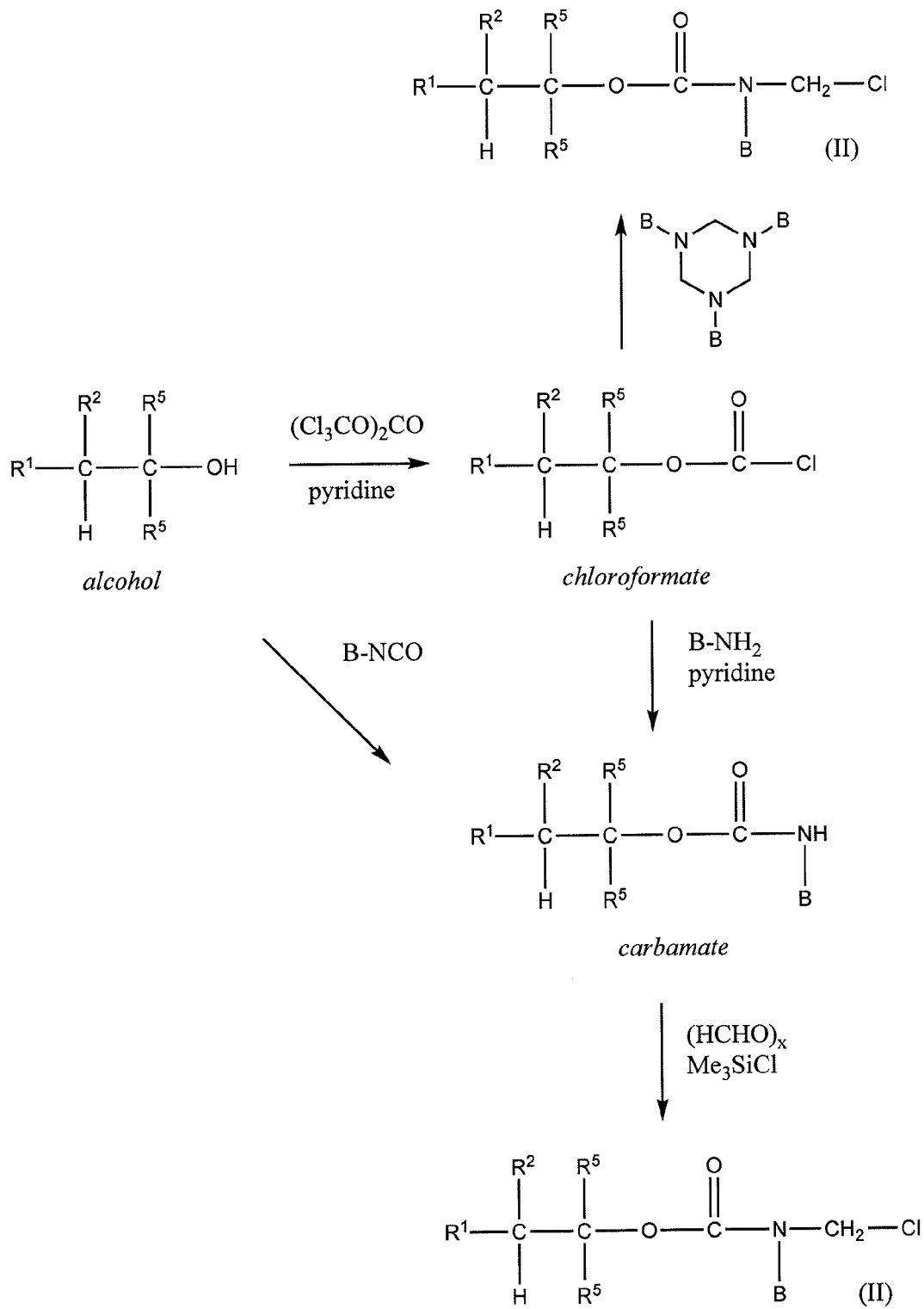
FIG. 5 shows general methods for conversion of alcohols into intermediates and compounds of formula (II), as described in the Specification.

Methods for preparing linker compounds of formula (II) are analogous to methods known in the art for the preparation of N-hydroxymethyl-, N-alkoxymethyl-, and N-halomethyl-amides, or for the preparation of simple N-halomethyl-, N-alkoxymethyl, or N-thiomethyl-carbamates (Majumdar & Sloan, *Bioorganic & Medicinal Chemistry Letters* (2007) 17:1447-1450, incorporated herein by reference), and are illustrated in FIG. 5.

Figure 6:
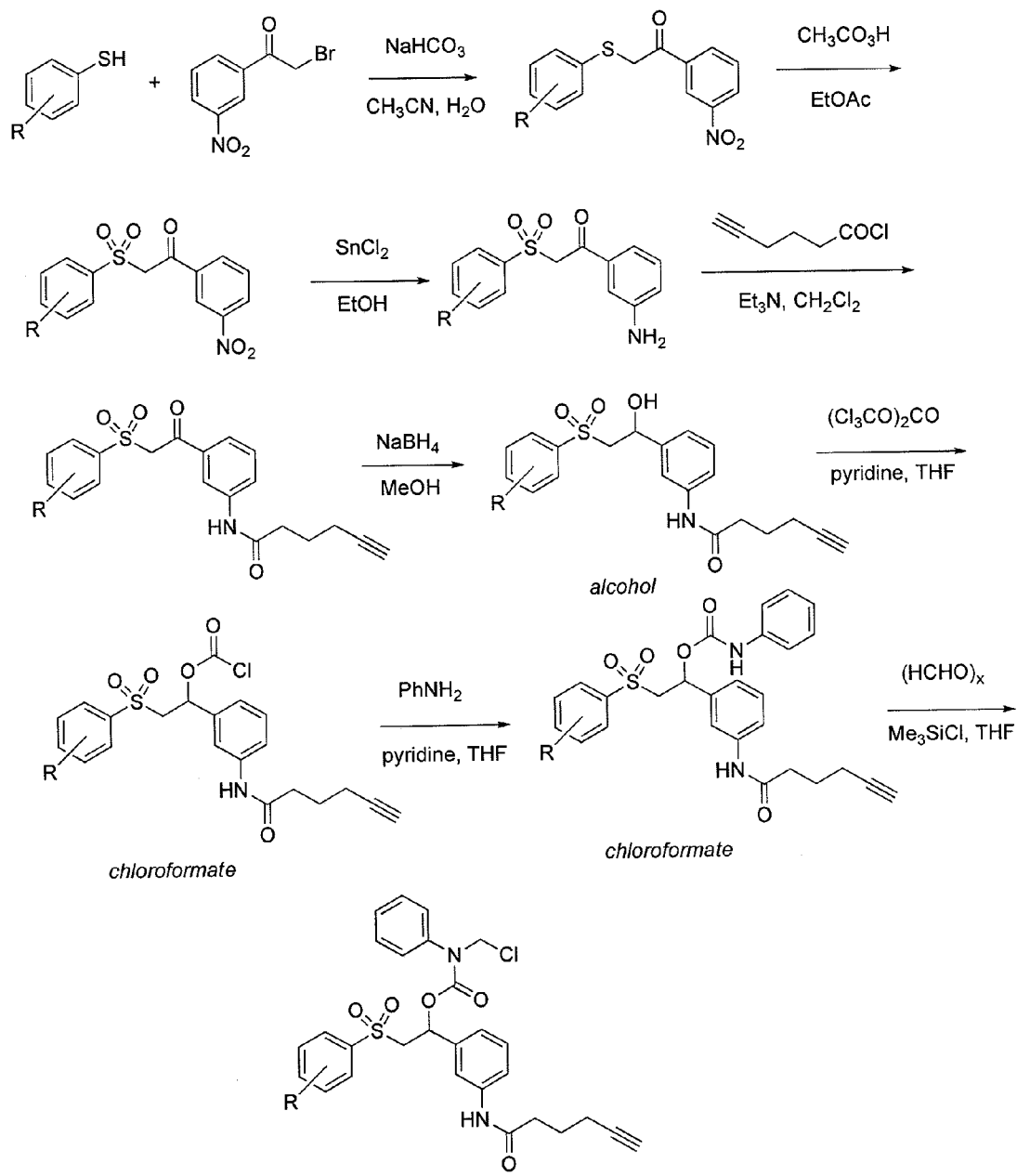
FIG. 6 shows one method for the preparation of compounds of formula (II) wherein $R^1$ is arylsulfonyl, $R^2$ is H, $R^5$ is H and 3-(5-hexynoylamido)phenyl, B is phenyl, and L is Cl.
Figure 7:
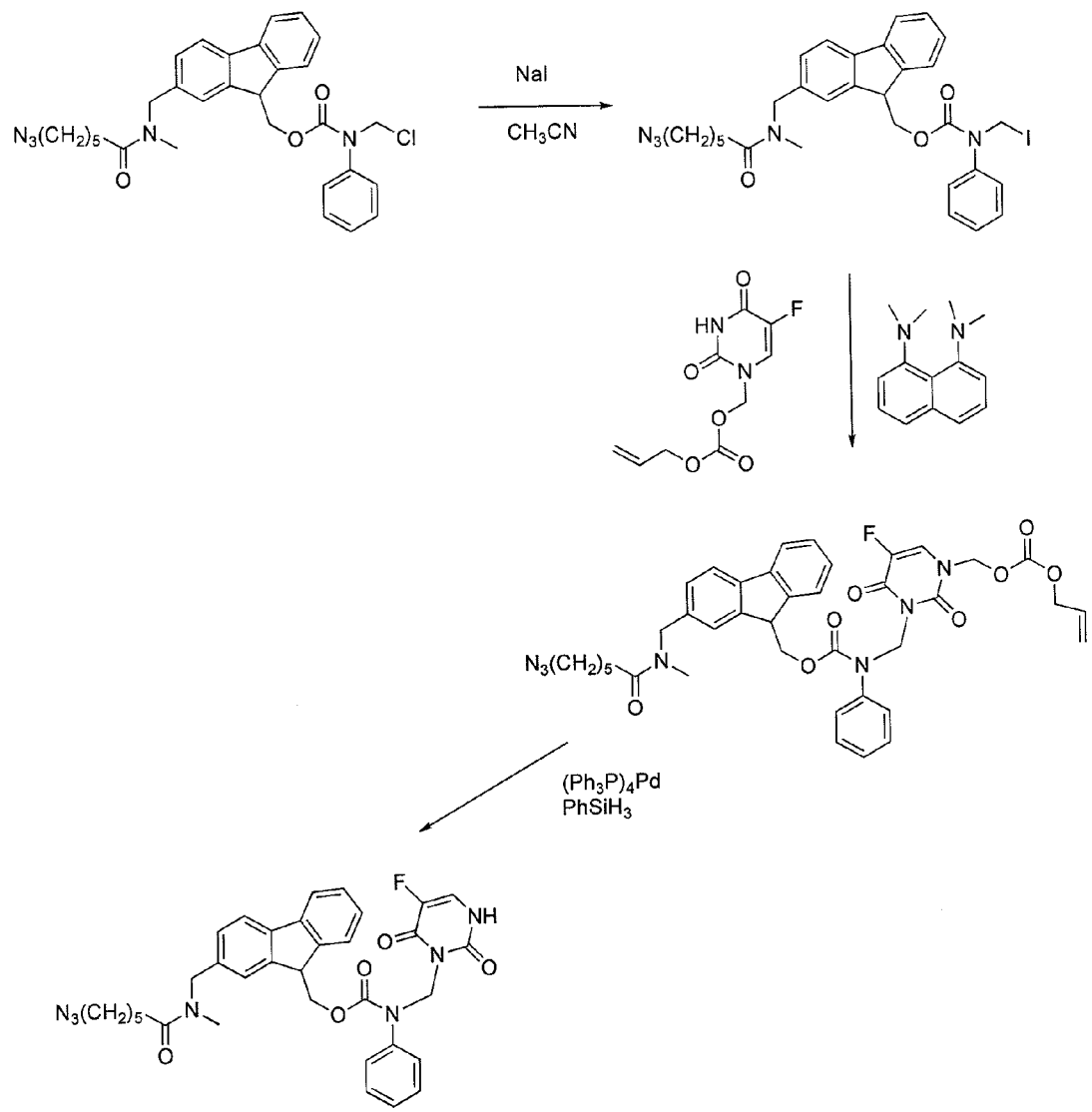
FIG. 7 shows one method for preparing a compound of formula (III) wherein D is connected via N (DH is 5-fluorouracil). This figure also illustrates a method for preparing a compound of formula (II) wherein L is I.

Compounds of formula (II) are prepared from alcohols $R^1R^2C$—$(C=C)_mC(R^5)_2OH$ (FIG. 5 and formula (A), below), and analogs where m=1. Synthesis of such alcohols is described, for example, in PCT patent application PCT/US2009/048943, published as WO2009/158668 A1 (incorporated herein by reference). Examples are given in FIG. 6 and in the working examples provided below.

Alcohols $R^1R^2C$—$(C=C)_mC(R^5)_2OH$ wherein m is 0 (formula (A)) may be prepared by the addition of a carbanion $R^1R^2CH^-$ formed by reacting $R^1R^2CH_2$ with a strong base, for example butyllithium, NaH, lithium diisopropylamide, lithium bis(trimethylsilylamide), or similar with a molecule to produce a compound of formula (A)

(A)

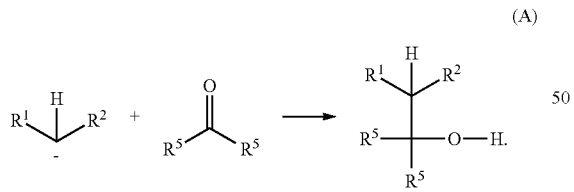

Alternatively, compounds of formula (A) wherein m is 0 and one $R^5$ is H may be prepared by a two-step process. In the first step, the addition of a carbanion $R^1R^2CH^-$, formed by reacting $R^1R^2CH_2$ with a strong base, with an ester $R^5$—C(=O)OR*, wherein R* is lower alkyl, produces an intermediate ketone $R^1R^2CH$—$CR^5$=O, which may in the second step be reacted with a suitable reducing agent, for example $NaBH_4$ or $NaBH_3CN$, to provide the compound of formula (A) wherein one $R^5$ is H.

For example, when $R^1R^2CH_2$ is fluorene, this is reacted with a strong base, for example, to form a fluorenyl carbanion, which is then reacted with $R^5_2$—CO, the reaction is as follows:

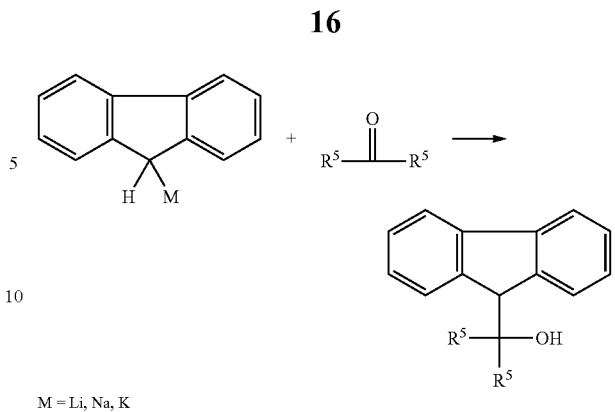

M = Li, Na, K

Alcohols $R^1R^2C$—$(C=C)_mC(R^5)_2OH$ wherein m is 1 and both $R^5$ are H may be prepared by addition of the carbanion derived by lithiation of $R^1R^2CH_2$, for example using a strong base such as NaH, butyllithium, lithium bis(trimethyl-silyla-mide), or similar, to an unsaturated compound such as methyl 3-(dimethylamino)-acrylate to provide an intermediate ester, which may be reduced, either via one step or through multiple steps, to the corresponding unsaturated alcohol:

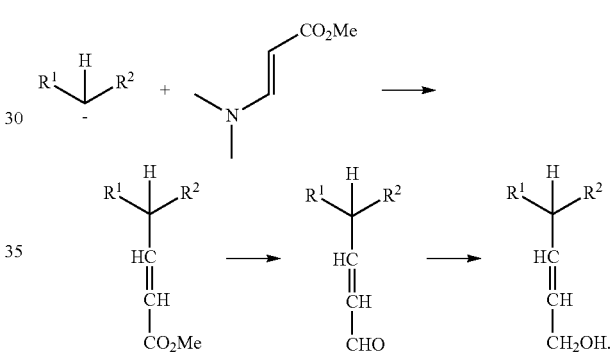

Reaction of the unsaturated aldehyde shown above with a substituted or unsubstituted arylboronic acid, aryl-B(OH)$_2$, in the presence of a palladium catalyst, for example as described in *Org. Lett.* (2005) 7:4153-5, provides a compound wherein m is 1, one $R^5$ is substituted aryl, and one $R^5$ is H.

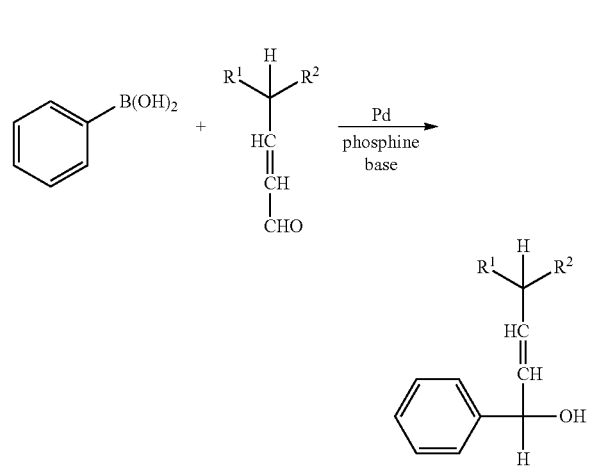

Alternatively, reaction of the unsaturated aldehyde shown above with an alkylborane according to the method of Soderquist provides compounds wherein one $R^5$ is H and the other is —$CH_2CH$=$CH_2$ or —$CH_2CCH$. See Burgos, C. H., et al., *J. Am. Chem. Soc.* (2005) 127:8044.

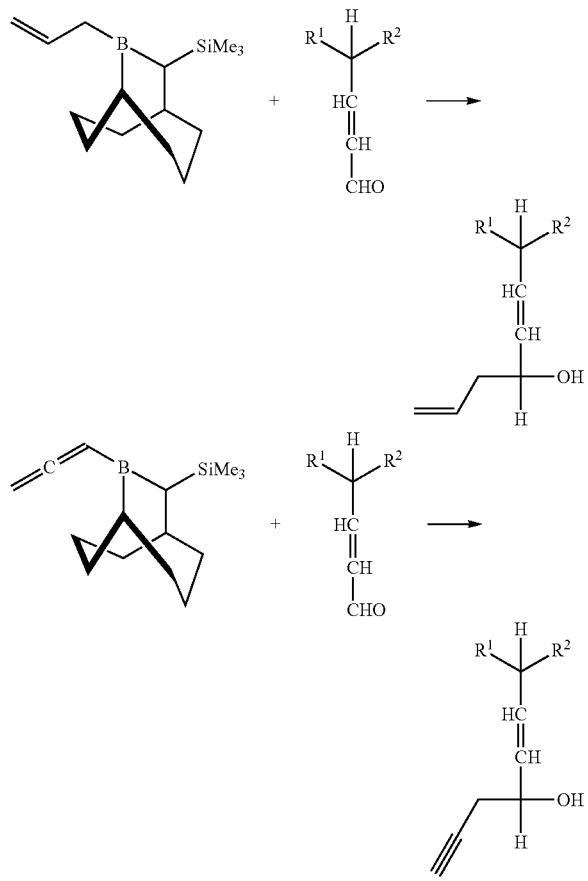

The alcohols $R^1R^2C$—$(C$=$C)_mC(R^5)_2OH$ are then converted to carbamates, $R^1R^2C$—$(C$=$C)_mC(R^5)_2OC(O)NHB$, by methods known in the art, for example, by: 1) activating the alcohol to a chloroformate (with phosgene or a phosgene equivalent such as triphosgene and pyridine), and reacting the chloroformate with B—$NH_2$ in the presence of a mild base such as pyridine or $NaHCO_3$; or 2) reaction of an alcohol with an isocyanate (FIG. 5). A carbamate, $R^1R^2C$—$(C$=$C)_mC(R^5)_2OC(O)NHB$, is then reacted with paraformaldehyde in the presence of a nucleofuge donor L* to give a compound of formula (II). In a specific embodiment, L* is a chloride donor such as $Me_3SiCl$ or HCl, yielding a compound of formula (II) wherein L is Cl.

In another embodiment, a linker compound of formula (II) wherein L is Cl is prepared by reaction of a chloroformate with a hexahydrotriazine derivative (B—N—$CH_2)_3$ (FIG. 5). Reactions may be neat or run in the presence of an inert solvent such as tetrahydrofuran, dichloromethane, ethyl acetate, or dioxane, at temperatures between 0° C. and 100° C., typically at or near the boiling point of the solvent.

Coupling of Macromolecules to Compounds of Formula (II) or (III)

The $R^1$, $R^2$, $R^5$ or B groups in formulas (II) and (III) provide a means of attachment to a macromolecule. Methods for conjugation to macromolecules are generally known in the art.

In cases where the functional group on the $R^1$, $R^2$, $R^5$ or B groups which allows for connection to the macromolecule is present in protected form, the linker-drug compound of formula (II) or (III) is first submitted to conditions under which the protecting group is removed. Thus, when the protecting group is acid-cleavable, such as for 'butyl esters ethers or thioethers, or for 'BOC carbamates, the linker-drug of formula (II) or (III) is first treated with trifluoroacetic acid for sufficient time to remove the protecting group. When the protecting group is removable by reduction, such as allyl ethers or esters, or Alloc carbamates, the linker-drug of formula (II) or (III) is first treated with a mild reducing agent such as phenylsilane in the presence of a palladium(0) catalyst, for example terakis(triphenylphosphine)palladium. When the protecting group is a silyl protecting group, removal to reveal a free hydroxy group may be achieved by treatment with mild acid or with fluoride ion. Conjugation is then performed using methods known in the art.

In one exemplary method, an amide linkage is formed between an amino group and a carboxylic acid group; thus, a linker comprising an amino group can be conjugated to a macromolecule comprising a carboxylic acid group, or a linker comprising a carboxylic acid group can be conjugated to a macromolecule comprising an amino group. The conjugation may be performed by reacting the linker and macromolecule in the presence of a condensing agent, for example a carbodiimide such as dicyclohexylcarbodiimide (DCC) or 1-(3-dimethylaminopropyl)-3-ethylcarbodiimide (EDCI), a uronium reagent such as O-benzotriazole-N,N,N',N'-tetramethyluronium-hexafluorophosphate (HBTU), or a phosphonium reagent such as benzotriazole-1-yl-oxy-tris-(dimethylamino)phosphonium hexafluorophosphate (BOP). Alternately, the carboxylic acid group may be activated for conjugation in a prior step, for example by conversion to an acid chloride using thionyl chloride or oxalyl chloride, or to an active ester such as a pentafluorophenyl ester using a carbodiimide and pentafluorophenol or an N-hydroxysuccinimidyl ester using a carbodiimide and N-hydroxysuccinimide, and the resulting activated carboxylate may then be reacted with the amine in a second step. The amine and carboxylic acid groups may initially be present in protected form as required for stability and/or compatibility with additional chemical transformations, and deprotected prior to the conjugation step. Amine groups may be protected as carbamates, preferably tert-butoxycarbonyl ('BOC), allyloxycarbonyl (Alloc), or other carbamate groups that may be removed under neutral-to-acidic conditions. Carboxylic acids may be protected as esters that may be removed under neutral-to-acidic conditions, such as tert-butyl ('Bu), trityl ($Ph_3C$), allyl (All), or methoxymethyl (MOM).

In a second exemplary method, a thioether linkage is formed between a thiol group and a maleimide group; thus, a linker comprising thiol group can be conjugated to a macromolecule comprising a maleimide group, or a linker comprising a maleimide group can be conjugated to a macromolecule comprising a thiol group. The thiol group may initially be present in protected form as required for stability and/or compatibility with additional chemical transformations, and deprotected prior to the conjugation step. Suitable protecting groups include those that may be removed under neutral-to-acidic conditions, for example tert-butyl thioethers ('Bu) or trityl thioethers.

In a third exemplary method, a 1,2,3-triazole linkage is formed between an alkyne and an azide group; thus, a linker comprising an alkyne group can be conjugated to a macromolecule comprising an azide group, or a linker comprising an azide group can be conjugated to a macromolecule comprising an alkyne group. The conjugation reactions may be performed under metal catalysis, typically using copper or ruthenium, or may be performed in the absence of catalyst using an activated alkyne such as a cyclo-octyne. Other cycloaddition reactions, for example the Diels-Alder reaction between a 1,3-diene (for example, a cyclopentadiene) and a dienophile (for example, maleimide), may also be used.

In a fourth exemplary method, an enamino-ketone linkage is formed between an amino group and a 1,3-dicarbonyl group; thus, a linker comprising an amino group can be conjugated to a macromolecule comprising a 1,3-dicarbonyl group, or a linker comprising a 1,3-dicarbonyl group can be conjugated to a macromolecule comprising an amine group. In one embodiment, a linker comprising a 1,3-dicarbonyl group is reacted with an antibody such as m38C2 comprising a suitably reactive lysine ε-amino group (Doppalapudi, et al., *Bioorganic & Medicinal Chemistry Letters* (2007) 17:501-506, incorporated herein by reference).

Thus, the $R^1$, $R^2$, $R^5$ or B groups independently may comprise optionally protected amine, optionally protected carboxylic acid, optionally protected thiol, maleimide, alkyne, or azide groups to allow for conjugation with macromolecules. Once conjugated, these groups may independently optionally be substituted by macromolecules connected via carboxylic amide, thioether, or 1,2,3-triazole groups.

Linkage of Compounds of Formula (II) or Formula (IV) to Drug/Prodrug

Compounds of formula (III) or (I) are prepared by reaction of compounds of formula (II) or (IV), respectively, wherein L is a suitable leaving group such as tosylate, alkylsulfonate, halogen or $R^6R^7S^+$, with a drug DH comprising an OH, SH, or non-basic NH group, under anhydrous conditions in the presence of a mild base:

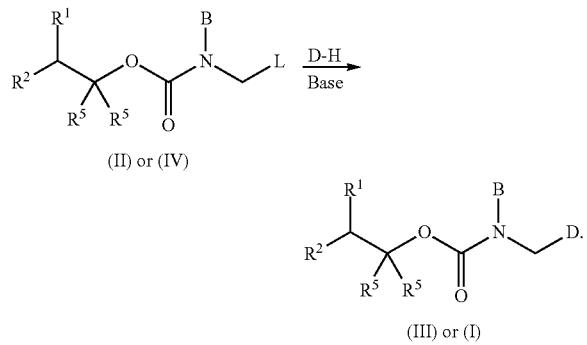

Suitable bases include tertiary amines, such as triethylamine and N,N-diisopropylethylamine, pyridine, or 4-(dimethylamino)pyridine. The reaction mixture may optionally include NaI or a tetraalkylammonium iodide to accelerate the reaction. Suitable solvents include any inert, anhydrous solvent, including tetrahydrofuran, acetonitrile, dimethylformamide, ethyl acetate, dichloromethane, acetone, and chloroform. In some instances, for example when the drug comprises a phenol or non-basic NH, it may be advantageous to pre-form a salt of the drug by reaction with a strong base, for example NaH, lithium bis(trimethylsilylamide), lithium diisopropylamide, or similar.

In one embodiment of the invention, where the drug is a peptide, the terminal amino acid of the peptide may be a pyroglutamyl residue connected to a linker of the invention. Such peptides may be prepared by chemical synthesis of the peptide, wherein the final coupling step uses a linker-pyroglutamate residue. Such linker-pyroglutamate residues can be prepared by alkylation of a salt of a suitable pyroglutamic acid ester, for example allyl pyroglutamate, with a compound (II) or (IV) of the invention.

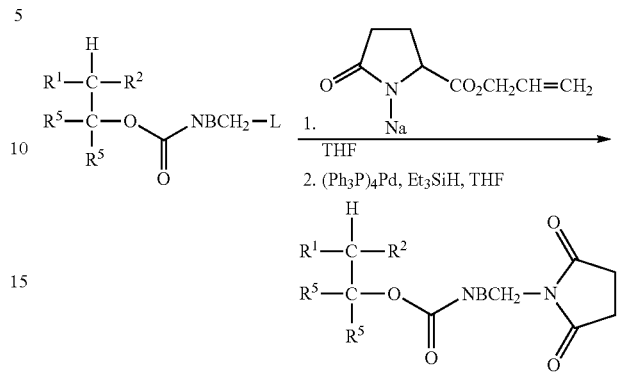

After removal of the ester protecting group, for example using a palladium catalyst in the presence of a reducing agent such as a silane, the linker-pyroglutamate residue can be used in peptide synthesis using standard methods.

Administration and Use

The conjugates of the invention that are designed to release drugs at controllable rates are administered to subjects in a manner similar to medicaments in general. The subjects may be model systems such as mice, rats or rabbits or may be human patients or may be veterinary subjects such as companion animals, livestock, and avian subjects. The conjugates of the invention are typically administered by injection, in general by intravenous injection, but other dosage mechanisms are also within the scope of the invention such as oral administration, administration by suppository, transdermal or transmucosal administration and the like. The dosage levels will depend on the nature of the drug, the condition to be treated, the nature of the subject, and the judgment of the attending professional. The selection of appropriate release rates for a particular drug or protocol are also dependent on these factors. Thus, the use and administration of the compounds of the invention is within the skill of the practitioner. Further, as noted above, the conjugates of the invention are particularly useful and advantageous in treating diseases of the lymph system wherein subcutaneous injection is preferred.

Unless otherwise stated, all references cited herein are incorporated by reference in their entirety. The following examples are intended to illustrate but not to limit the invention.

Example 1

Groups Cleavable by β-Elimination

A series of model linker scaffolds having a range of functional groups as potential $pK_a$ modulators (substituted aromatics, ketones, nitriles, sulfones) were designed, prepared and linked via carbamate bonds to $N_\varepsilon$-2,4-dinitrophenyl-L-lysine ($N_\varepsilon$-DNP-Lys) for evaluation of release rates. DNP-Lys was chosen as the released moiety as it is water soluble and is a strong chromophore to permit HPLC-UV analysis. This experiment demonstrates that the rate of carbamate cleavage is controllable through the choice of particular substituents on the trigger group.

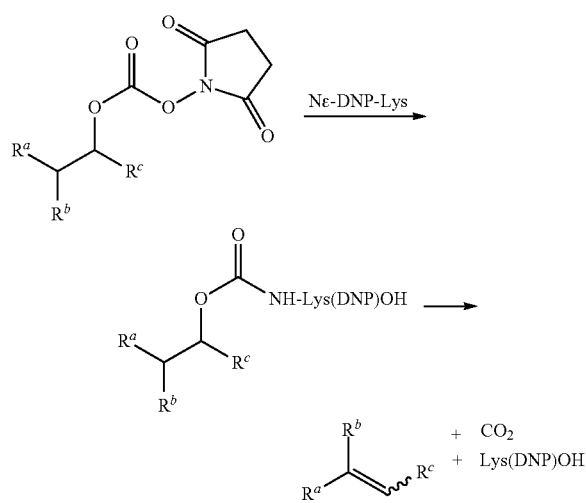

The model DNP-lysine derivatives were prepared as described in copending application Ser. No. 13/696300.

The rates of release of $N_\epsilon$-2,4-dinitrophenyl-L-lysine from these compounds were determined at pH 7.4 or pH 8.3, 37° C., by HPLC analysis. Kinetic analyses of the release reactions were performed by HPLC (C18; linear methanol/water+ 0.5% HOAc gradient) using a UV/vis monitor at 350 nm. The areas under the Lys(DNP) ("P") and starting material ("S") peaks were integrated to determine extent of reaction ("R") as R=P/(S+P). Reaction rates were calculated from the slope the line obtained by linear regression analysis of a plot of ln(1−R) versus time. The $t_{1/2}$ values of β-eliminative cleavage of DNP-Lys carbamates at pH 7.4 and/or 8.3 are shown in Table 2.

TABLE 2

Kinetic data for release of $N_\epsilon$-2,4-dinitrophenyl-L-lysine at 37° C.

| $R^1$ | $R^2$ | $R^5$ | $t_{1/2}$ pH 7.4 | $t_{1/2}$ pH 8.3 |
|---|---|---|---|---|
| 4-MePhSO$_2$ | H | H, H | 56 hrs | — |
| PhSO$_2$ | H | H, H | 30 hrs | — |
| 3-NO$_2$PhSO$_2$ | H | H, H | 2 hrs | — |
| PhSO$_2$ | H | H, Me | 72 hrs | — |
| 4-ClPhSO$_2$ | H | H, Me | 46 hrs | — |
| 4-ClPhSO$_2$ | H | H, 4-OMePh | 18 hrs | — |
| 4-ClPhSO$_2$ | H | H, 4-BrPh | 17 hrs | — |
| 4-ClPhSO$_2$ | H | H, 4-NO$_2$Ph | 2 hrs | — |
| 4-OMePhSO$_2$ | H | H, 3-NO$_2$Ph | 13 hrs | — |
| 4-OMePhSO$_2$ | H | H, 4-NO$_2$Ph | 10 hrs | — |
| CN | H | H, H | — | 160 hrs |
| CN | H | H, Me | — | 320 hrs |
| CN | H | H, Ph | — | 98 hrs |
| CN | H | H, 4-BrPh | 270 hrs | — |
| CN | H | H, 4-OMePh | 22 hrs | — |
| CN | 4-OMePh | H, Me | 125 hrs | — |
| CN | 4-NO$_2$Ph | H, Me | ~80 hrs | — |
| 9-fluorenyl | | H, H | ~1650 hrs | 200 hrs |
| 9-fluorenyl | | H, Me | — | ~1800 hrs |
| 9-fluorenyl | | H, 4-BrPh | — | 285 hrs |

As shown in Table 2, the half-lives for elimination of the carbamate and release of $N_\epsilon$-2,4-dinitrophenyl-L-lysine varied from 2 to >1650 hours at pH 7.4. That cleavage was generated by β-elimination reactions was evidenced by the different half-lives, and the observation that O-benzyl-N—($N_\epsilon$-2,4-dinitrophenyl-L-lysine)-carbamate (which cannot undergo O-alkyl scission) showed no observable release of $N_\epsilon$-2,4-dinitrophenyl-L-lysine (less than the estimated detection limit of 0.25% cleavage) after 5 days at 37° C. and pH 7.4 ($t_{1/2}$>3 yrs).

O-Benzyl-N—($N_e$-2,4-DNP-Lys) carbamate undergoes no detectable hydrolysis in 50% human serum after 1 week at 37° C. This demonstrates the stability of carbamates to serum hydrolases. In general, compared to C—H, a) electron withdrawing groups at the beta position increase the rate; b) alkyl groups at the alpha position increase the rate; and c) aryl moieties at the alpha position decrease the rate.

A good linear free energy relationship was observed for the substituted (phenylsulfonyl)ethyl linkers, allowing estimation of release rates for other substituted linkers in this series based on SAR using Hammett sigma parameters. Thus, substituents can be selected to provide either slower (e.g., 4-OMe, $\sigma_p$=−0.27; 4-OH, $\sigma_p$=−0.37; 4-Me$_2$N, $\sigma_p$=−0.83) or intermediate release rates (e.g., 4-F, $\sigma_p$=+0.06; 4-Cl, $\sigma_p$=+0.23; 3-Br, $\sigma_m$=+0.39; 4-CF$_3$, $\sigma_p$=+0.54).

Example 2

General Preparation of Chloroformates and N-Hydroxysuccinimide Carbonates

Pyridine (0.33 equivalent) is added dropwise to a vigorously stirred solution of the alcohol $R^1R^2C$—$(C≡C)_mC(R^5)_2$OH (1 equivalent) and triphosgene (0.33 equivalent) in anhydrous tetrahydrofuran (2 mL/mmol) cooled on ice. After 1 hr, the mixture is allowed to warm to ambient temperature and kept overnight. The mix is then filtered and concentrated under vacuum on a rotary evaporator. The resulting crude chloroformate $R^1R^2C$—$(C≡C)_mC(R^5)_2$OC(O)Cl is used without further purification.

To prepare N-hydroxysuccinimide carbonates, the crude chloroformate is dissolved in anhydrous tetrahydrofuran (2 mL/mmol) and treated with pyridine (2 equivalents) and N-hydroxysuccinimide (4 equivalents) at ambient temperature for 30 minutes. The mixture is diluted with ethyl acetate, washed successively with 0.1 N HCl, water, and brine, then dried over MgSO$_4$, filtered, and evaporated. The crude carbonates $R^1R^2C$—$(C≡C)_mC(R^5)_2$OC(O)Su are purified by silica gel chromatography (ethyl acetate/hexanes).

Example 3

General Preparation of Carbamates

A solution of the chloroformate of Example 2 (1 equivalent) in acetone (2 mL/mmol) is added dropwise to a vigorously stirred mixture of the amine BNH$_2$ (1 equivalent) and NaHCO$_3$ (2 equivalents) in water (2 mL/mmol). After 30 minutes, carbamates which precipitate as solids are collected by vacuum filtration, washed with water, and dried; carbamates which separate as oils are extracted with ethyl acetate. The extract is dried over MgSO$_4$, filtered, and evaporated to provide the crude carbamate. In either case, the crude carbamate $R^1R^2C$—$(C≡C)_mC(R^5)_2$OC(O)NHB is further purified by column chromatography (SiO$_2$) or by crystallization.

Alternatively, triethylamine (1 equivalent) is added to a mixture of the amine BNH$_2$ (1 equivalent) and the chloroformate (1 equivalent) in an inert anhydrous solvent, for example dichloromethane, tetrahydrofuran, or ethyl acetate. After stirring for 1 h at ambient temperature, the mixture is evaporated to dryness, and the residue is dissolved in ethyl acetate and washed successively with 1 N HCl, water, sat. aq. NaHCO$_3$, and brine, then dried over MgSO$_4$, filtered, and evaporated to provide the crude carbamate, which is purified as described above.

Alternatively, an alcohol R$^1$R$^2$C—(C≡C)$_m$C(R$^5$)$_2$OH is converted to a carbamate without isolation of the intermediate chloroformate. Pyridine (0.33 equivalent) is added dropwise to a vigorously stirred solution of the alcohol (1 equivalent) and triphosgene (0.33 equivalent) in anhydrous tetrahydrofuran (2 mL/mmol) cooled on ice. After 1 hr, the mixture is allowed to warm to ambient temperature and kept overnight. The mixture is cooled on ice, and the amine BNH$_2$ (2 equivalents) is added. The mixture is allowed to warm to ambient temperature and kept overnight. The mixture is then evaporated to dryness, and the residue is dissolved in ethyl acetate and washed successively with 1 N HCl, water, sat. aq. NaHCO$_3$, and brine, then dried over MgSO$_4$, filtered, and evaporated to provide the crude carbamate, which is purified as described above.

Example 4

N-Chloromethylation of Carbamates

A mixture of the carbamate of Example 3 (1 equivalent) and paraformaldehyde (3 equivalents of formaldehyde) in 1:1 tetrahydrofuran/chlorotrimethylsilane (1 mL/mmol) in a sealed screw-cap vial is heated at 55° C. until a clear solution is obtained. The mixture is concentrated under vacuum on a rotary evaporator, and the residue is dissolved in ethyl acetate, filtered, and concentrated again to provide the crude N-chloromethyl carbamate, R$^1$R$^2$C—(C≡C)$_m$C(R$^5$)$_2$OC(O) NBCH$_2$Cl.

Example 5

N-Methoxymethyl Carbamates

A solution of N-chloromethyl carbamate of Example 4 in methanol is allowed to stand at ambient temperature for 1 h, then concentrated to dryness to provide the N-methoxymethyl carbamate, R$^1$R$^2$C—(C≡C)$_m$C(R5)$_2$OC(O) NBCH$_2$OMe.

Example 6

N-Alkoxymethyl Carbamates, N-Phenoxymethyl Carbamates, N-Thiomethyl Carbamates, and N-Thiophenylmethyl Carbamates A solution of an alcohol, phenol, thiol, or thiophenol derived from drug DH (1 equivalent) and the N-chloromethylcarbamate of Example 4 (1 equivalent) in an inert anhydrous solvent, for example tetrahydrofuran, dichloromethane, or ethyl acetate, is treated dropwise with triethylamine (1 equivalent). After 1 hour, the mixture is evaporated to dryness. The crude product is purified by silica gel chromatography.

Example 7

O-(9-Fluorenylmethyl)-N-Propargyl Carbamate

A solution of 9-fluorenylmethoxycarbonyl chloride (2.6 g) in 20 mL of acetone was added slowly to a stirred mixture of propargylamine hydrochloride (0.91 g) and NaHCO$_3$ (2.5 g) in 20 mL of water. After 1 hour, the solid precipitate was collected by vacuum filtration, washed with water, and air dried. Crystallization from ethyl acetate/hexane provided the product.

Example 8

O-(9-Fluorenylmethyl)N-(4-Bromophenyl)Carbamate

Triethylamine (0.7 mL) was added to a stirred mixture of 4-bromoaniline (0.85 g) and 9-fluorenylmethoxycarbonyl chloride (1.3 g) in 25 mL of dichloromethane. The mixture was stirred for 1 h at ambient temperature, then washed with 1 N HCl, water, sat. aq. NaHCO$_3$, and brine. The organic solution was dried over MgSO$_4$, filtered, and evaporated.

Example 9

O-(9-Fluorenylmethyl)N-(4-(Ethoxycarbonyl)Phenyl)Carbamate

Triethylamine (0.7 mL) was added to a stirred mixture of ethyl 4-aminobenzoate (0.85 g) and 9-fluorenylmethoxycarbonyl chloride (1.3 g) in 25 mL of dichloromethane. The mixture was stirred for 1 h at ambient temperature, then washed with 1 N HCl, water, sat. aq. NaHCO$_3$, and brine. The organic solution was dried over MgSO$_4$, filtered, and evaporated.

Example 10

O-(9-Fluorenylmethyl)N-Phenyl N-Methoxymethyl Carbamate

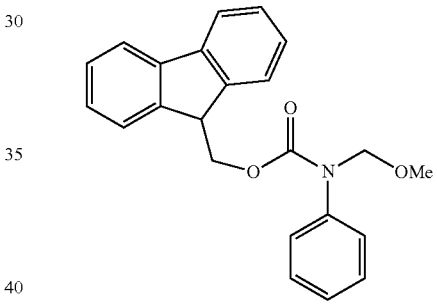

Prepared by dissolving O-(9-fluorenylmethyl)N-phenyl N-chloromethyl carbamate (Example 14) in methanol. 1H-NMR (d6-DMSO) δ 7.86 (2H, d, J=7 Hz), 7.42-7.22 (m, 9H), 7.14 (m, 2H), 4.83 (2H, br s), 4.47 (2H, d, J=6 Hz), 4.18 (1H, m), 3.11 (3H, br s).

Example 11

Conjugation of Hydroxy- and Thiol-Containing Moieties to Linker

This example demonstrates that hydroxy-containing molecules are readily conjugated to the linker moiety.

A. N-(6-(2,4-Dinitrophenylamino)Hexanoyl-L-Serine Allyl Ester

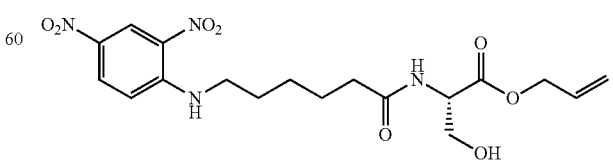

Step 1. N-(tert-butoxycarbonyl)-L-serine allyl ester: To a stirred solution of allyl bromide (2.3 mL, 26.6 mmol) and tricaprymethylammonium chloride (4.00 g, 9.90 mmol) in CH₂Cl₂ (35 mL) was added a solution of N-(tert-butoxycarbonyl)-L-serine (1.03 g, 5.02 mmol) and NaHCO₃ (0.43 g, 5.12 mmol) in water (16 mL). The biphasic reaction mixture was vigorously stirred at room temperature for 48 hours. It was diluted with water (50 mL) and extracted with CH₂Cl₂ (3×50 mL). The combined organic extracts were dried over MgSO₄, filtered, and concentrated under reduced pressure to yield a colorless oil (5.95 g). Purification using a Thomson Instruments Single Step 80 g silica gel cartridge eluting with 60% hexanes/40% ethyl acetate produced LR2-1 (1.01 g, 82%) as a colorless oil. ¹H NMR (DMSO-d6) δ 1.37 (9H, s), 3.63 (2H, m), 4.00 (2H, m), 4.53 (2H, m), 4.89 (1H, t, J=6.2 Hz), 5.18 (1H, dd, J=1.4 Hz, J=10.6 Hz), 5.30 (1H, dd, J=1.6 Hz, J=17.1 Hz), 5.84 (1H, m), 6.98 (1H, d, J=8.2 Hz).

Step 2. A solution of N-(tert-butoxycarbonyl)-L-serine allyl ester (0.175 g, 0.731 mmol) in 4 M hydrogen chloride/dioxane (2 mL) was stirred at ambient temperature for 40 minutes. The reaction mixture was concentrated on a rotary evaporator and the crude HCl salt was taken up in anhydrous tetrahydrofuran (3 mL). To this solution was added N-succinimidyl 6-(2,4-dinitroanilino)hexanoate (0.288 g, 0.791 mmol) and triethylamine (102 mL, 0.731 mmol). The reaction mixture was stirred at room temperature for 30 minutes and the solvent was evaporated. The residue was partitioned between ethyl acetate and water and the phases were separated. The organic phase was washed with saturated NaHCO₃ and saturated NaCl. It was dried over MgSO₄, filtered, and concentrated under reduced pressure to yield the crude product (0.293 g) as a yellow oil. Purification using a Thomson Instruments Single Step 12 g silica gel cartridge eluting with 50% hexanes/50% ethyl acetate followed by ethyl acetate gave the product (0.222 g, 72%) as a yellow oil. ¹H NMR (DMSO-d6) δ 1.32 (2H, m), 1.52-1.64 (4H, m), 2.15 (2H, t, J=7.0 Hz), 3.44 (2H, m), 3.59 (1H, m), 3.66 (1H, m), 4.33 (1H, m), 4.55 (2H, m), 5.02 (1H, t, J=5.5 Hz), 5.17 (1H, m), 5.28 (1H, m), 5.83 (1H, m), 7.21 (1H, d, J=9.5 Hz), 8.12 (1H, d, J=7.9 Hz), 8.23 (1H, dd, J=2.5 Hz, J=9.4 Hz), 8.85 (2H, m).

B. O—(N-((9-Fluorenylmethoxy)Carbonyl)-N-Phenyl)Aminomethyl)N-(6-(2,4-Dinitrophenylamino)Hexanoyl)-Serine Step 1. A solution of N-(6-(2,4-dinitrophenylamino)hexanoyl-L-serine allyl ester (0.050 g, 0.118 mmol), O-(9-fluorenylmethyl)N-phenyl N-chloromethyl carbamate (0.043 g, 0.118 mmol) and triethylamine (16.1 mL, 0.116 mmol) in anhydrous CH₂Cl₂ (2 mL) was heated at reflux for 1 hour. Further aliquots of O-(9-fluorenylmethyl)N-phenyl N-chloromethyl carbamate (0.043 g, 0.118 mmol) and triethylamine (16.1 mL, 0.116 mmol) were added and reflux maintained for 1 hour. The solution was cooled to room temperature, diluted with CH₂Cl₂, washed with saturated NaCl solution, dried over MgSO₄, filtered, and concentrated under reduced pressure. The crude material (0.145 g) was purified using a Thomson Instruments Single Step 12 g silica gel cartridge eluting with 50% hexanes/50% ethyl acetate followed by 30% hexanes/70% ethyl acetate to furnish the intermediate allyl ester (0.030 g, 33%) as a yellow oil. ¹H NMR (DMSO-d6) δ 1.31 (2H, m), 1.52-1.63 (4H, m), 2.15 (2H, t, J=7.3 Hz), 3.41 (2H, m), 3.43-3.70 (2H, br. m), 4.15 (1H, br, m), 4.43-4.54 (5H, br. m), 4.87 (2H, br. m), 5.14 (1H, m), 5.25 (1H, m), 5.79 (1H, m), 7.12-7.38 (12, m), 7.82 (2H, d, J=7.4 Hz), 8.21 (1H, dd, J=2.5 Hz), J=9.5 Hz), 8.25 (1H, d, J=8.0 Hz), 8.84 (2H, m).

Figure 4:
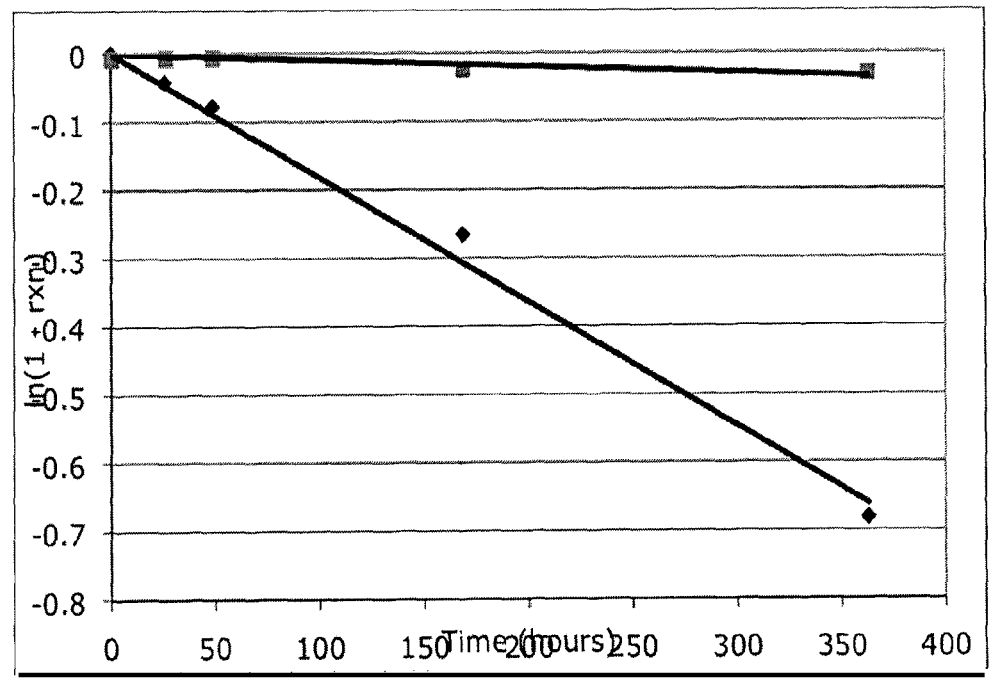
FIG. 4 shows the kinetics of release of N-(6-(2,4-dinitrophenyl)aminohexanoyl)-serine from O—(N-(9-fluorenylmethoxycarbonyl-N-phenyl)aminomethyl)-serine (Example 11B) (diamonds; $T_{1/2}$=400 hours) and O—(N-ethoxycarbonyl-N-phenyl)aminomethyl)-serine (squares; $T_{1/2}$=8,000 hours) in 0.1 M HEPES buffer, 15 mM NaCl, pH 7.40, 37° C.

Step 2. Tetrakis(triphenylphoshine)palladium(0) (0.002 g, 1.7 µmol) was added to a stirred solution of the allyl ester from Step 1 (0.030 g, 40 µmol) and phenylsilane (9.8 mL, 80 µmol) in anhydrous tetrahydrofuran (0.5 mL). The reaction mixture was stirred at ambient temperature for 30 minutes and was then concentrated. Silica gel and CH₂Cl₂ were added and the mixture again concentrated and loaded onto a short silica gel column. The column was eluted with 30% hexanes/70% ethyl acetate followed by ethyl acetate and finally ethyl acetate containing 0.5% acetic acid to generate the carboxylic acid (0.024 g, 86%) as a yellow oil. ¹H NMR (DMSO-d6) δ 1.31 (2H, m), 1.51-1.62 (4H, m), 2.14 (2H, t, J=7.3 Hz), 3.40 (2H, m), 3.45-3.80 (2H, br. m), 4.14 (1H, br. m), 4.41 (3H, br. m), 4.87 (2H, br. m), 7.16-7.30 (12H, m), 7.82 (2H, d, J=7.6 Hz), 8.08 (1H, d, J=8.1 Hz), 8.20 (1H, dd, J=2.7 Hz, J=9.6 Hz), 8.83 (2H, m). Kinetics for release of N-(6-(2,4-dinitrophenyl)aminohexanoyl)-serine from O—(N-(9-fluorenylmethoxycarbonyl-N-phenyl)aminomethyl)-serine in 0.1 M HEPES buffer, 15 mM NaCl, pH 7.40, 37° C. are shown in FIG. 4.

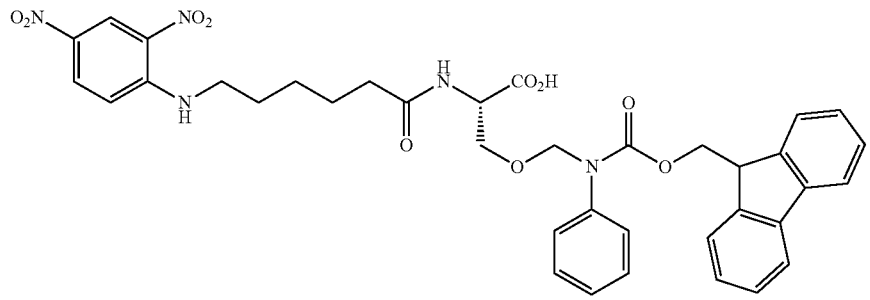

C. S—(N-(9-Fluorenylmethoxycarbonyl-N-Phenylamino)Methyl)N-(2,4-Dinitrophenyl)-Cysteine

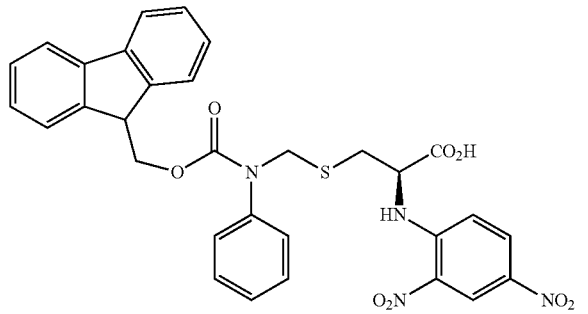

A solution of N-(DNP)-cysteine allyl ester (82 mg) and O-(9-fluorenylmethyl)N-phenyl N-chloromethyl carbamate (91 mg) in dichloromethane (1 mL) was treated with triethylamine (35 µL) for 1 hour, then filtered through silica gel using 1:1 ethyl acetate/hexane and concentrated to dryness. The product was purified by silica gel chromatography.

Figure 3:
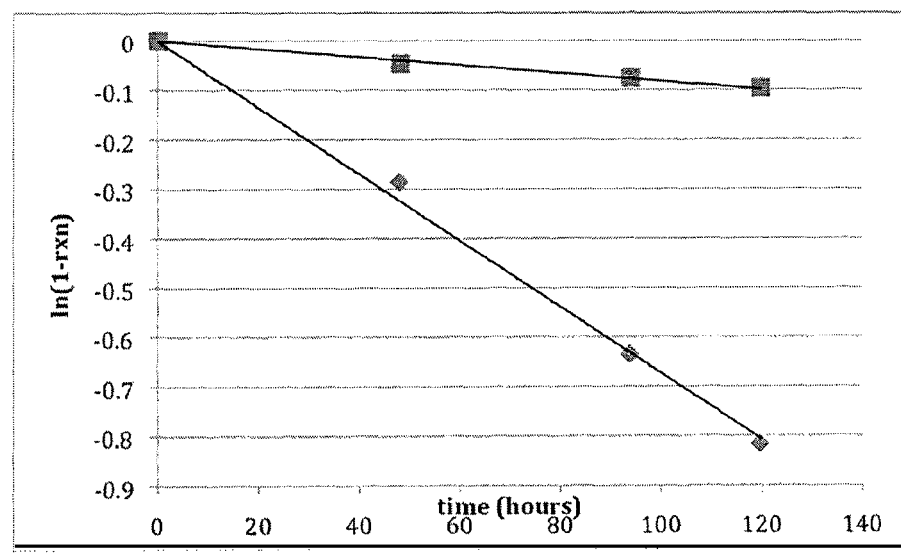
FIG. 3 shows the kinetics of the release of N-(2,4-dinitrophenyl)-cysteine from S—(N-(9-fluorenylmethoxycarbonyl-N-phenyl)aminomethyl) N-(2,4-dinitrophenyl)-cysteine (Example 11C) (diamonds; $T_{1/2}$=100 hours) and S—(N-(ethoxycarbonyl-N-phenyl)aminomethyl) N-(2,4-dinitrophenyl)-cysteine (squares; $T_{1/2}$=850 hours) in 0.1 M HEPES buffer, 15 mM NaCl, pH 7.40, 37° C.

A solution of the allyl ester, phenylsilane (75 µL), and tetrakis(triphenylphosphine)palladium (15 mg) in THF (2.5 mL) was stirred at ambient temperature for 10 minutes, then evaporated to dryness. The residue was dissolved in dichloromethane and loaded onto a 5 mL column of silica gel, which was eluted sequentially with 1:4 ethyl acetate/hexane, ethyl acetate, and 0.5% acetic acid/ethyl acetate. Fractions containing product were combined and evaporated. $^1$H-NMR (d6-DMSO): d 13.7 (1H, br s), 9.01 (1H, d, J=7 Hz), 8.85 (1H, d, J=3 Hz), 8.25 (1H, dd, J=3, 9 Hz), 7.82 (1H, d, J=7), 7.40-7.25 (m, 7H), 7.25-7.15 (m, 3H), 7.11 (m, 2H), 4.96 (m, 1H), 4.81 (s, 2H), 4.30 (m, 2H), 4.08 (m, 1H), 3.18 (m, 2H). Kinetics of release of N-(2,4-dinitrophenyl)-cysteine from S—(N-(9-fluorenylmethoxycarbonyl-N-phenyl)aminomethyl)N-(2,4-dinitrophenyl)-cysteine in 0.1 M HEPES buffer, 15 mM NaCl, pH 7.40, 37° C. are shown in FIG. 3.

Example 12

O-((9-(2-(N-(6-Azidohexanoyl)N-Methyl)Aminomethyl)Fluorenyl)Methyl)N-Phenyl N-Chloromethyl Carbamate

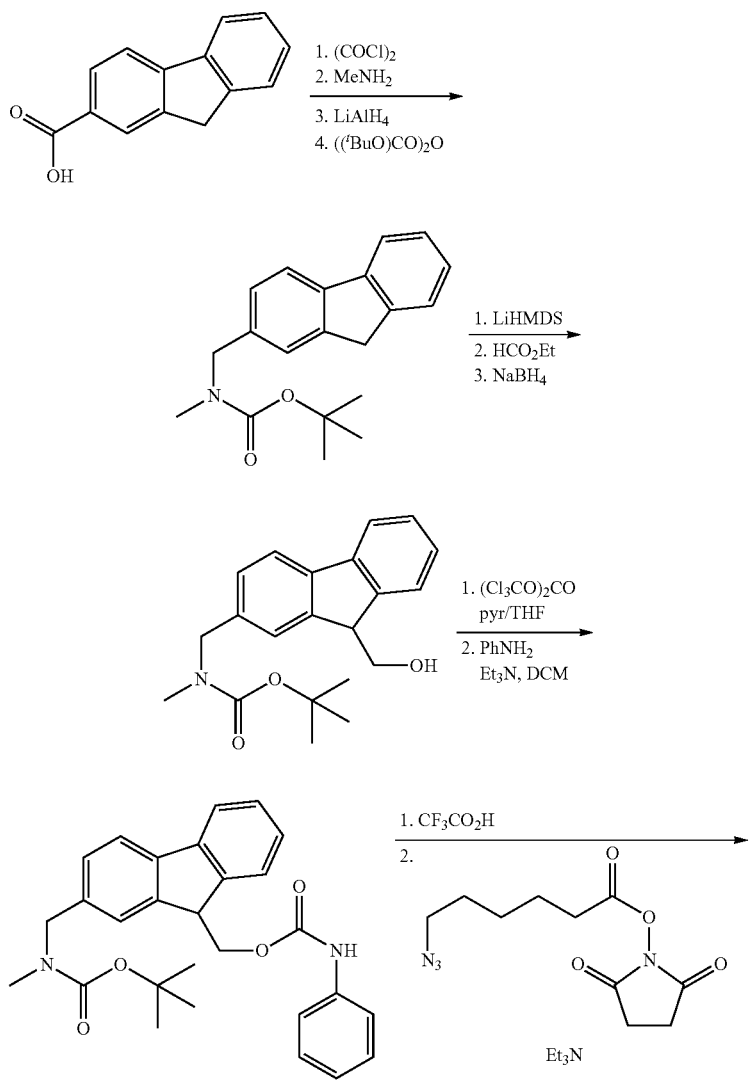

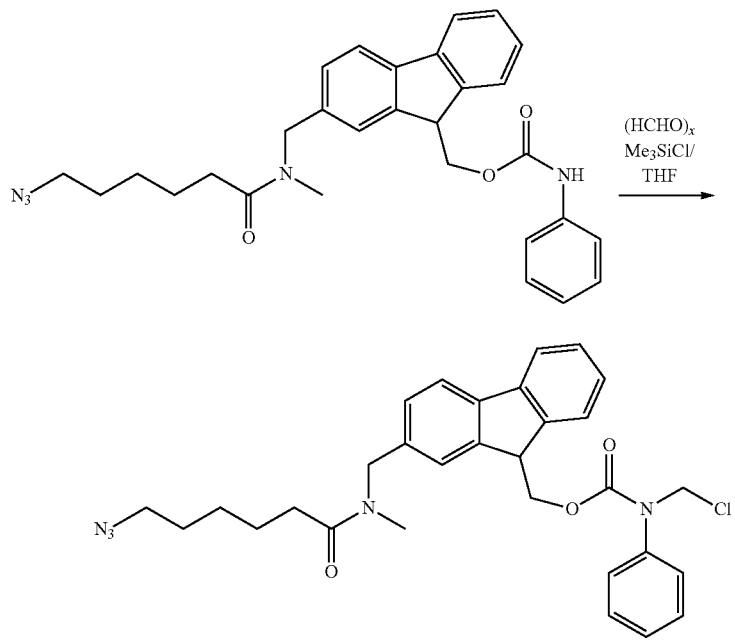

A solution of fluorene-2-carbonyl chloride (prepared from fluorene-2-carboxylic acid and oxalyl chloride) in THF is added to aqueous methylamine (2 molar equivalents) to prepare N-methyl fluorene-2-carboxamide. Reduction of the amide using LiAlH$_4$ in ether provides 2-((methylamino)methyl)fluorene. The amine is protected by reaction with di-tert-butyl dicarbonate to provide 2-((N-$^t$BOC-N-methylamino)methyl)fluorene.

A solution of the 2-((N-$^t$BOC-N-methylamino)methyl) fluorene in anhydrous tetrahydrofuran (THF) is cooled to −78° C., then treated with a solution of lithium bis(trimethylsilyl)amide in THF (1.2 molar equivalents). After 1 hr, ethyl formate is added and the mixture is allowed to warm to ambient temperature. The mixture is diluted with ethyl acetate and washed successively with 0.1 N HCl, water, saturated aqueous NaHCO$_3$, and brine, then dried over MgSO$_4$, filtered, and evaporated to provide the 2-((N-$^t$BOC-N-methylamino)methyl)-fluorene-9-carboxaldehyde. This compound is dissolved in methanol and treated with NaBH$_4$ to provide 9-(2-((N-$^t$BOC-N-methylamino)methyl)fluorenylmethanol.

The 9-(2-((N-$^t$BOC-N-methylamino)methyl)fluorenylmethanol is dissolved in THF and treated with triphosgene and pyridine according to the general procedure of Example 2 to provide the chloroformate. The chloroformate is reacted with aniline according to the method of Example 3 to provide O-(9-(2-((N-$^t$BOC-N-methylamino)methyl)fluorenylmethyl)N-phenylcarbamate.

The carbamate is dissolved in trifluoroacetic acid to remove the $^t$BOC protecting group. After evaporation to dryness, the resulting amine is dissolved in THF and treated with N-(6-azidohexanoyl)succinimide and triethylamine (2 equivalents) to provide O-(9-(2-((N-(6-azidohexanoyl)-N-methylamino)methyl)fluorenylmethyl)N-phenylcarbamate.

Reaction of O-(9-(2-((N-(6-azidohexanoyl)-N-methylamino)methyl)fluorenylmethyl)N-phenylcarbamate with paraformaldehyde in 1:1 THF/chlorotrimethylsilane provides the product N-chloromethyl carbamate.

Example 13

Linker-Drug Compound with SN-38

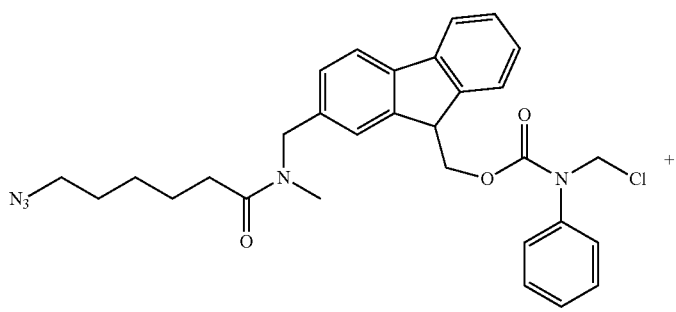

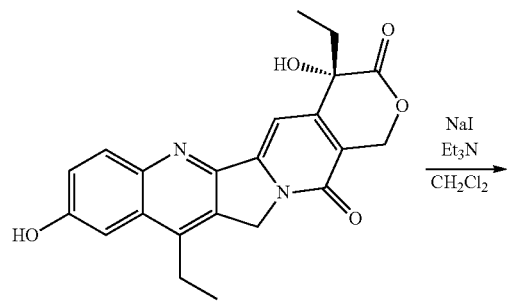

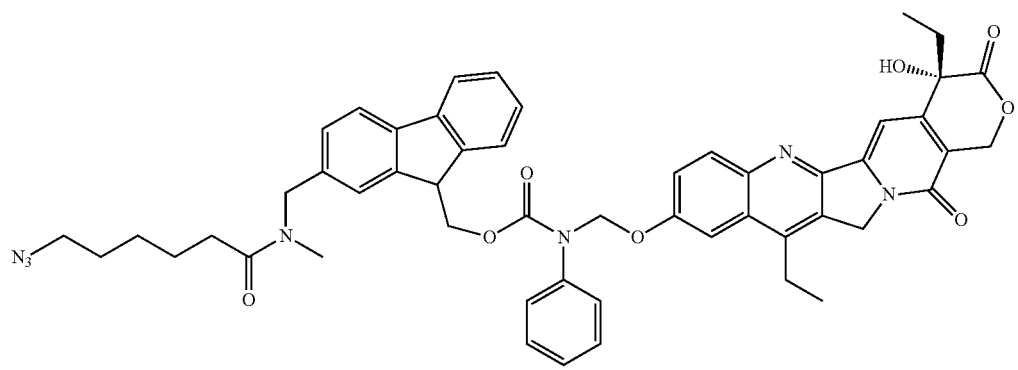

This example demonstrates the linkage of a drug molecule with the compounds of the invention, particularly through a phenol group in the drug molecule.

A solution of the N-chloromethylcarbamate of Example 12 (1 equivalent), SN-38 (1 equivalent), and sodium iodide (10 equivalents) in anhydrous acetone is treated with triethylamine (1 equivalent). The product is purified by silica gel chromatography.

Example 14

Conjugation to PEG

A mixture of 40-kDa PEG-alkyne (2.5 μmol; prepared by reaction of 40-kDa PEG-amine with the N-hydroxysuccinimide ester of 5-hexynoic acid) and an azide-linker (50 μmol; for example, the molecule of Example 12) in THF (3 mL) and water (1.6 mL) is treated with a freshly prepared mixture of 0.1 M CuSO$_4$ (50 μL), 50 mM tris[(1-benzyl-1H-1,2,3-triazol-4-yl)methyl]amine (TBTA) in DMSO (50 μL), and 0.1 M sodium ascorbate (200 μL). After 12 hours at ambient temperature, the mixture is concentrated on a rotary evaporator to remove THF, diluted with water to 2 mL and gel-filtered on a Sephadex G25 column. The flow-through containing macromolecules is then lyophilized, and the residue is dissolved in 2 mL of THF and the product is precipitated by addition of 5 mL of methyl tert-butyl ether. If necessary, the gel-filtration and subsequent steps are repeated.

Example 15

General Scheme for Preparation of an $R^5$ Azidoalkyl-Linkers

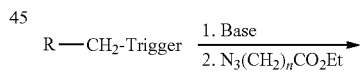

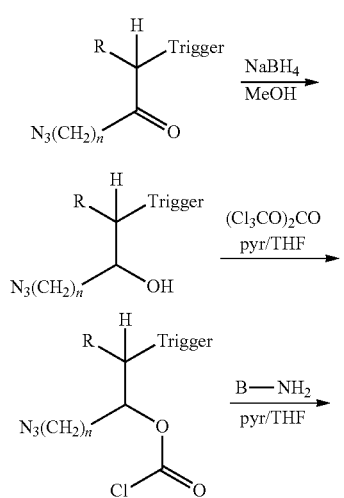

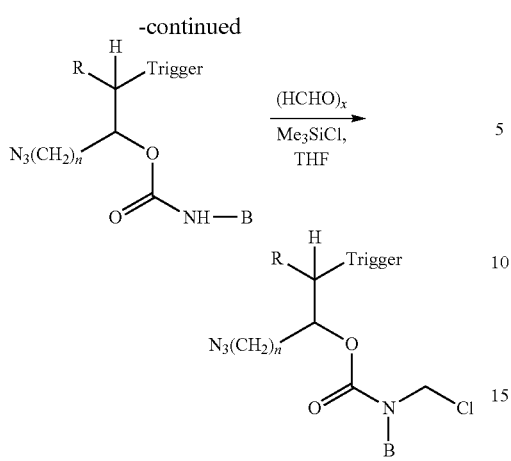

Claisen condensation of R—CH₂-Trigger with an azidoalkanoate ester $N_3(CH_2)_n$—$CO_2R'$ (n=3-6) in the presence of a strong base, for example NaH, lithium bis(trimethylsilyl)amide (LiHMDS), or lithium diisopropylamide (LDA), provides a ketone which is reduced to the alcohol by reaction with a mild reductant, for example sodium borohydride in methanol. The resulting alcohol is then converted into the carbamate via the chloroformate, and then into the N-chloromethylcarbamate as described above.

Example 16

General Scheme for Preparation of $R^5$ BOC-Protected Amine Linkers

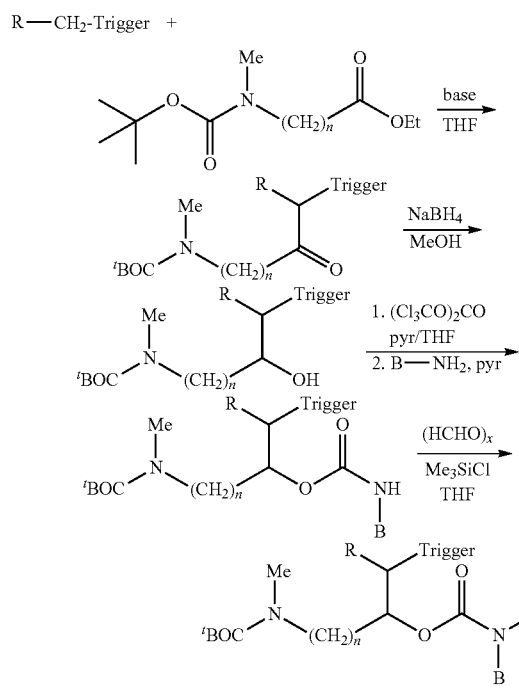

Claisen condensation of R—CH₂-Trigger with an ((N-tert-butoxycarbonyl N-alkyl)amino)alkanoate ester (n=3-6) in the presence of a strong base, for example NaH, lithium bis(trimethylsilyl)amide (LiHMDS), or lithium diisopropylamide (LDA), provides a ketone which is reduced to the alcohol by reaction with a mild reductant, for example sodium borohydride in methanol. The resulting alcohol is then converted into the carbamate using amine B—NH₂ as described in Example 3. The carbamate is converted into the N-chloromethylcarbamate as described in Example 4.

After coupling with a drug molecule comprising an alcohol, thiol, phenol, or thiophenol group, the BOC group is removed from the carbamate by treatment with trifluoroacetic acid. The resulting amine is coupled with a macromolecule comprising a carboxylic acid using a condensing agent, for example a carbodiimide such as EDCI.

Example 17

Alternate Scheme for Preparation of $R^5$ Amido-Azidoalkyl-Linkers

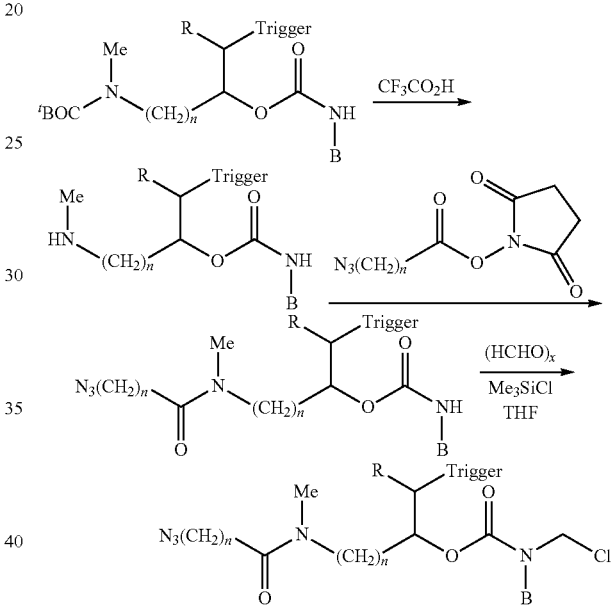

The BOC group is removed from the intermediate BOC-protected carbamate of Example 19 by treatment with trifluoroacetic acid, and reaction of the resulting amine with an azidoalkanoate N-hydroxysuccinimide ester (n=3-6) provides the azidoamide. This is converted into the N-chloromethylcarbamate as described in Example 4.

Example 18

Preparation of a Sulfonyl-Triggered $R^5$ Amine Linker

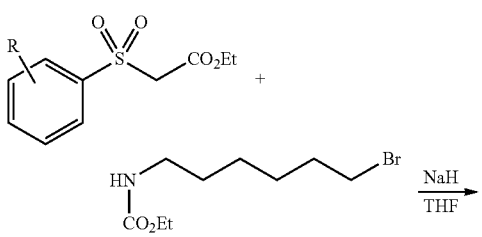

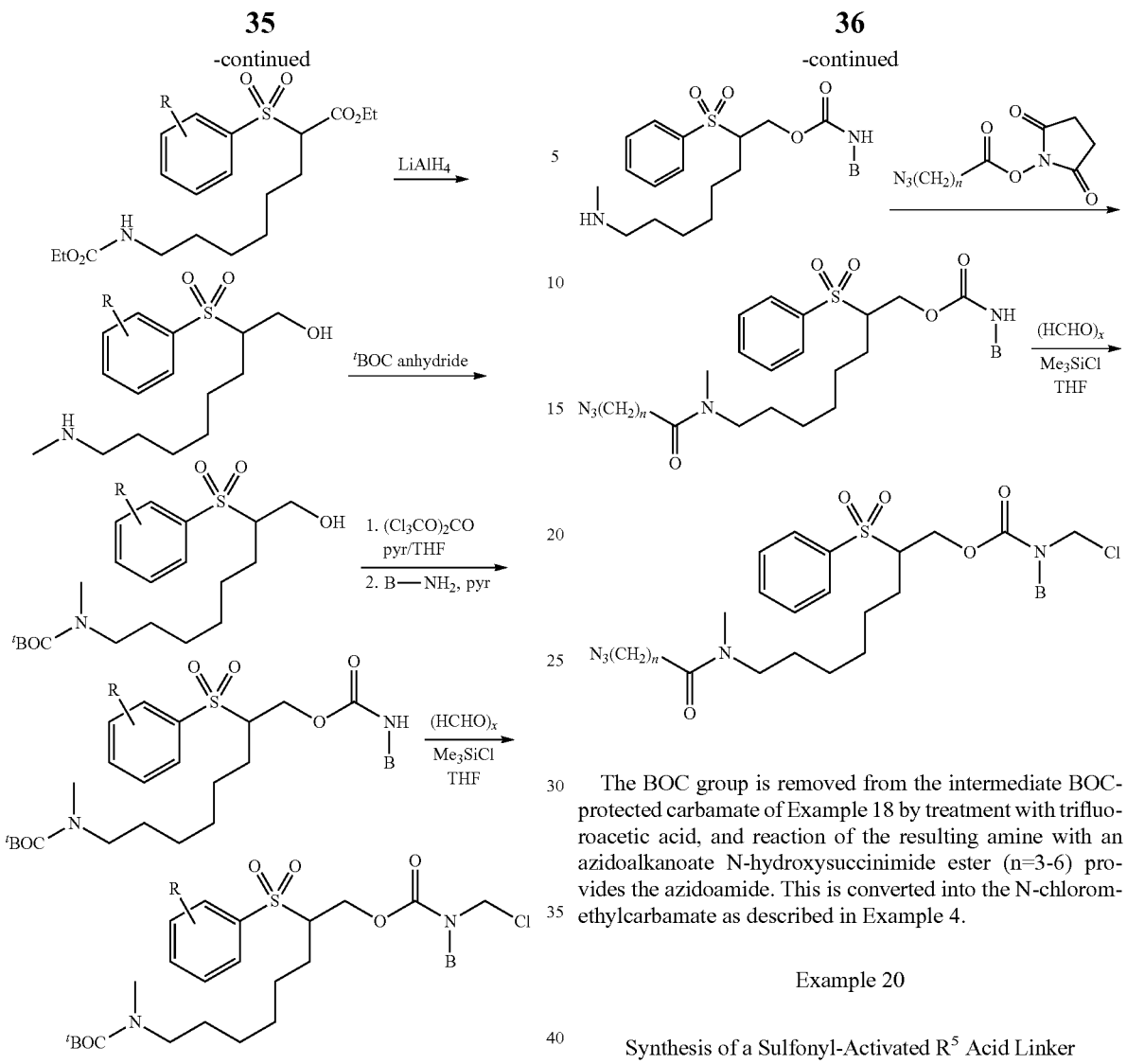

An ethyl(2-phenylsulfonyl)acetate is deprotonated using excess NaH in THF and alkylated with N-(6-bromohexyl) ethyl carbamate. The product is reduced using lithium aluminum hydride in ether to provide the methylamino alcohol, which is N-protected as the BOC carbamate. The alcohol is converted to the chloroformate and thence into the carbamate and into the N-chloromethyl carbamate according to the previous procedures.

Example 19

Preparation of a Sulfonyl-Triggered $R^5$ Amido-Azide Linker

The BOC group is removed from the intermediate BOC-protected carbamate of Example 18 by treatment with trifluoroacetic acid, and reaction of the resulting amine with an azidoalkanoate N-hydroxysuccinimide ester (n=3-6) provides the azidoamide. This is converted into the N-chloromethylcarbamate as described in Example 4.

Example 20

Synthesis of a Sulfonyl-Activated $R^5$ Acid Linker

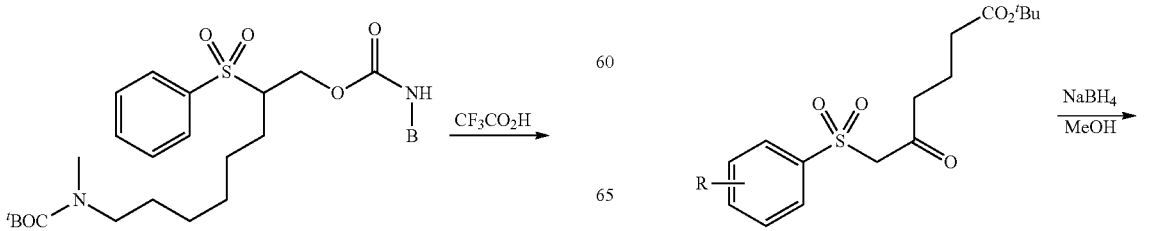

-continued

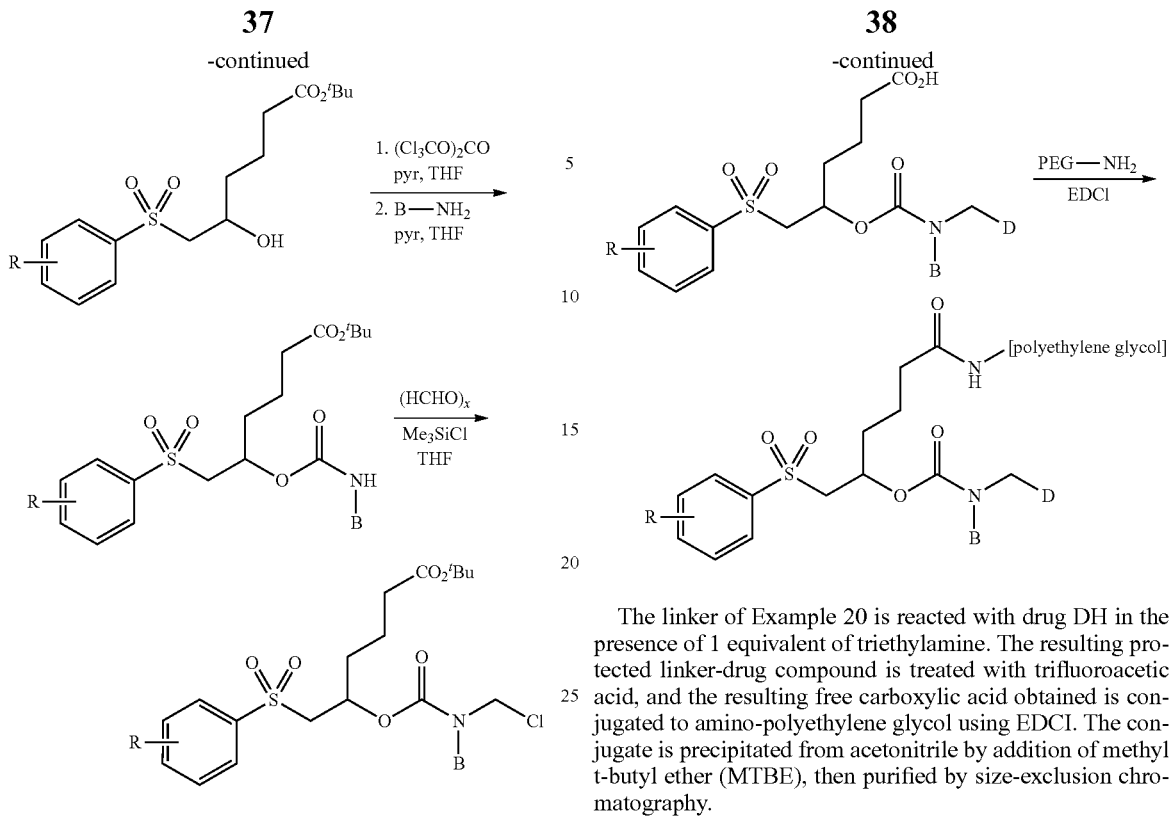

A phenyl methylsulfone is deprotonated with NaH in tetrahydrofuran, when acylated with glutaric anhydride to provide a keto-acid. The resulting acid is protected as the tert-butyl ester, and the ketone is reduced using $NaBH_4$. The resulting alcohol is converted into the carbamate via the chloroformate, and thence to the N-chloromethyl carbamate as described above.

Example 21

Preparation of a Linker-Drug Compound with a Sulfonyl-Activated Acid Linker and Conjugation to PEG

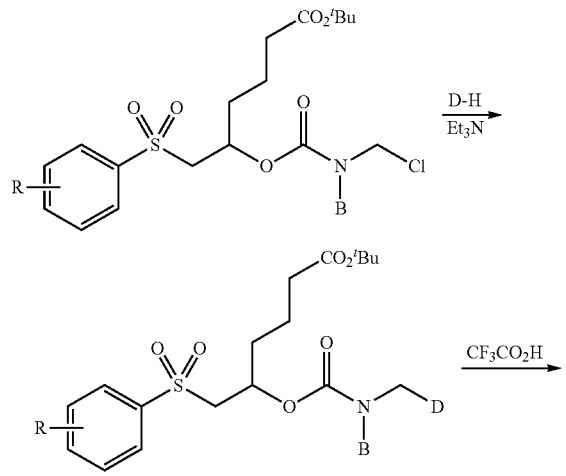

The linker of Example 20 is reacted with drug DH in the presence of 1 equivalent of triethylamine. The resulting protected linker-drug compound is treated with trifluoroacetic acid, and the resulting free carboxylic acid obtained is conjugated to amino-polyethylene glycol using EDCI. The conjugate is precipitated from acetonitrile by addition of methyl t-butyl ether (MTBE), then purified by size-exclusion chromatography.

Example 22

Synthesis of Linked Peptides

This example demonstrates that peptide synthesis is readily accomplished using compounds of the invention. Peptide synthesis is performed using standard methods for solid-phase peptide synthesis, using a serine, tryptophan, tyrosine, or cysteine in a suitably protected form such that the side chains of these residues may be selectively deblocked without deprotection of other residues. The partially deprotected peptide is reacted with an excess of a compound of formula (II) in the presence of a mild base. After washing the resin, the product peptide is deblocked and cleaved from the resin to provide a compound of formula (III) wherein D is a peptide.

As one example, CCK8 (Asp-Tyr-Met-Gly-Trp-Met-Asp-Phe-$NH_2$) is synthesized on solid support using Rink resin using methods known in the art, for example as described in U.S. Pat. No. 4,769,445 (incorporated herein by reference). Commercial Fmoc-Phe-Rink amide-MBHA resin is pre-swollen in DMF for 30 min, then suspended and shaken in piperidine/DMF (1:4 by volume, 50 ml) for 30 min at room temperature to remove the Fmoc group. The product is isolated by filtration and washed (3×50 ml each) with DCM, 5% N,N-diisopropylethylamine (DIEA) in DCM, and DCM to give the free base of Phe-Rink amide-MBHA-Resin. Fmoc-Asp(O$^t$Bu)-OH (1.23 g, 3 mmol), DCC (0.62 g, 3 mmol), and HOBt (0.69 g, 4.5 mmol) are dissolved in 50 ml of 4:1 by volume DCM/DMF with stirring at 0° for 1 hour. Phe-Rink amide-MBHA resin (1 meq) is suspended in the filtered reaction mixture (precipitated DCU removed) and shaken for 2 to 15 hours at room temperature. The Fmoc-Asp-(O$^t$Bu)-Phe-Rink amide-MBHA resin product is collected by filtration and washed with DCM. The Fmoc-Asp-(O$^t$Bu)-Phe-Rink amide-MBHA resin is suspended and shaken in piperidine/DMF (1:4 by volume, 50 ml) for 3 min at room temperature and then a second time for 7 min to remove the Fmoc group.

The product is isolated by filtration and washed (3×50 ml each) with DMF and DCM to give the free base of Asp-(O$^t$Bu)-Phe-Rink amide-MBHA resin. Fmoc-Met-OH (1.12 g, 3 mmol), DCC (0.62 g, 3 mmol), and HOBt (0.69 g, 4.5 mmol) are dissolved in 50 ml of 4:1 by volume DCM/DMF with stirring at 0° for 1 hour. Asp-(O$^t$Bu)-Phe-Rink amide-MBHA resin (1 meq) is suspended in the filtered reaction mixture (precipitated DCU removed) and shaken for 2 to 15 hours at room temperature. The Fmoc-Met-Asp-(O$^t$Bu)-Phe-Rink amide-MBHA resin product is collected by filtration and washed with DCM and DMF. The Fmoc-Met-Asp-(O$^t$Bu)-Phe-Rink amide-MBHA resin is deprotected and coupled sequentially with Fmoc-Trp-OH (1.28 g, 3 mmol), Fmoc-Gly-OH (0.89 g, 3 mmol), Fmoc-Met-OH (1.12 g, 3 mmol), Fmoc-Tyr-OH (1.37 g, 3 mmol), and Boc-Asp (O$^t$Bu)-OH (1.23 g, 3 mmol) to provide Boc-Asp(O$^t$Bu)-Tyr-Met-Gly-Trp-Met-Asp(OtBu)-Phe-Rink amide-MBHA resin. The Boc-Asp(O$^t$Bu)-Tyr-Met-Gly-Trp-Met-Asp (O$^t$Bu)-Phe-Rink amide-MBHA resin is washed with DCM (3×50 ml), suspended and shaken in a mixture of O-(9-fluorenylmethyl)N-phenyl N-chloromethylcarbamate (10 equivalents) and triethylamine (1 equivalent) in DCM. The resin is isolated by filtration and washed (3×50 ml each) with DCM. The resulting Boc-Asp(O$^t$Bu)-Tyr(OX)-Met-Gly-Trp-Met-Asp(OtBu)-Phe-Rink amide-MBHA resin is cleaved from the resin and deblocked by shaking with a mixture of 8% phenol, 5% thioanisole, 5% water, and 3% 3,6-dioxa-1,8-octanedithiol in trifluoroacetic acid (10 mL/g resin) for 4 hours. The resin is removed by filtration, and the peptide is precipitated by addition of 10 volumes of ether. The crude peptide is purified by reversed-phase HPLC.

In another example, a cysteine-containing peptide is prepared by solid phase synthesis using the methods described above, incorporating an S-(allyloxycarbonylaminomethyl)-cysteine [Cys(allocam)] or S—(N-[2,3,5,6-tetrafluoro-4-(N'-piperidino)phenyl]-N-allyloxycarbonyl-amino)cysteine [Cys(fnam)] residue. Prior to cleavage from the resin, the cysteine residue is selectively deblocked using (Ph$_3$P)$_4$Pd and phenylsilane in DCM, then reacted with a compound of formula (II) as described above. The peptide is finally deblocked, removed from the resin, and purified as described above.

Example 23

Linker-Drug Compounds of 5-Fluorouracil

As an example of preparing compounds of the invention where D is the residue of a drug coupled through a heterocyclic N, linker-drug compounds of formula (III) may be prepared from 5-fluorouracil and a compound of formula (II) analogously to the procedures used by Taylor and Sloane, "1-Alkylcarbonyloxymethyl Prodrugs of 5-Fluorouracil (5-FU): Synthesis, Physicochemical Properties, and Topical Delivery of 5-FU", *J. Pharmaceutical Sci.* (1998) 87:15-20, and by Roberts and Sloane, "Synthesis of 3-Alkylcarbonyl-oxymethyl Derivatives of 5-Fluorouracil", *J. Heterocyclic Chem.* 39: 905-910 (each incorporated herein by reference). Thus, a suspension of a compound of formula (II) wherein L is Cl (1 mmol) and NaI (1.3 mmol) in dry acetonitrile (1 mL) is stirred in the dark for 24 h, then filtered to afford a solution of the compound of formula (II) wherein L is I. The filtrate is allowed to react with a mixture of 1-(allyloxycarbonyl-oxymethyl)-5-fluorouracil [Liu, Fullwood, and Rimmer, "Synthesis of Allyloxycarbonylmethyl-5-fluorouracil and copolymerizations with N-vinylpyrrolidinone", *J. Materials Chem.* (2000) 10:1771-1777] (0.8 mmol) and 1,8-bis(dimethy-lamino)naphthalene at ambient temperature. After 6 h, the mixture is diluted with ether, stirred for 1 h, and filtered. The filtrate is concentrated to provide the crude protected product, which is treated with a mixture of tetrakis(triphenylphosphine)-palladium(0) and phenylsilane in anhydrous THF for 1 h to remove the allyloxycarbonylmethyl protecting group. The mixture is evaporated, and the residue is purified by silica gel chromatography to provide the linker-drug compound of formula (III).

Example 24

Preparation of 6-azidohexanal

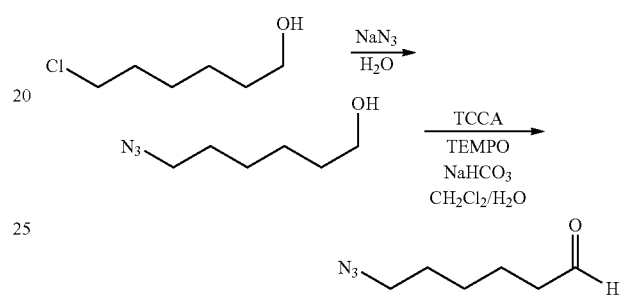

(1) 6-Azido-1-hexanol: a mixture of 6-chloro-1-hexanol (25 g, 183 mmol) and sodium azide (32.5 g, 500 mmol) in 200 mL of water was heated at reflux for 20 h, then cooled to ambient temperature and extracted 3× with ethyl acetate. The combined extracts were washed with brine, dried over MgSO$_4$, filtered, and concentrated to yield the product as a pale yellow oil (28.3 g).

(2) 6-Azidohexanal: Solid trichloroisocyanuric acid (TCCA; 4.3 g) was added in small portions to a vigorously stirred mixture of 6-azido-1-hexanol (7.15 g) and sodium bicarbonate (5.0 g) in dichloromethane (100 mL) and water (10 mL). The mixture was stirred for an additional 30 minutes after addition, then filtered through a pad of diatomaceous earth. The organic phase was separated and washed successively with sat. aq. NaHCO$_3$ and brine, then dried over MgSO$_4$, filtered, and concentrated to provide the product (5.8 g), which was used without further purification.

Example 25

Preparation of Azidoalcohols

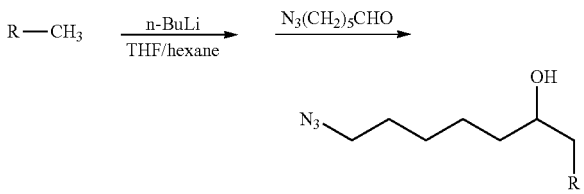

A 1.6 M solution of n-butyllithium (3.1 mL, 5.0 mmol) in hexane was added dropwise to a stirred solution of R—CH$_3$ (5.0 mmol) in anhydrous tetrahydrofuran (THF) (15 mL) cooled to −78° C. After addition, the cooling bath was removed and the mixture was allowed to warm slowly to 0° C. over approximately 30 min. The mixture was then cooled back to −78° C., and 6-azidohexanal (5.5 mmol) was added. After stirring for 15 minutes, the cooling bath was removed and the mixture was allowed to warm. At the point where the mixture became clear, 5 mL of saturated aq. NH₄Cl was added and the mixture was allowed to continue warming to ambient temperature. The mixture was diluted with ethyl acetate and washed successively with water and brine, and then dried over MgSO₄, filtered, and evaporated to provide the crude product as an oil. Chromatography on silica gel using a gradient of ethyl acetate in hexane provided the purified products.

Compounds prepared according to this method include:
1-(4-(trifluoromethyl)phenylsulfonyl)-7-azido-2-heptanol (R—CH₃=4-(trifluoromethyl)phenyl methyl sulfone);
1-(4-chlorophenylsulfonyl)-7-azido-2-heptanol (R—CH₃=4-chlorophenyl methyl sulfone);
1-(phenylsulfonyl)-7-azido-2-heptanol (R—CH₃=phenyl methyl sulfone);
1-(4-methylphenylsulfonyl)-7-azido-2-heptanol (R—CH₃=4-methylphenyl methyl sulfone);
1-(4-methoxyphenylsulfonyl)-7-azido-2-heptanol (R—CH₃=4-methoxyphenyl methyl sulfone);
1-(2,4,6-trimethylphenylsulfonyl)-7-azido-2-heptanol (R—CH₃=2,4,6-trimethylphenyl methyl sulfone);
1-(morpholinosulfonyl)-7-azido-2-heptanol (R—CH₃=4-(methylsulfonyl)-morpholine;
1-(methanesulfonyl)-7-azido-2-heptanol (R—CH₃=dimethyl sulfone);
1-cyano-7-azido-2-heptanol (R—CH₃=acetonitrile);
1-(morpholinocarbonyl)-7-azido-2-heptanol (R—CH₃=4-acetylmorpholine); and
1-(9-fluorenyl)-7-azido-2-heptanol ("R—CH₃"=fluorene).

Example 26

Preparation of Azido-Linker Chloroformates

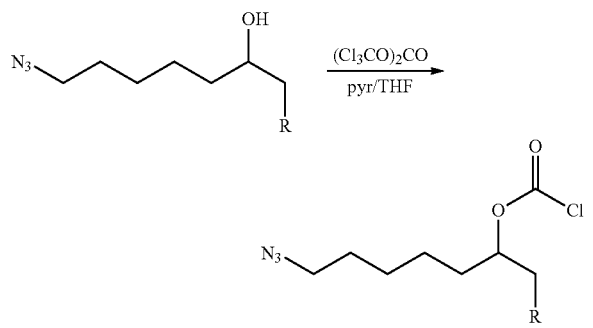

Pyridine (160 μL) was added dropwise to a stirred solution of the azidoalcohol of Example 25 (1.0 mmol) and triphosgene (500 mg) in 15 mL of anhydrous THF. The resulting suspension was stirred for 10 minutes, then filtered and concentrated to provide the crude chloroformate as an oil.

Compounds prepared according to this method include:
1-(4-(trifluoromethyl)phenylsulfonyl)-7-azido-2-heptyl chloroformate;
1-(4-chlorophenylsulfonyl)-7-azido-2-heptyl chloroformate;
1-(phenylsulfonyl)-7-azido-2-heptyl chloroformate;
1-(4-methylphenylsulfonyl)-7-azido-2-heptyl chloroformate;
1-(4-methoxyphenylsulfonyl)-7-azido-2-heptyl chloroformate;
1-(2,4,6-trimethylphenylsulfonyl)-7-azido-2-heptyl chloroformate;
1-(morpholinosulfonyl)-7-azido-2-heptyl chloroformate;
1-(methanesulfonyl)-7-azido-2-heptyl chloroformate;
1-cyano-7-azido-2-heptyl chloroformate;
1-(morpholinocarbonyl)-7-azido-2-heptyl chloroformate; and
1-(9-fluorenyl)-7-azido-2-heptyl chloroformate.

En route to a model system lacking the trigger functionality, 6-azidohexyl chloroformate was prepared as described above, starting from 6-azidohexanol.

Example 27

Preparation of Azido-Linker-HSE Carbonates

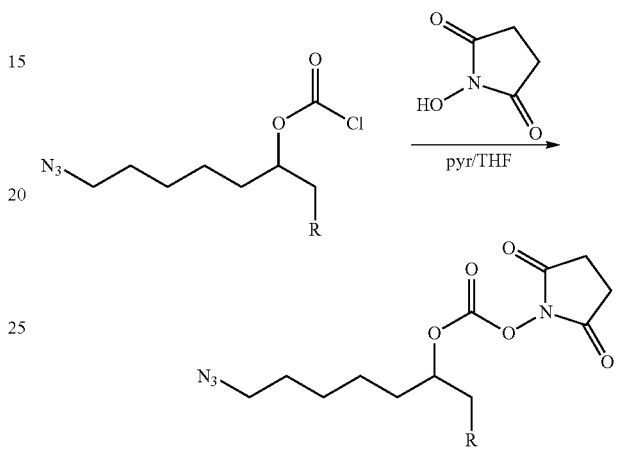

A solution of the chloroformate of Example 26 in 15 mL of dry THF was treated successively with N-hydroxysuccinimide (350 mg) and pyridine (250 μL) for 10 minutes. The mixture was then concentrated, and the residue was redissolved in ethyl acetate. After washing with 0.1 N HCl, water, sat. NaHCO₃, water, and brine, the solution was dried over MgSO₄, filtered, and evaporated. In some cases, the HSE carbonate spontaneously crystallized, and was recrystallized from ethyl acetate/hexane. In other cases, the crude HSE carbonate was first chromatographed on silica gel using a gradient of ethyl acetate in hexane, followed by crystallization. All compounds were crystalline with the exception of that obtained from 1-(methanesulfonyl)-7-azido-2-heptanol.

Compounds prepared according to this method include:
O-[1-(4-(trifluoromethyl)phenylsulfonyl)-7-azido-2-heptyl]-O'-succinimidyl carbonate;
O-[1-(4-chlorophenylsulfonyl)-7-azido-2-heptyl]-O'-succinimidyl carbonate;
O-[1-(phenylsulfonyl)-7-azido-2-heptyl]-O'-succinimidyl carbonate;
O-[1-(4-methylphenylsulfonyl)-7-azido-2-heptyl]-O'-succinimidyl carbonate;
O-[1-(4-methoxyphenylsulfonyl)-7-azido-2-heptyl]-O'-succinimidyl carbonate;
O-[1-(2,4,6-trimethylphenylsulfonyl)-7-azido-2-heptyl]-O'-succinimidyl carbonate;
O-[1-(morpholinosulfonyl)-7-azido-2-heptyl]-O'-succinimidyl carbonate;
O-[1-(methanesulfonyl)-7-azido-2-heptyl]-O'-succinimidyl carbonate;
O-[1-cyano-7-azido-2-heptyl]-O'-succinimidyl carbonate;
O-[1-(morpholinocarbonyl)-7-azido-2-heptyl]-O'-succinimidyl carbonate;
O-[1-(9-fluorenyl)-7-azido-2-heptyl]-O'-succinimidyl carbonate.

Also prepared according to this method was O-[6-azidohexyl]-O'-succinimidyl carbonate, starting from 6-azidohexyl chloroformate.

Example 28

Preparation of 4-(N,N-diethylcarboxamido)aniline

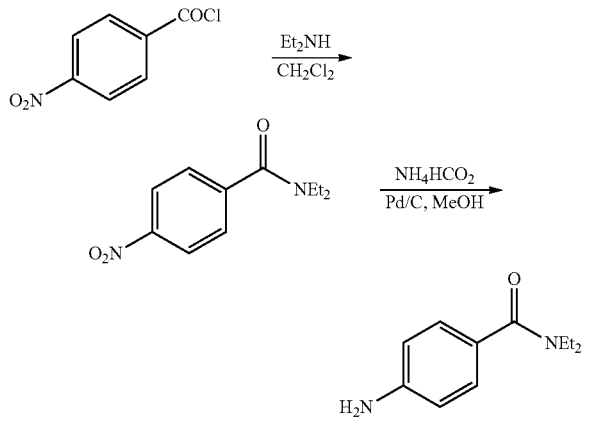

(1) N,N-Diethyl 4-nitrobenzamide: Diethylamine (5.6 mL) was added to an ice-cold solution of 4-nitrobenzoyl chloride (5.0 g) in 100 mL of DCM. After 1 h, the mixture was washed successively with water, sat. aq. NaHCO$_3$, and brine, then dried over MgSO$_4$, filtered, and evaporated to provide a colorless liquid that crystallized on standing. Recrystallization from ethyl acetate/hexane provided the product as pale yellow crystals (4.6 g).

(2) 4-(N,N-Diethylcarboxamido)aniline: A mixture of N,N-diethyl 4-nitrobenzamide (4.44 g) and 10% palladium on carbon (0.2 g) in 100 mL of methanol was treated with ammonium formate (4.0 g) for 2 h at ambient temperature. The mixture was filtered through diatomaceous earth and concentrated. The residue was redissolved in DCM, washed successively with 0.5 M Na$_2$CO$_3$, water, and brine, then dried over MgSO$_4$, filtered, and evaporated to provide a crystalline material. Recrystallization from ethyl acetate/hexane provided the product aniline.

Also prepared according to the same procedure was 4-(morpholinocarbonyl)aniline by replacing diethylamine with morpholine.

Example 29

Preparation of Azidocarbamates

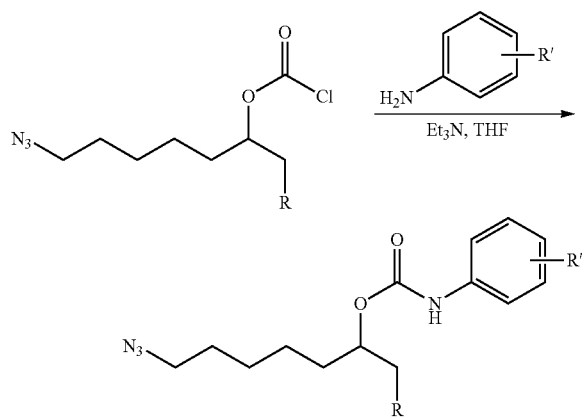

The crude chloroformate prepared from 2.5 mmol of azidoalcohol according to the procedure of Example 26 was dissolved in 20 mL of THF, and the aniline (2.5 mmol) and triethylamine (0.7 mL, 5.0 mmol) were added. After 1 h, the mixture was diluted with ethyl acetate, washed successively with 1 N HCl, water, sat. NaHCO$_3$, and brine, then dried over MgSO$_4$, filtered, and evaporated. The residue was chromatographed on silica gel using ethyl acetate/hexane to provide the product carbamate.

Compounds prepared according to this method include:

O-[1-(phenylsulfonyl)-7-azido-2-heptyl]-N-[4-(diethylcarboxamido)phenyl carbamate;

O-[1-(morpholinosulfonyl)-7-azido-2-heptyl]-N-[4-(diethylcarboxamido)phenyl carbamate;

O-[1-(methanesulfonyl)-7-azido-2-heptyl]-N-[4-(diethylcarboxamido)phenyl carbamate;

O-[1-(phenylsulfonyl)-7-azido-2-heptyl]-N-[4-(morpholinocarboxamido)phenyl carbamate; and O-[1-(phenylsulfonyl)-7-azido-2-heptyl]-N-[4-(morpholinosulfonyl)phenyl carbamate.

Example 30

Preparation of N-chloromethyl Carbamates

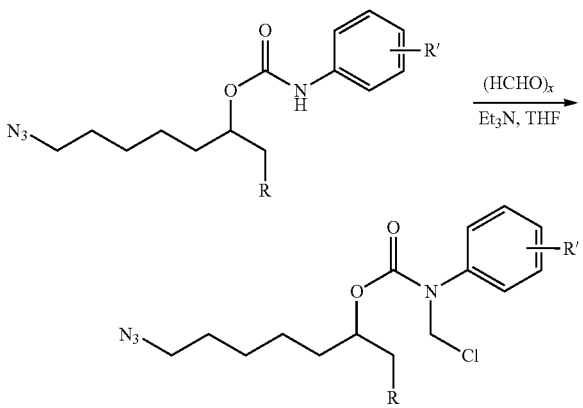

A mixture of the azidocarbamate of Example 29 (1.0 mmol), paraformaldehyde (45 mg), chlorotrimethylsilane (1 mL), and THF (1 mL) in a sealed 20 mL vial was heated in a 55° C. bath for 17 h. After cooling to ambient temperature, the vial was opened and the mixture was concentrated on a rotary evaporator to a thick oil, which was taken up in ethyl acetate and reconcentrated. The residue was dissolved in 2:1 ethyl acetate/hexane, filtered, and concentrated to provide the N-chloromethyl carbamate, which was used without further purification.

Compounds prepared according to this method include:

O-[1-(phenylsulfonyl)-7-azido-2-heptyl]-N-[4-(diethylcarboxamido)phenyl]-N-chloromethyl carbamate;

O-[1-(morpholinosulfonyl)-7-azido-2-heptyl]-N-[4-(diethylcarboxamido)phenyl]-N-chloromethyl carbamate;

O-[1-(methanesulfonyl)-7-azido-2-heptyl]-N-[4-(diethylcarboxamido)phenyl]-N-chloromethyl carbamate; and O-[1-(morpholinocarbonyl)-7-azido-2-heptyl]-N-[4-(diethylcarboxamido)phenyl]-N-chloromethyl carbamate, O-[6-Azidohexyl][4-(diethylcarboxamido)phenyl]-N-chloromethyl carbamate was also prepared en route to a control compound lacking a trigger group.

Example 31

Preparation of N-alkoxymethyl Carbamates

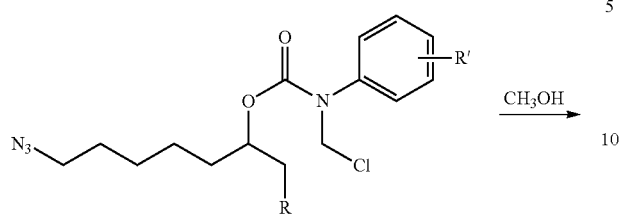

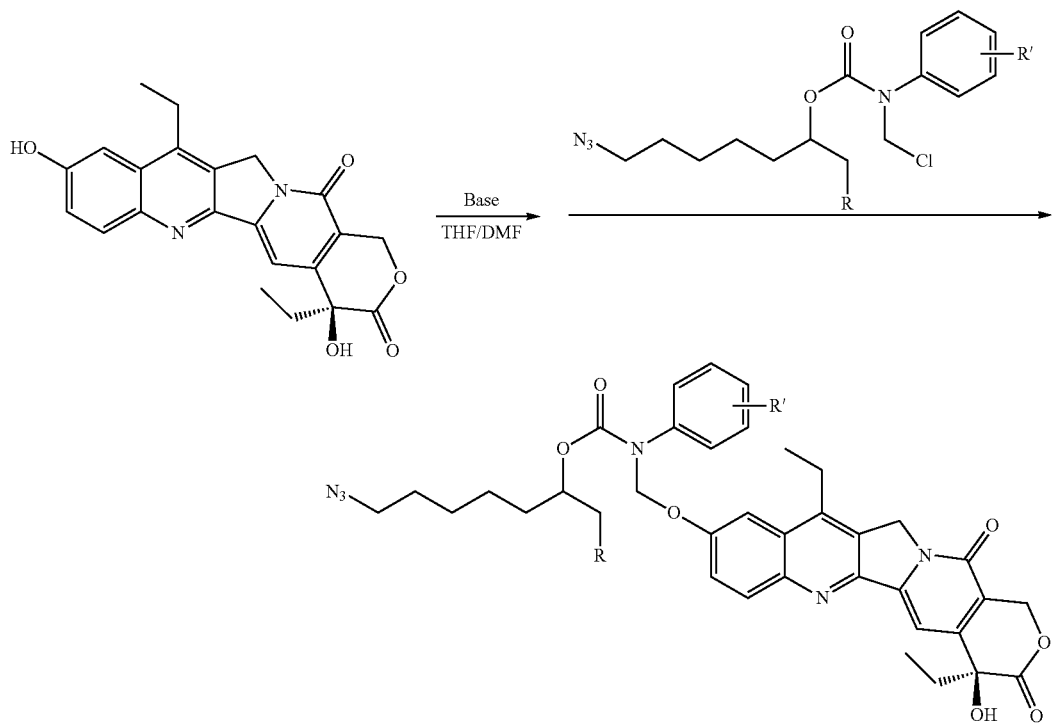

-continued

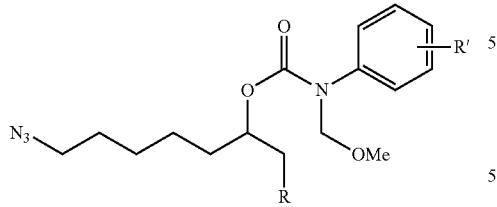

The N-chloromethyl carbamate of Example 30 (0.4 mmol) is dissolved in 5 mL of dry alcohol. After 1 h, the mixture is evaporated to dryness, and the residue is chromatographed on silica gel (ethyl acetate/hexanes) to provide the product.

Compounds prepared according to this method include:
O-[1-(phenylsulfonyl)-7-azido-2-heptyl]-N-[4-(diethylcarboxamido)phenyl]-N-methoxymethyl carbamate;
O-[1-(morpholinosulfonyl)-7-azido-2-heptyl]-N-[4-(diethylcarboxamido)phenyl]-N-methoxymethyl carbamate; and
O-[1-(methanesulfonyl)-7-azido-2-heptyl]-N-[4-(diethylcarboxamido)phenyl]-N-methoxymethyl carbamate.
O-[6-Azidohexyl]-N-[4-(diethylcarboxamido)phenyl]-N-methoxymethyl carbamate was also prepared en route to a control compound lacking a trigger group.

Example 32

Preparation of azido-linker-SN38

Procedure 1 (Base=DBU).

A suspension of SN-38 (7-ethyl-10-hydroxycamptothecin) (40 mg, 0.1 mmol) in 5 mL of THF was treated with 16.5 μL of 1,8-diazabicyclo[5.4.0]undec-7-ene (DBU). A clear golden solution formed after 30 minutes. A solution of the N-chloromethylcarbamate of Example 30 (0.11 mmol) in 1 mL of THF was added, resulting in formation of a sticky precipitate. After 30 minutes, HPLC analysis indicated ~40% conversion of SN-38 to the azide-linker-SN38 adduct. Additional DBU (20 μL) and N-chloromethylcarbamate (0.04 mmol) were added. After 15 minutes, the mixture was quenched by addition of 10% aqueous citric acid and extracted with dichloromethane (DCM). The extract was washed successively with 10% citric acid, water, and brine, then dried over MgSO$_4$, filtered, and evaporated. The residue was dissolved in DCM, filtered, and evaporated to provide the product.

Procedure 2 (Base=LiHMDS).

A suspension of SN-38 (42 mg) in 5 mL of 4:1 THF/DMF was cooled in a −78° C. bath and treated dropwise with a 1.0 M solution of lithium bis(trimethylsilylamide) in THF (150 μL). The mixture turned dark green upon addition of base, followed by formation of a dark gold color. After completion of addition, the mixture was allowed to warm to ambient temperature and a solution of the N-chloromethylcarbamate of Example 30 (0.2 mop in 1 mL of THF was added. After 10 minutes, the reaction was quenched by addition of 10% aqueous citric acid and extracted with dichloromethane (DCM). The extract was washed successively with 10% citric acid, water, and brine, then dried over MgSO$_4$, filtered, and evaporated to provide a yellow oily material. Trituration with water to remove excess DMF provided the crude product as a yellow solid. The residue was dissolved in DCM and chromatographed on silica gel using a gradient of acetone in hexane to provide purified product.

Products prepared according to this procedure include:

R=phenylsulfonyl, R'=4-(N,N-diethylcarboxamido);

R=morpholinosulfonyl, R'=4-(N,N-diethylcarboxamido); and

R=methanesulfonyl, R'=4-(N,N-diethylcarboxamido).

Example 33

Preparation of 4-arm PEG-[DBCO]$_4$

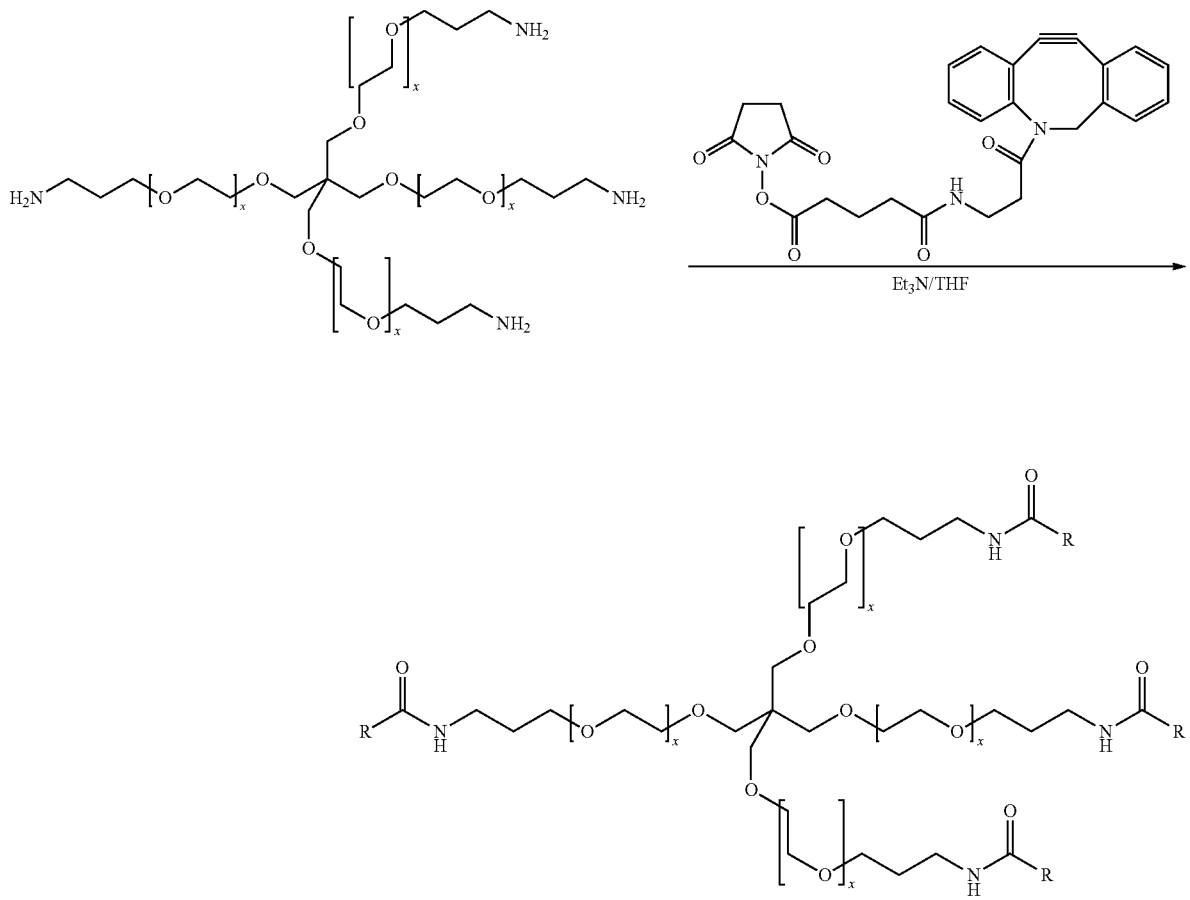

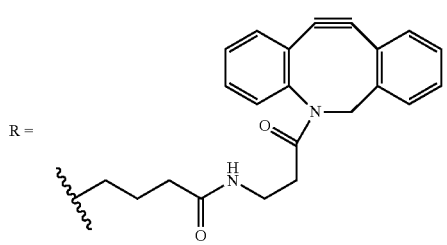

A solution of 40-kDa 4-arm polyethyleneglycol with aminopropyl end-groups having a pentaerythritol core (NOF America, PTE400PA) (500 mg, 12.5 μmol), triethylamine (20 μL), and 6-aza-5,9-dioxo-9-(1,2-didehydrodibenzo[b,f]azocin-5(6H)-yl)nonanoic acid succinimidyl ester ("DBCO-NHS", Click Chemistry Tools, Macon, Ga.) (36 mg, 75 μmol) in 5 mL of THF was stirred for 24 h at ambient temperature. The product was precipitated by addition of the reaction mixture to 50 mL of methyl tert-butyl ether (MTBE). The precipitate was collected by vacuum filtration and dried under vacuum to provide 510 mg of product.

Example 34

Preparation of Releasable 4-arm PEG-SN38 Conjugates

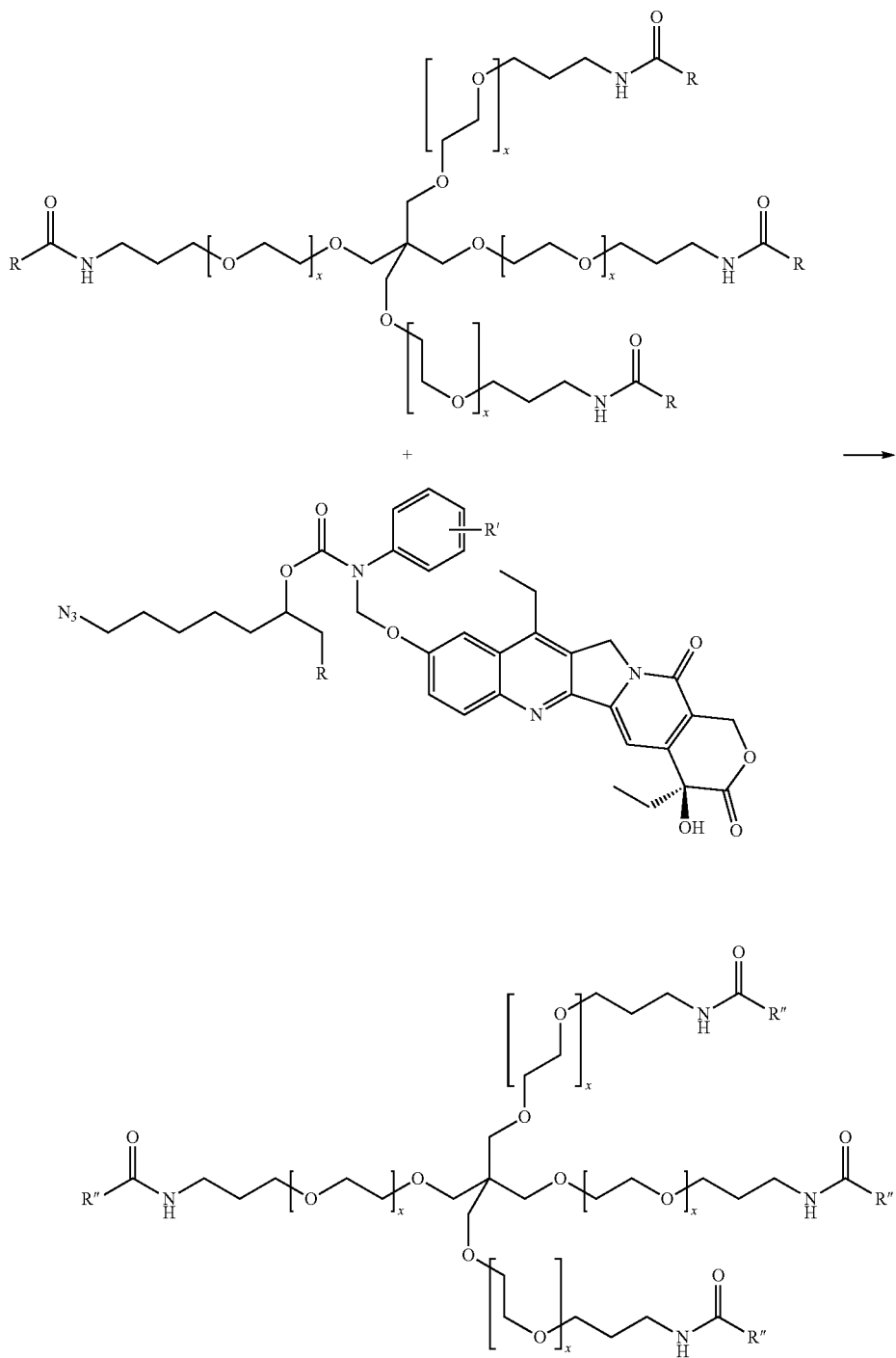

R = 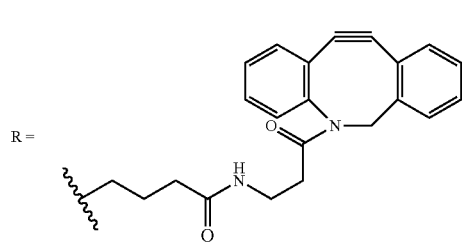

R'' = 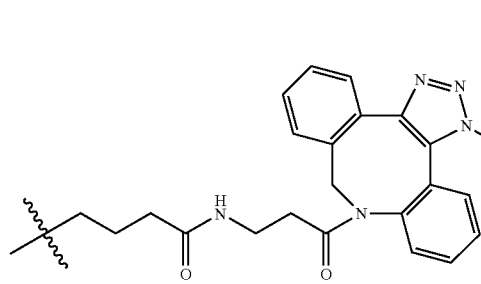

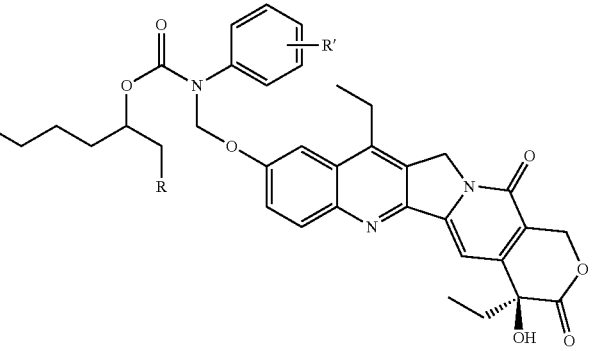

A solution of 4-arm PEG-[DBCO]$_4$ (100 mg, 2.0 μmol DBCO) and the azide-linker-SN38 of Example 32 (10 μmol) in 1.5 mL of THF was kept at ambient temperature for 21 hours. The mixture was concentrated, then redissolved in methanol and dialyzed (10 kDa cutoff membrane) against methanol to remove free azide. After concentration on a rotary evaporator, the product was dissolved in 2 mL of THF and precipitated by addition of 10 mL of MTBE. The precipitate was collected by vacuum filtration and dried under vacuum to provide the product conjugate. HPLC analysis (300A C4 Jupiter column (Phenomenex), thermostatted at 40° C.) using a gradient from 20-100% acetonitrile in water+ 0.1% TFA demonstrated no unconjugated SN-38 or free azide was present. The SN-38 content was then determined by measuring the UV absorbance of an aqueous solution using $\epsilon$=22,500 M$^{-1}$ cm$^{-1}$ at 361 nm.

Releasable conjugates prepared according to this procedure include: R=phenylsulfonyl; R=methanesulfonyl; and R=morpholinosulfonyl, each having R'=4-(N,N-diethylcarboxamido). As a control, the conjugate lacking the trigger group was prepared according to the same procedure.

Example 35

Release of SN-38 from PEG-SN38 Conjugates

Samples of 4-arm SN-38 conjugates of Example 34 wherein R'=4-N,N-diethylcarboxamido and R=phenylsulfonyl or methanesulfonyl were dissolved in buffer and kept at 37° C. Aliquots of 20 μL were periodically injected onto the HPLC (300A C4 Jupiter column (Phenomenex), thermostatted at 40° C.) and analyzed using a gradient from 20-100% acetonitrile in water+0.1% TFA using fluorescence detection (excitation 380 nm; emission 515 nm). Under these conditions, free SN-38 eluted at 5 min and conjugate eluted at 7 min. Peak areas were measured and used to calculate the rate of reaction by exponential fit.

The conjugate wherein R'=4-N,N-diethylcarboxamido and R=phenylsulfonyl in 0.1 M bicine, pH 8.5, 37° C. released SN-38 with a $T_{1/2}$=1.6 h, whereas the conjugate wherein R'=4-N,N-diethylcarboxamido and R=methanesulfonyl released SN-38 with $T_{1/2}$=9 h under the same conditions.

Example 36

Pharmacokinetics of 4-arm PEG-SN38 Conjugates in Mice

Dosing solutions were prepared by dissolving the 4-arm PEG-SN38 conjugates of Example 34 in 10 mM sodium acetate, pH 5.0, so as to give a final SN-38 concentration of 1 mM as determined by UV absorbance at 361 nm ($\epsilon$=22,500 M$^{-1}$ cm$^{-1}$). The dosing solutions were sterile filtered using a 0.2 μm syringe filter and frozen.

Figure 8:
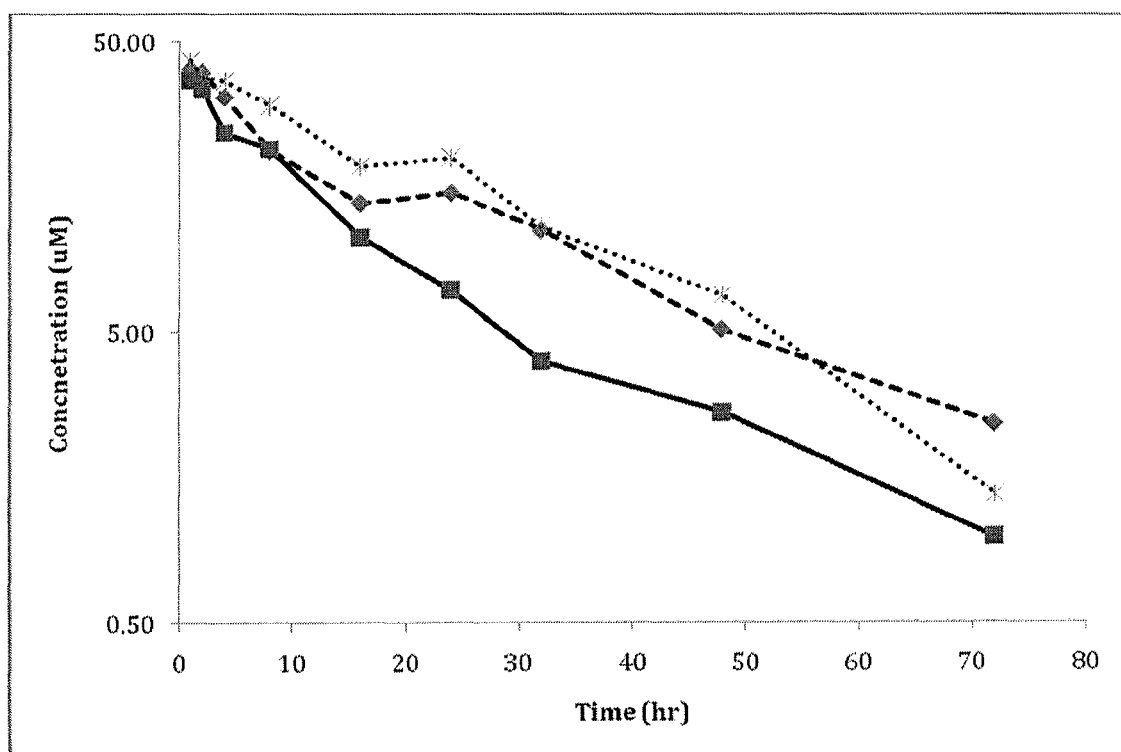
FIG. 8 shows the results of Example 44 for the concentration of 4-arm PEG-SN-38 conjugates (Example 42, wherein R'=4-N,N-diethylcarboxamido and R=phenylsulfonyl or methanesulfonyl) as a function of time in mouse serum. Legend: Solid line, R=phenylsulfonyl; dotted line, R=morpholinosulfonyl; dashed line, R=methansulfonyl.

Samples were injected intravenously into four CD-1 mice per compound at 2 μL/g body weight. Blood samples were collected from the orbital sinus using the following schedule: mouse 1: 1, 16 and 72 hr; mouse 2: 2 and 24 hr; mouse 3: 4 and 32 hr; mouse 4: 8 and 48 hr. Samples were immediately frozen at −80° C. until analyzed. One-third volume of a 0.25 mg/mL solution of $N_\epsilon$-(2,4-dintrophenyl)-L-lysine was added to each serum sample as an internal standard for a final concentration of 0.0625 mg/mL. One-half volume of 200 mM triethylamine.HCl buffer, pH 10.75, was added to each serum sample and placed at 37° C. for 16 hours. Following hydrolysis, the serum proteins were precipitated with three volumes of methanol. A standard curve was prepared from a stock solution of the conjugate wherein R=CH$_3$SO$_2$ and R'=4-(N, N-diethylcarboxamido) diluted in mouse serum and hydrolyzed using the same procedure. The samples and standards were analyzed for total free SN38 on a Shimadzu HPLC with a Jupiter C4 300 Å5μ column using a 20-100% gradient of acetonitrile in H$_2$O with 0.1% trifluoroacetic acid. SN38 was detected with a fluorescence detector set at 380 nm/515 nm excitation/emission. Fluorescence peak areas were used to calculate SN38 concentration from the standard curve. PK Solutions pharmacokinetics software was used to calculate the pharmacokinetic parameters from the data. The results are shown in FIG. 8.

Example 37

Linking to Peptide Thiols with N-chloromethyl Carbamates

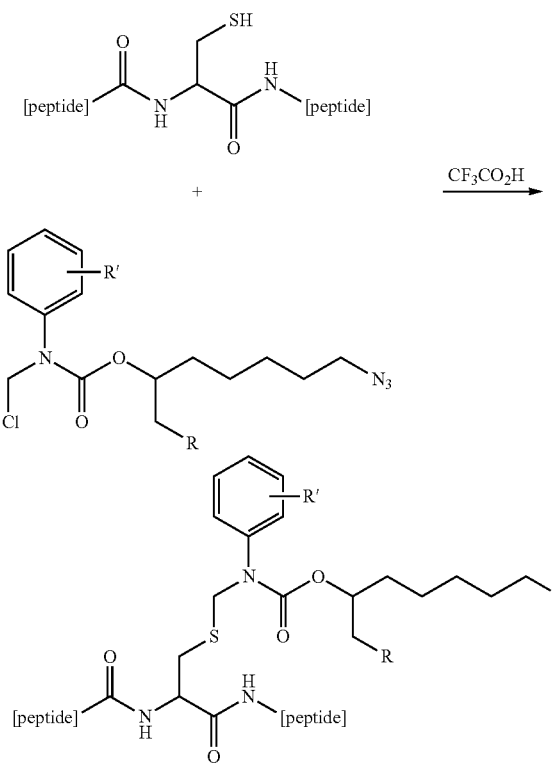

The N-chloromethyl carbamate of Example 30 (0.1 µmol) is added to a solution of the thiol-containing peptide (0.1 µmol) in 1.0 mL of trifluoroacetic acid (TFA). After 2 h, the product is precipitated by addition of 5 mL of ethyl ether and collected by centrifugation. The precipitate is washed 3× with ether and dried. This is dissolved in acetate buffer, pH 5, and loaded onto a 1-g BondElut C18 cartridge. The cartridge is washed with a step gradient of methanol in water containing 0.1% TFA to elute the purified product.

Example 38

Linking to Peptide Thiols with N-alkoxymethyl Carbamates

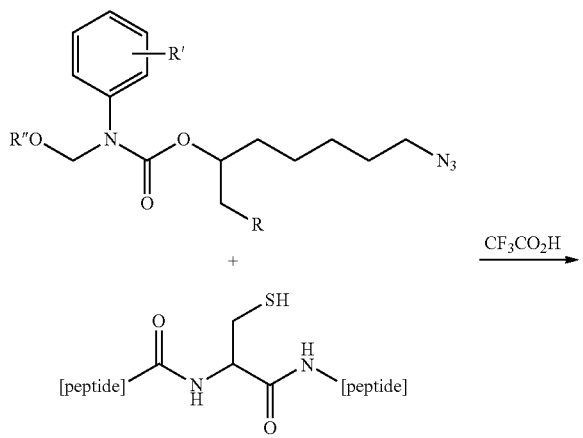

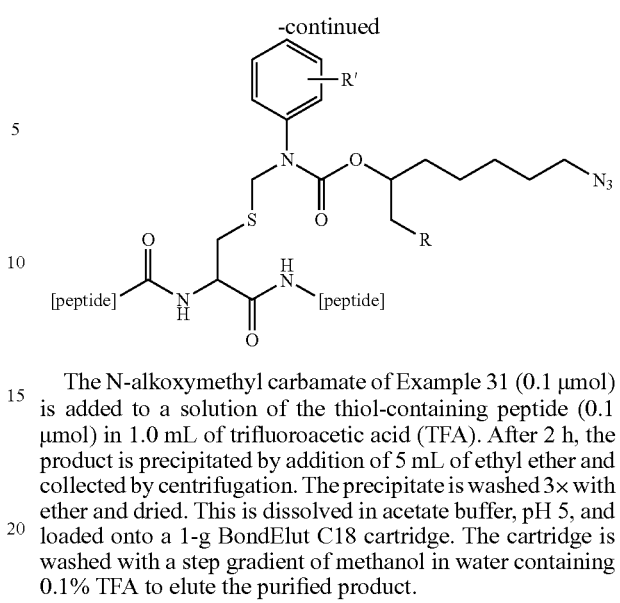

The N-alkoxymethyl carbamate of Example 31 (0.1 µmol) is added to a solution of the thiol-containing peptide (0.1 µmol) in 1.0 mL of trifluoroacetic acid (TFA). After 2 h, the product is precipitated by addition of 5 mL of ethyl ether and collected by centrifugation. The precipitate is washed 3× with ether and dried. This is dissolved in acetate buffer, pH 5, and loaded onto a 1-g BondElut C18 cartridge. The cartridge is washed with a step gradient of methanol in water containing 0.1% TFA to elute the purified product.

Example 39

Preparation of Azide-Linker Glutathione

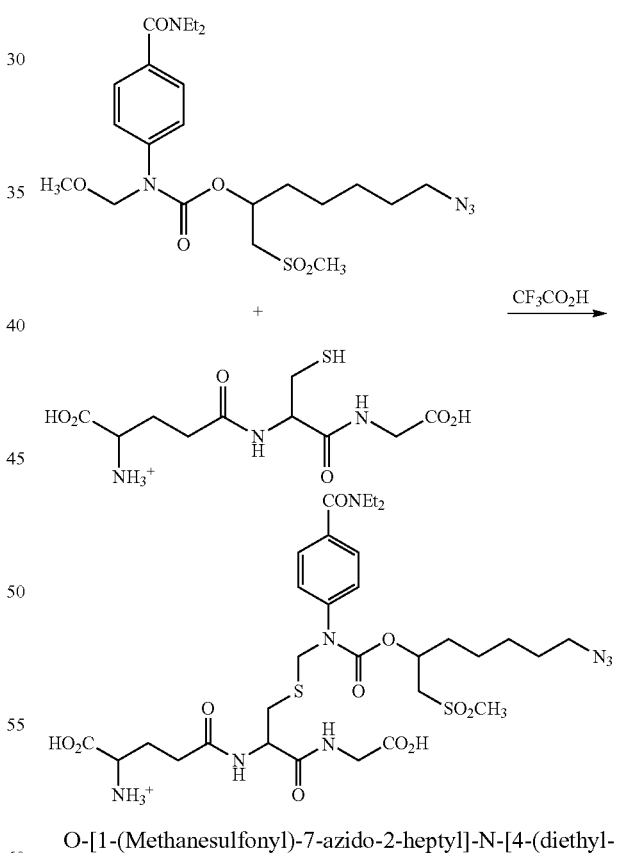

O-[1-(Methanesulfonyl)-7-azido-2-heptyl]-N-[4-(diethylcarboxamido)phenyl]-N-methoxymethyl carbamate (50 mg) was added to a solution of reduced glutathione (50 mg) in 1.0 mL of trifluoroacetic acid (TFA). After 2 h, the product was precipitated by addition of 5 mL of ethyl ether, collected, and dried. The precipitate was dissolved in 5 mL of 10 mM sodium acetate buffer, pH 5, and loaded onto a 1-g BondElut C18 cartridge. The cartridge was washed with 10 mL of water/0.1% TFA to remove excess glutathione followed by 10 mL of 1:1 methanol/water/0.1% TFA to elute the product. The product-containing eluate was evaporated to dryness on a rotary evaporator.

Example 40

Conjugation of Thiol-Linked Peptides

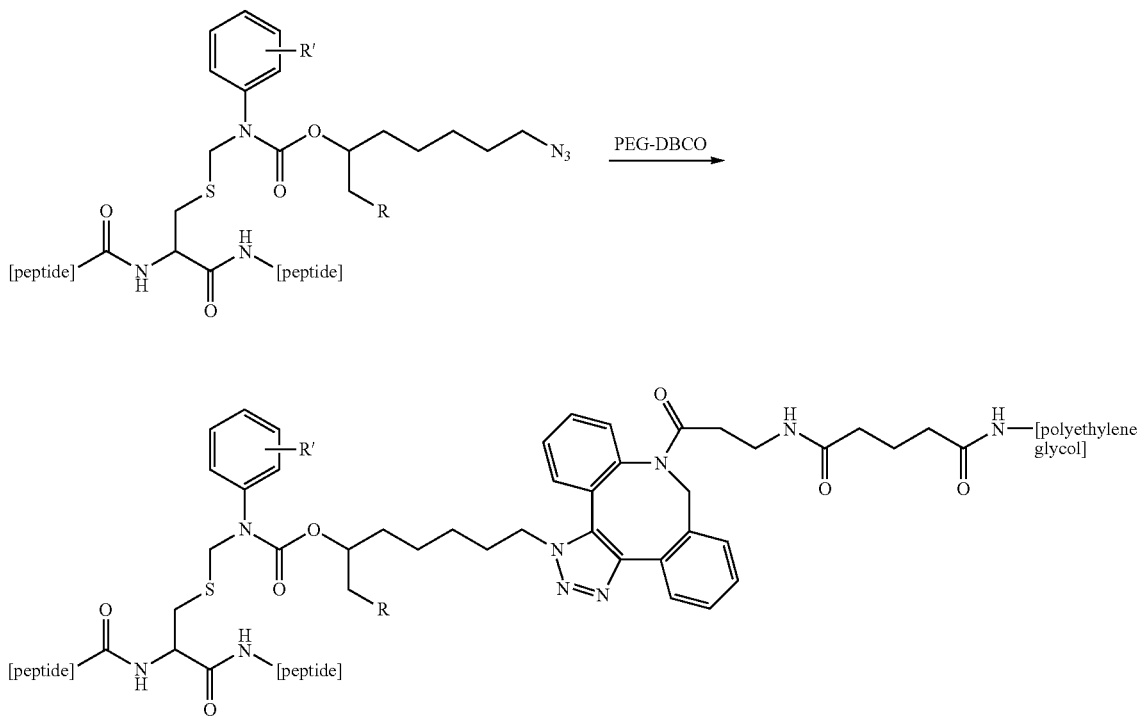

A solution of the thiol-linked peptide azide of Example 37 or 38 (1.5 equivalents) and the DBCO-activated polyethylene glycol (PEG-DBCO) (1 equivalent) in aqueous buffer is monitored by UV spectroscopy. Upon triazole formation, the characteristic absorbance of DBCO at 301 nm is lost. The reaction mixture is then dialyzed (10 kDa cutoff membrane) against 10 mM sodium acetate, pH 5.0 to remove excess azide.

Example 41

PEG-Conjugated Glutathione

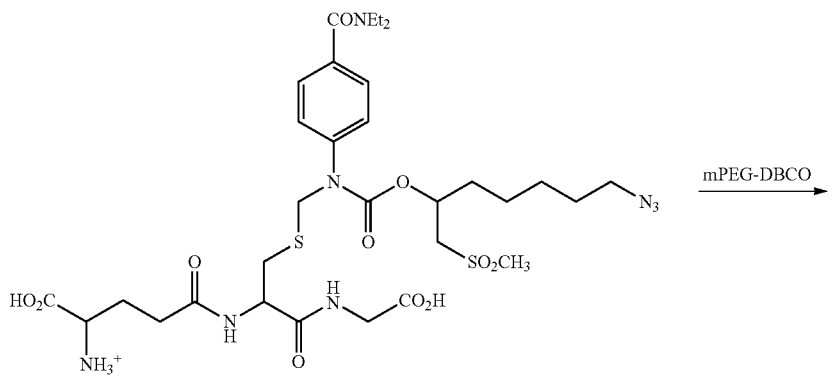

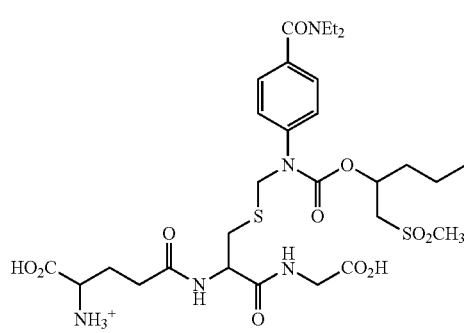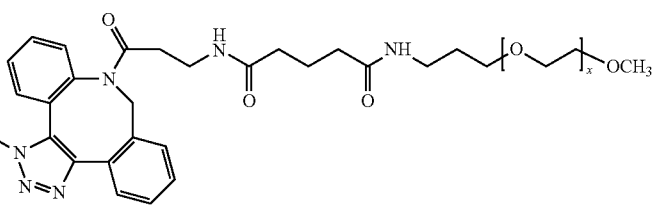

A solution of 40-kDa linear mPEG-DBCO (100 mg, 2.5 μmol) in 2.5 mL of 10 mM sodium acetate buffer, pH 5.0, was mixed with a solution of S-[N-(4-diethyl-carboxamido)phenyl N-(6-azido-1-(phenylsulfonyl)methyl)hexyloxy-carbonyl)aminomethyl]glutathione (65 mg/mL in methanol; 60 μL) and was kept at ambient temperature for 16 h, then passed through a PD-10 column (GE Health Sciences) equilibrated in water. The flow-through of the column containing macromolecules was collected and evaporated.

Example 42

Pharmacokinetics of 4-arm PEG-SN38 Conjugates in Rats (Experiment 2)

Dosing solutions were prepared by dissolving the 4-arm PEG-SN38 conjugates of Example 42 in 10 mM sodium acetate, pH 5.0, so as to give a final SN-38 concentration of 1 mM as determined by UV absorbance at 361 nm ($\epsilon$=22,500 $M^{-1}$ $cm^{-1}$). The dosing solutions were sterile filtered using a 0.2 μm syringe filter and frozen.

Figure 9:
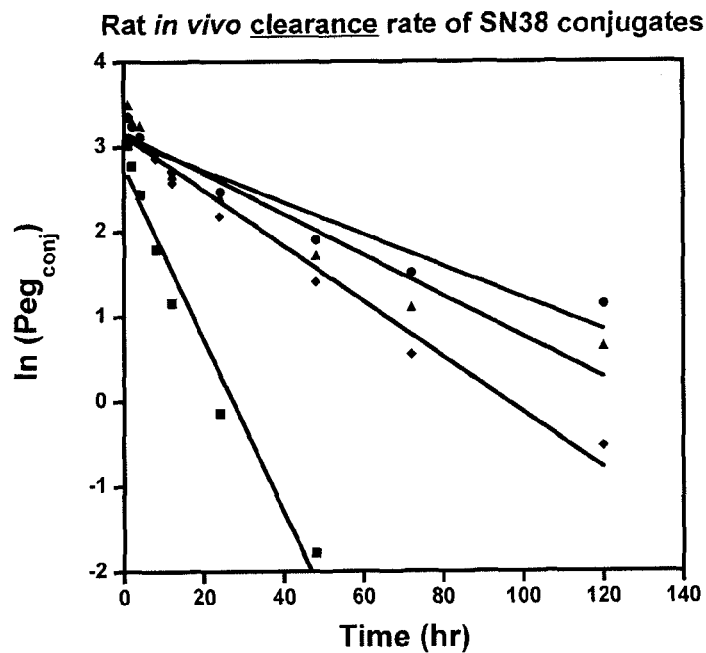
FIG. 9 shows the results of the 4-arm PEG-SN38 conjugate pharmacokinetics experiment described in Example 50. Panel A shows the concentration of various 4-arm PEG-SN38 conjugates after i.v. administration to rats. Conjugates wherein one of $R^1$ and $R^2$ is H and the other is phenylsulfonyl (squares), methanesulfonyl (diamonds), or morpholinosulfonyl (triangles), or $R^1$ and $R^2$ are both H as a control (circles) were administered to rats i.v., and plasma samples were analyzed for remaining conjugate as described in the working examples. Panel B shows a replot of the data to determine the rate of SN38 cleavage from the conjugates in vivo. A log plot of the ratio of the releasable conjugates (i.e., one of $R^1$ and $R^2$ is H and the other is phenylsulfonyl (squares), methanesulfonyl (diamonds), or morpholinosulfonyl (triangles)) to the unreleasable, "stable" conjugate (circles; i.e., $R^1$ and $R^2$ are both H as a control) at various times yields lines whose slopes are equal to the rate of SN38 release from the conjugates. It was observed that the rates of SN38 release in vivo were the same as those determined for the conjugates in vitro, with the following half-lives (modulator, in vitro $T_{1/2}$, in vivo $T_{1/2}$): phenylsulfonyl, 9.3 h, 10.4 h; methanesulfonyl, 44 h, 54 h; morpholinosulfonyl, 123 h, 137 h.
Figure 9:
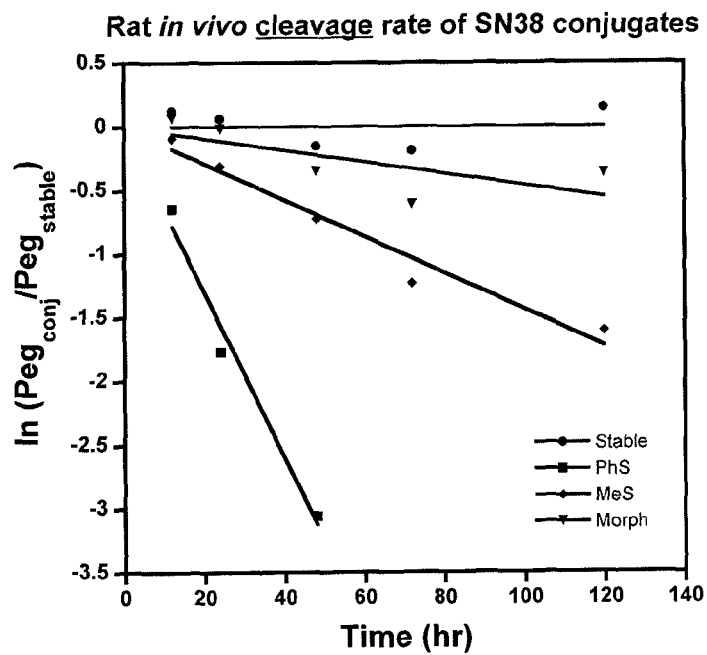

Samples were administered by i.v. injection to cannulated male Sprague Dawley rats at 100 μL/100 g body weight. A single rat per compound was used for a complete time course. Blood samples were collected at 0, 1, 2, 4, 8, 12, 24, 48, 72, and 120 hr. The serum was separated and frozen. The rat serum samples were thawed on ice. A 60 μL aliquot of a 0.25 mg/mL solution of $N_\epsilon$-(2,4,-dinitrophenyl)-L-lysine was added to 180 μL of each thawed serum sample. 2.5 μL of 2 M acetic acid was added to 100 μL aliquots of these samples, followed by 300 μL of methanol to precipitate serum proteins. The samples were left on ice for 1 h and centrifuged at 14,000 rpm. To a separate 100 μL aliquot of each sample, 50 μL of 200 mM $Et_3N$ was added and the aliquots were placed in a 37° C. incubator overnight (~16 hr) to hydrolyze the SN38 from PEG. A standard curve was prepared from a stock solution of the conjugate wherein R=phenylsulfonyl diluted in rat serum (Sigma-Aldrich) to 40 μM and treated following the same procedure as above. The samples and standards were analyzed for SN38 conjugate and total free SN38 on a Shimadzu HPLC with a Jupiter C4 400A 5u column using a 0-100% gradient of acetonitrile in $H_2O$ with 0.1% TFA over 10 minutes. SN38 was detected with a fluorescence detector set at 380 nm/515 nm excitation/emission. Sample concentrations were determined by fitting to the standard curve using Excel (Microsoft). The PK parameters were calculated using PK solutions software (Summit PK). The results of the experiment are shown in FIG. 9.

Example 43

Kinetics of Release

Rates of release of the drug from the conjugates of the invention can readily be determined by methods known in the art including chromatographic methods, such as HPLC. Where, for example, a fluorescent marker is used as a model system for the drug, the fluorescence attributable to freed fluorescent compound is readily determined as compared to fluorescence emitted by the conjugate.

The in vivo release of drug from the conjugates of the invention may be measured by determining the pharmacokinetics of the conjugates as compared with the pharmacokinetics of a non-releasable conjugate of the same size. For small molecule drugs, released drug is virtually immediately cleared from the plasma of any model system so that measurement of the free drug concentration in plasma can essentially be ignored, and it is only necessary to measure the concentration of the conjugate itself to calculate release rates when clearance of the intact conjugate of the system is compared. Such data are preferably obtained in rats as compared to mice as they exhibit more favorable clearance rates for the high molecular weight conjugates of the invention.

In more detail, the conjugates are administered to a model subject such as a rat, for example, by intravenous administration, and blood samples are periodically taken and plasma isolated. The level of conjugate in the plasma as a function of time is then determined. This may be done by chromatographic separation (for example, HPLC analysis after deproteinization coupled to UV, fluorescence, or mass spectrometric detection), or in appropriate cases by a direct assay such as ELISA, bioactivity, or fluorescence. As noted above, macromolecular conjugates adhere to a one-compartment model, conjugates of the invention can disappear from the plasma by one of two mechanisms: release of drug from the conjugate, and clearance of the intact conjugate (e.g., by renal filtration). The rate of loss of a releasable conjugate from the plasma is thus the sum of the rates of loss by release of the drug and by clearance of the conjugate. In contrast, the rate of loss of a non-releasable conjugate is just the rate of clearance of the conjugate from the plasma, since no drug is released. Thus, the rate of drug release from a conjugate of the invention can be calculated as the difference in rates of loss of the releasable conjugate from that of a corresponding non-releasable conjugate. This may be done by directly taking the difference in rates or this can be calculated from the slope of a plot of ln (R/N) versus time, where R is the concentration of releasable conjugate and N is the concentration of non-releasable conjugate, as shown in FIGS. 9a and 9b. As shown in panel a, the raw data simply show the logarithm (ln) of the concentration of various conjugates and of a stable conjugate as a function of time. Panel b shows the difference in release rates of various releasable conjugates which are obtained by the calculation described above. The stable conjugate, of course, shows zero release rate whereas release rates of drug from various embodiments of the trigger for release in sample conjugates are shown.

Figure 10:
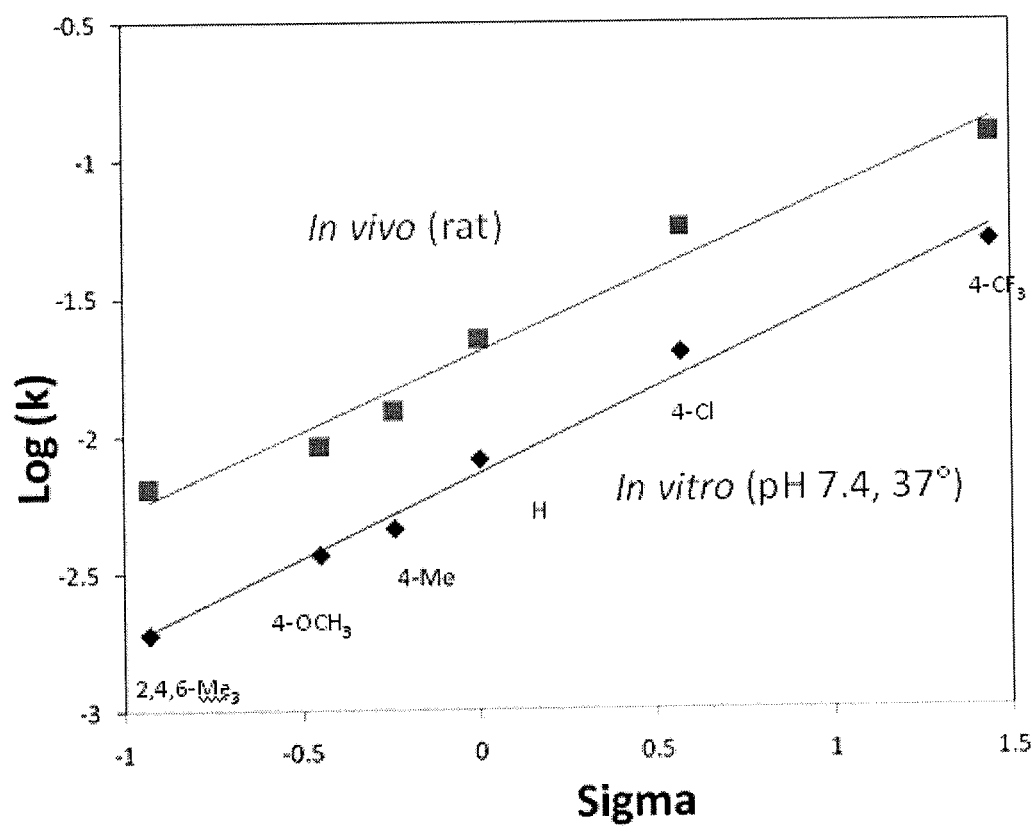
FIG. 10 shows a comparison of in vivo and in vitro release rates of drugs as a function of the Hammett constants associated with the trigger.

FIG. 10 shows that the variation of the rate constant as a function of the nature of the trigger in vitro and in vivo follow the same pattern.

The invention claimed is:

1. A compound of the formula

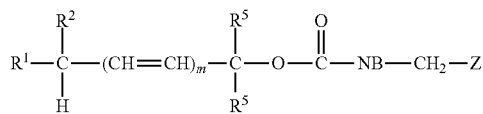

wherein m is 0 or 1;

wherein at least one, or both R¹ and R² is independently
CN; NO₂;
  optionally substituted aryl;
  optionally substituted heteroaryl;
  optionally substituted alkenyl;
  optionally substituted alkynyl;
  COR³ or SOR³ or SO₂R³ wherein
    R³ is H or optionally substituted alkyl;
    aryl or arylalkyl, each optionally substituted;
    heteroaryl or heteroarylalkyl, each optionally substituted; or
    OR⁹ or NR⁹₂ wherein each R is independently H or optionally substituted alkyl, or both R⁹ groups taken together with the nitrogen to which they are attached form a heterocyclic ring;
  SR⁴ wherein
    R⁴ is optionally substituted alkyl;
    aryl or arylalkyl, each optionally substituted; or
    heteroaryl or heteroarylalkyl, each optionally substituted;
wherein R¹ and R² may be joined to form a 3-8 membered ring; and
wherein one and only one of R¹ and R² may be H or alkyl, arylalkyl or heteroarylalkyl, each optionally substituted;
each R⁵ is independently H or is alkyl, alkenylalkyl, alkynylalkyl, aryl, arylalkyl, heteroaryl or heteroarylalkyl, each optionally substituted;
Z is a residue of a drug or prodrug coupled through O, S, or non-basic N or is a nucleofuge that mediates said coupling;
B is alkyl, aryl, arylalkyl, heteroaryl or heteroarylalkyl, each optionally substituted; and
wherein one of R¹, R², R⁵ or B is coupled to a macromolecule or one of R¹, R² or R⁵ comprises a functional group for mediating said coupling.

2. The compound of claim 1 wherein one of R¹ and R² is CN.

3. The compound of claim 1 wherein at least of one R¹ and R² comprises phenyl or phenylene.

4. The compound of claim 1 wherein one of R¹ and R² is SO₂R³ and the other is H, alkyl or phenyl.

5. The compound of claim 1 wherein m is 0.

6. The compound of claim 1 which is a drug conjugate of the formula

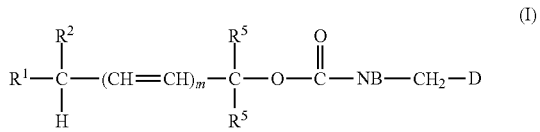

wherein R¹, R², R⁵, m and B are defined as in claim 1,
D is the residue of a drug or prodrug coupled through O, S or N; and
one of R¹, R², R⁵ or B is coupled to a macromolecule.

7. The drug conjugate of claim 6 wherein the macromolecule is polyethylene glycol (PEG).

8. The drug conjugate of claim 6 wherein the drug is a peptide, a nucleic acid or a small molecule.

9. The compound of claim 1 which is of the formula

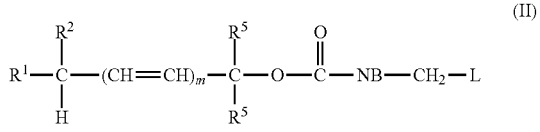

wherein R¹, R², R⁵, m and B are as defined in claim 1;
L is a nucleofuge that mediates the coupling of a drug or prodrug coupled through O, S or non-basic N; and
at least one of R¹, R² or R⁵ comprises a functional group for mediating coupling to a macromolecule.

10. The compound of claim 1 which is of the formula

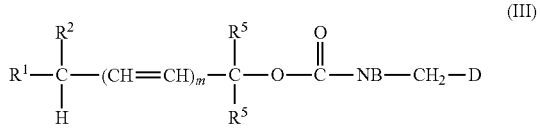

wherein m, R¹, R², R⁵, m, and B are as defined in claim 1;
wherein D is the residue of a drug or prodrug coupled through O, S or non-basic N; and
at least one of R¹, R², R⁵ or B comprises a functional group for mediating coupling to a macromolecule.

11. The compound of claim 1 which is of the formula

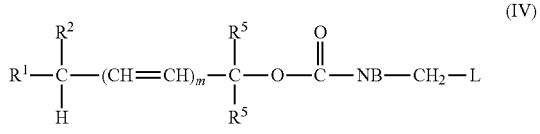

wherein the R¹, R², R⁵, m, and B are as defined in claim 1;
L is a nucleofuge that mediates the coupling of a drug or prodrug through O, S, or non-basic N; and
at least one of R¹, R², R⁵ or B is coupled to a macromolecule.

12. A method to prepare the compound of Formula (I) of claim 6 which method comprises reacting a compound of the formula

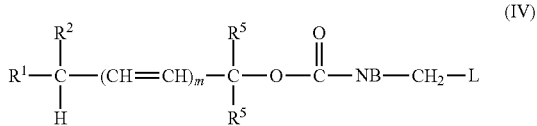

wherein $R^1$, $R^2$, $R^5$, m and B are as defined in claim 1;
L is a nucleofuge that mediates the coupling of a drug or prodrug through O, S, or non-basic N; and
wherein one of $R^1$, $R^2$, $R^5$ and B is coupled to a macromolecule;
with a drug or prodrug under conditions whereby said prodrug is coupled to said compound of formula (IV).

13. A method to prepare the compound of Formula (III) of claim 10 which method comprises reacting a compound of the formula

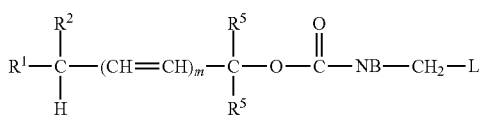

wherein m, $R^1$, $R^2$, $R^5$, m and B are as defined in claim 1;
L is a nucleofuge; and
at least one of $R^1$, $R^2$, $R^5$ or B comprises a functional group for mediating coupling to a macromolecule;
with a drug or prodrug under conditions whereby said drug or prodrug is coupled to said compound of formula (II).

14. A method to prepare the compound of Formula (I) of claim 6 which method comprises reacting a compound of the formula

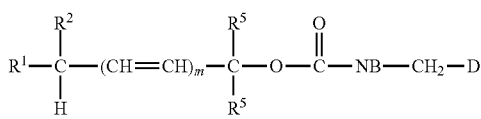

wherein m, $R^1$, $R^2$, $R^5$, m and B are as defined in claim 1;
and D is the residue of a drug or prodrug coupled through O, S or non-basic N; and
wherein at least one of $R^1$, $R^2$, $R^5$ and B comprises a functional group that couples formula (III) to a macromolecule;
with a macromolecule under conditions whereby said macromolecule is coupled to the compound of formula (III).

15. A method to prepare the compound of Formula (IV) of claim 11 which method comprises reacting a compound of the formula

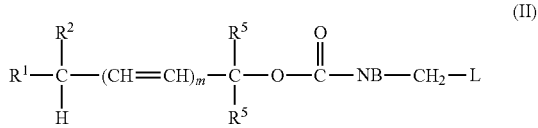

wherein m, $R^1$, $R^2$, $R^5$, m and B are as defined in claim 1;
L is a nucleofuge; and
wherein one of $R^1$, $R^2$, $R^5$ and B comprises a functional group that couples formula (II) to a macromolecule;
with a macromolecule under conditions whereby said macromolecule is coupled to the compound of formula (II).

16. The compound of claim 1 wherein Z is the residue of an SN-38 molecule.

17. A compound of formula (XX)

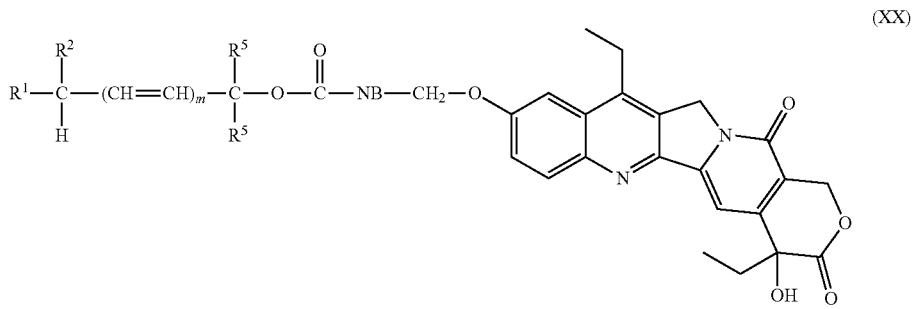

wherein $R^1$, $R^2$, $R^5$, m and B are as defined in claim 1.

18. The compound of claim 17 wherein m is 0.

19. The compound of claim 17 wherein m is 0; $R^1$ is phenylsulfonyl, substituted phenylsulfonyl, methanesulfonyl, $(R^9)_2N-SO_2$, or CN; $R^2$ is H; one $R^5$ is $N_3(CH_2)_5$ and the other $R^5$ is H; and B is phenyl or substituted phenyl.

20. The compound of claim 17 wherein m is 0; $R^1$ is phenylsulfonyl, substituted phenylsulfonyl, methanesulfonyl, $R_2N-SO_2$, or CN; $R^2$ is H; one $R^5$ is optionally substituted alkyl and the other $R^5$ is H; and B is phenyl or substituted phenyl, and wherein one of $R^1$, $R^5$, and B further comprises a connection to a macromolecule.

21. The compound of claim 17 wherein $R^2$ and one $R^5$ is H and the other $R^5$ is $N_3^+(CH_2)_5$, m is 0 and B is

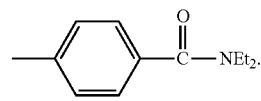

22. The compound of claim 21 wherein $R^1$ is CN.

* * * * *